(12) United States Patent
DiGianfilippo et al.

(10) Patent No.: US 7,171,992 B2
(45) Date of Patent: Feb. 6, 2007

(54) PHARMACEUTICAL COMPOUNDER

(75) Inventors: Aleandro DiGianfilippo, Scottsdale, AZ (US); Richard R. Pierce, Glendale, AZ (US)

(73) Assignee: B. Braun Medical Inc., Bethlehem, PA (US)

( * ) Notice: Subject to any disclaimer, the term of this patent is extended or adjusted under 35 U.S.C. 154(b) by 0 days.

(21) Appl. No.: 11/355,215

(22) Filed: Feb. 15, 2006

(65) Prior Publication Data

US 2006/0130927 A1 Jun. 22, 2006

Related U.S. Application Data

(62) Division of application No. 10/335,552, filed on Dec. 31, 2002.

(60) Provisional application No. 60/344,869, filed on Dec. 31, 2001.

(51) Int. Cl.
*B65B 1/04* (2006.01)

(52) U.S. Cl. .......................... 141/99; 141/102; 141/105; 604/131; 604/151; 417/478

(58) Field of Classification Search .................. 141/67, 141/99, 100, 102, 105; 417/478; 74/125.5; 604/67, 131, 151, 249, 251, 258
See application file for complete search history.

(56) References Cited

U.S. PATENT DOCUMENTS

| | | | |
|---|---|---|---|
| 4,333,356 A | 6/1982 | Bartels et al. | |
| 4,443,333 A * | 4/1984 | Mahurkar | ..................... 210/87 |
| 4,467,844 A | 8/1984 | DiGianfilippo et al. | |
| 4,513,796 A | 4/1985 | Miller et al. | |
| 4,604,847 A | 8/1986 | Moulding, Jr. et al. | |
| 4,648,430 A | 3/1987 | DiGianfilippo et al. | |
| 4,653,010 A | 3/1987 | Figler et al. | |
| 4,712,590 A | 12/1987 | Gianfilippo | |
| 4,718,467 A | 1/1988 | DiGianfilippo et al. | |
| 4,789,014 A | 12/1988 | DiGianfilippo et al. | |

(Continued)

FOREIGN PATENT DOCUMENTS

GB 2 293 664 A 4/1996

(Continued)

OTHER PUBLICATIONS

Supplementary Partial European Search Report of European Application No. 02796129 dated Nov. 15, 2005.

*Primary Examiner*—Timothy L. Maust
(74) *Attorney, Agent, or Firm*—RatnerPrestia

(57) ABSTRACT

Information management systems and methods can be used with at least one pharmaceutical compounding device. The systems and methods comprise a controller coupled to the compounding device. A compounding control manager resides on the controller to receive compounding order input and generate control commands to the compounding device based, at least in part, upon the compounding order input. An order process control manager is in data communication with the compounding control manager to communicate compounding order input to the compounding control manager. The order entry process manager includes an order function for receiving entry of compounding order input through a browser-based interface. The browser-based interface can include an order entry workstation separate from the compounding device, or a network of order entry workstations separate from the compounding device, or can reside on the controller.

4 Claims, 76 Drawing Sheets

U.S. PATENT DOCUMENTS

| | | | |
|---|---|---|---|
| 4,823,833 A | 4/1989 | Hogan et al. | |
| 4,922,975 A | 5/1990 | Polaschegg | |
| 4,967,811 A | 11/1990 | DiGianfilippo et al. | |
| 5,025,954 A | 6/1991 | Dunnous | |
| 5,040,699 A | 8/1991 | Gangemi | |
| 5,056,568 A | 10/1991 | DiGianfilippo et al. | |
| 5,056,992 A * | 10/1991 | Simons et al. | 417/474 |
| 5,076,332 A | 12/1991 | Lewis et al. | |
| 5,085,256 A | 2/1992 | Kircher et al. | |
| 5,228,485 A * | 7/1993 | Lewis et al. | 141/83 |
| 5,313,992 A | 5/1994 | Grabenkort | |
| 5,316,181 A | 5/1994 | Burch | |
| 5,364,526 A | 11/1994 | Matkovich et al. | |
| 5,402,834 A | 4/1995 | Levin et al. | |
| 5,431,201 A | 7/1995 | Torchia et al. | |
| 5,431,202 A | 7/1995 | Dikeman et al. | |
| 5,450,847 A | 9/1995 | Kampfe et al. | |
| 5,464,047 A | 11/1995 | Muscara | |
| 5,470,488 A | 11/1995 | Matkovich et al. | |
| 5,507,412 A | 4/1996 | Ebert et al. | |
| 5,510,621 A | 4/1996 | Goldman | |
| 5,511,594 A | 4/1996 | Brennan et al. | |
| 5,592,940 A | 1/1997 | Kampfe et al. | |
| 5,597,094 A | 1/1997 | Vilbert | |
| 5,626,172 A | 5/1997 | Schumacher et al. | |
| 5,637,103 A | 6/1997 | Kerwin et al. | |
| 5,697,407 A | 12/1997 | Lasonde | |
| 5,750,998 A | 5/1998 | Goldman | |
| 5,772,966 A | 6/1998 | Maracas et al. | |
| 5,803,906 A | 9/1998 | Pratt et al. | |
| 5,820,048 A | 10/1998 | Shereyk et al. | |
| 5,884,806 A | 3/1999 | Boyer et al. | |
| 5,887,139 A | 3/1999 | Madison, Jr. et al. | |
| 5,927,349 A | 7/1999 | Martucci et al. | |
| 6,070,761 A | 6/2000 | Bloom et al. | |
| 6,079,462 A | 6/2000 | Martucci et al. | |
| 6,112,986 A | 9/2000 | Berger et al. | |
| 6,199,603 B1 | 3/2001 | DiGianfilippo et al. | |
| 6,202,711 B1 | 3/2001 | Martucci et al. | |
| 6,208,911 B1 | 3/2001 | Yamaoka et al. | |
| 6,213,174 B1 | 4/2001 | Cook et al. | |
| 6,296,450 B1 | 10/2001 | Westberg et al. | |
| 6,319,243 B1 | 11/2001 | Becker et al. | |
| 6,481,180 B1 | 11/2002 | Takahashi et al. | |
| 6,519,569 B1 | 2/2003 | White et al. | |
| 6,554,791 B1 * | 4/2003 | Cartledge et al. | 604/67 |
| 6,685,678 B2 | 2/2004 | Evans et al. | |
| 6,711,460 B1 | 3/2004 | Reese | |
| 2001/0005865 A1 | 6/2001 | Byrnes et al. | |
| 2002/0035412 A1 | 3/2002 | Kircher et al. | |
| 2002/0077857 A1 | 6/2002 | Seelinger | |
| 2002/0188468 A1 | 12/2002 | Hogan | |

FOREIGN PATENT DOCUMENTS

| | | |
|---|---|---|
| JP | 03 012159 A | 1/1991 |
| JP | 2000 300981 A | 10/2000 |
| WO | WO 03/058507 A1 | 7/2003 |

* cited by examiner

| | Additives | | | |
|---|---|---|---|---|
| | Potassium Chloride | /Liter | 40.0 | change |
| | Sodium Acetate | 20.00 mL | | |
| | | /100Kg | 10.2 | change |
| | Zinc | 30.00 mL | | |
| | | /100Kg | 0.2 | change |
| | Heparin | 0.50 mL | | |
| | | /KgH | 34.0 | change |
| | Aminophylline | 1000.00 unit | | |
| | | /LbH | 30.8 | change |
| | Sodium Chloride | 1.00 mL | | |
| | | /500mL | 60.0 | change |
| | | 15.00 mEq | | |

Add Solution to Order

Solution     Order Dose     Per

Click to Submit Change or Additions    Submit Changes

Nutritional Summary

Nutritional Content Summary
4.18 gm Nitrogen
118.195 Kcal Protein
522.445 Kcal Dextrose
275.000 Kcal Lipid
915.640 Kcal Total Total Volume: 2000.0 mL Electrolyte Content Summary
0 mEq NA+
0 mEq K+
0 mEq CA++
0 mEq Mg++
0 mEq CL-
0 mMol PO4--
0 mEq AC Osmolarity 14117.4

Order Status

*Fig. 11E (3)*

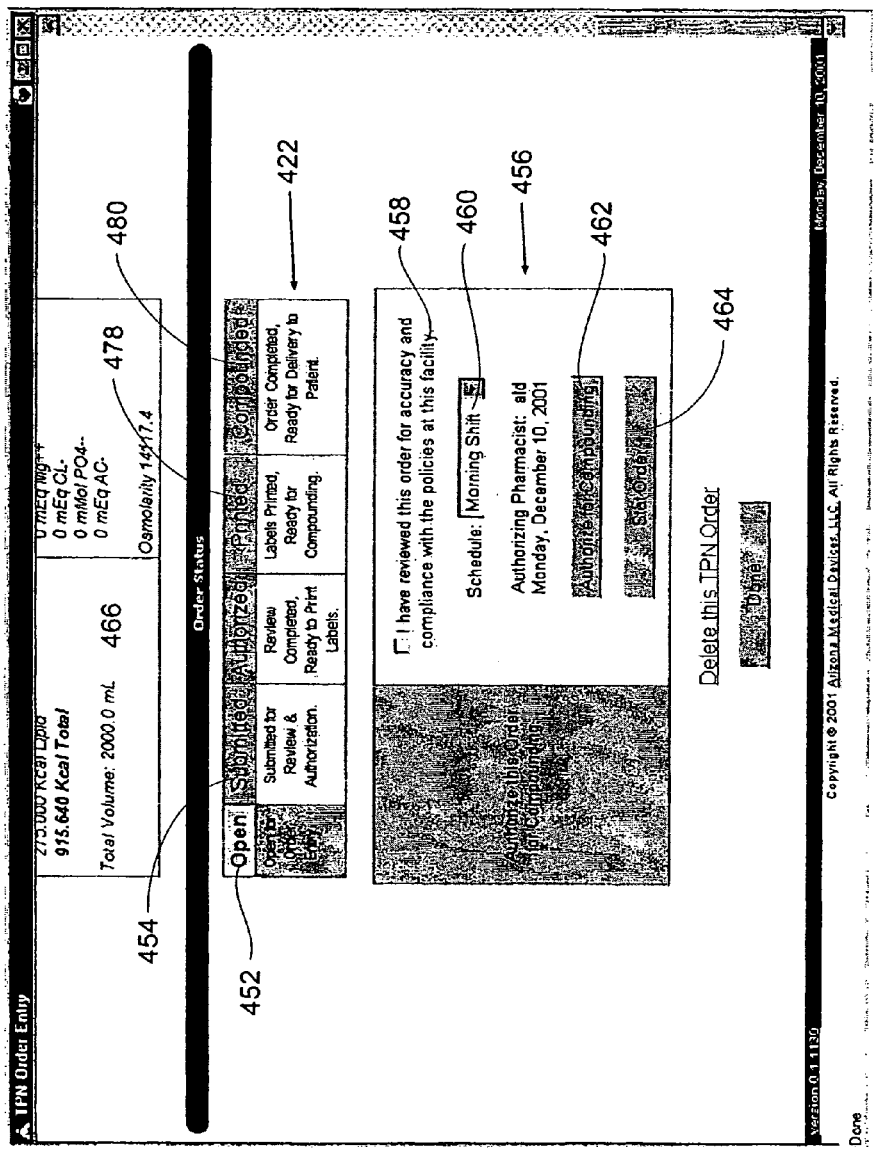
Fig. 11E (4)

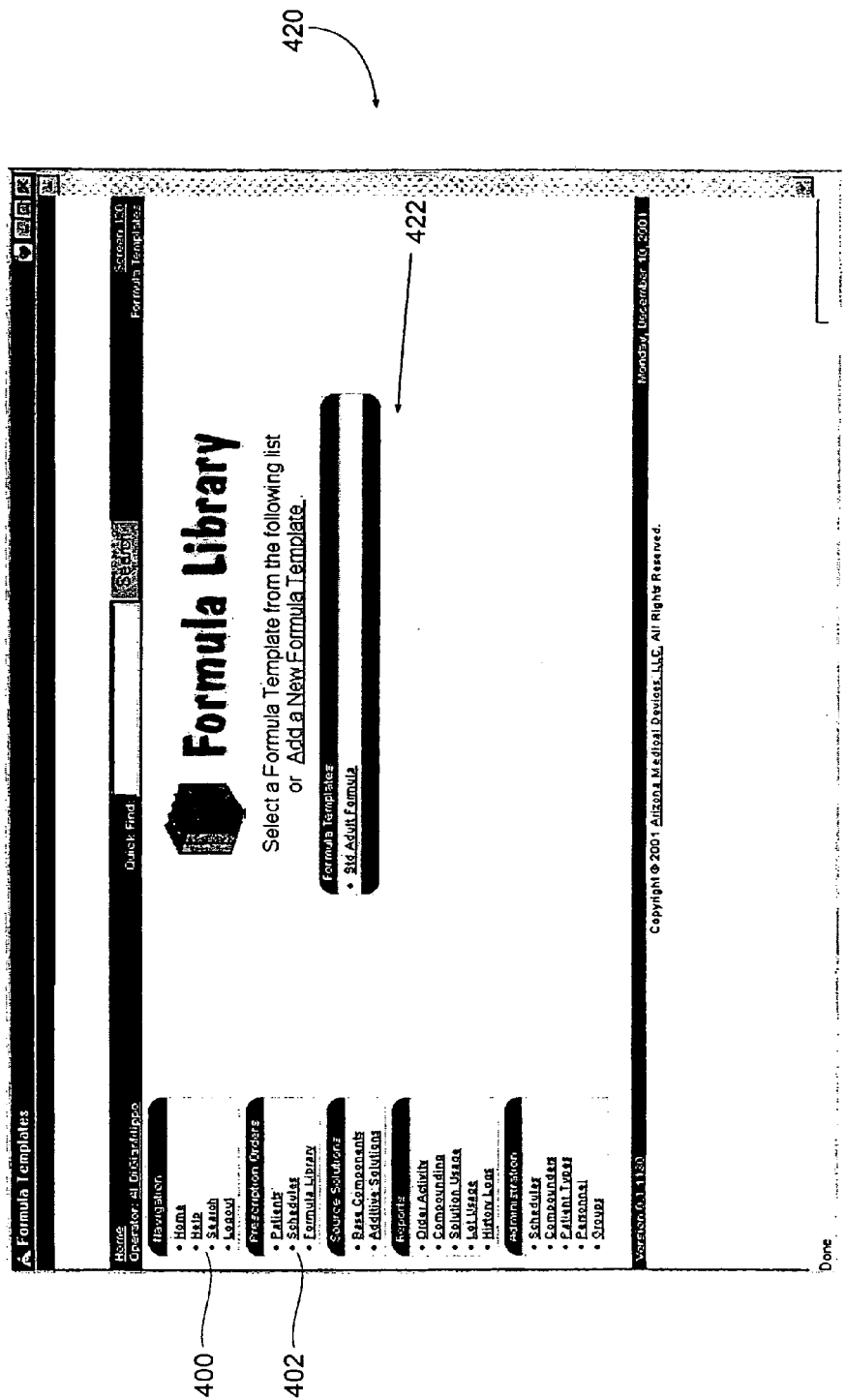
Fig. 11F (1)

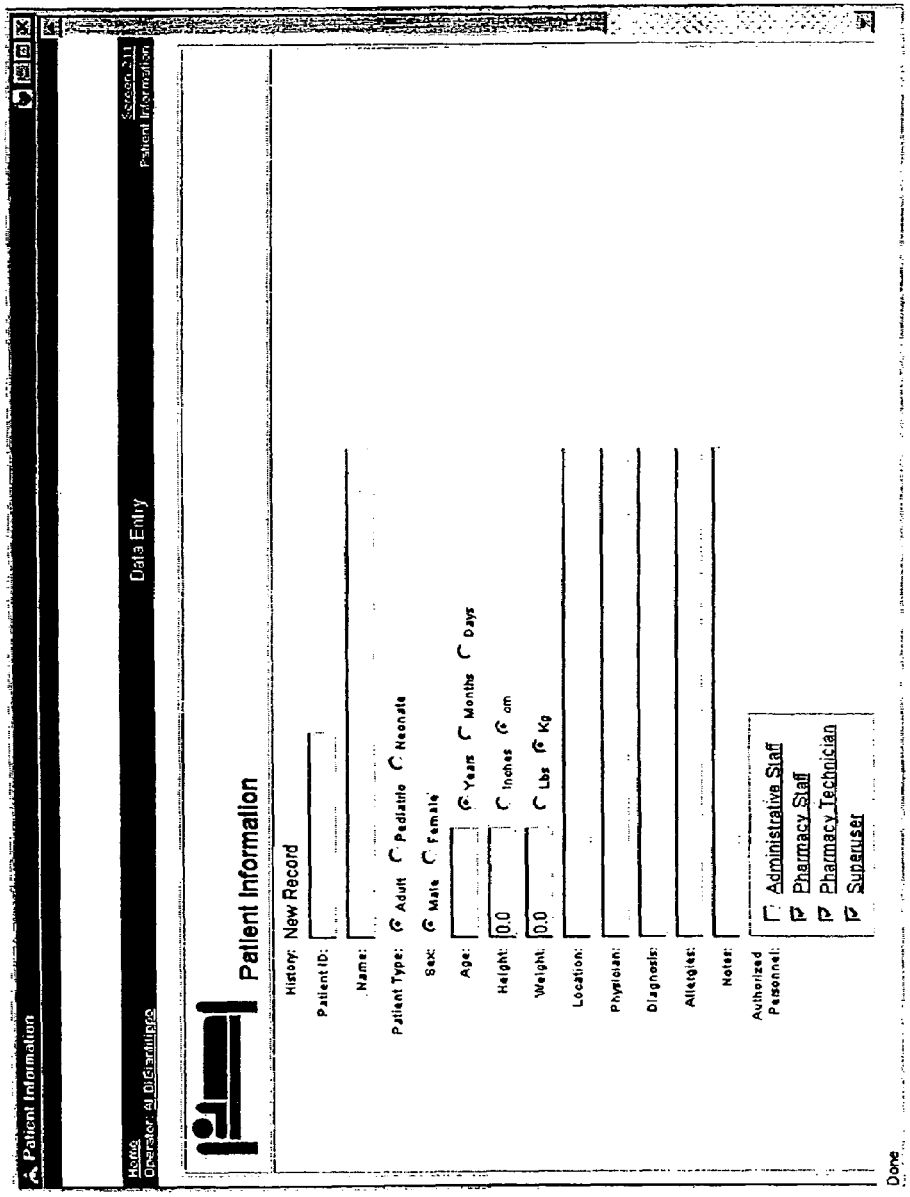
Fig. 11G (1)

Fig. 11G (2)

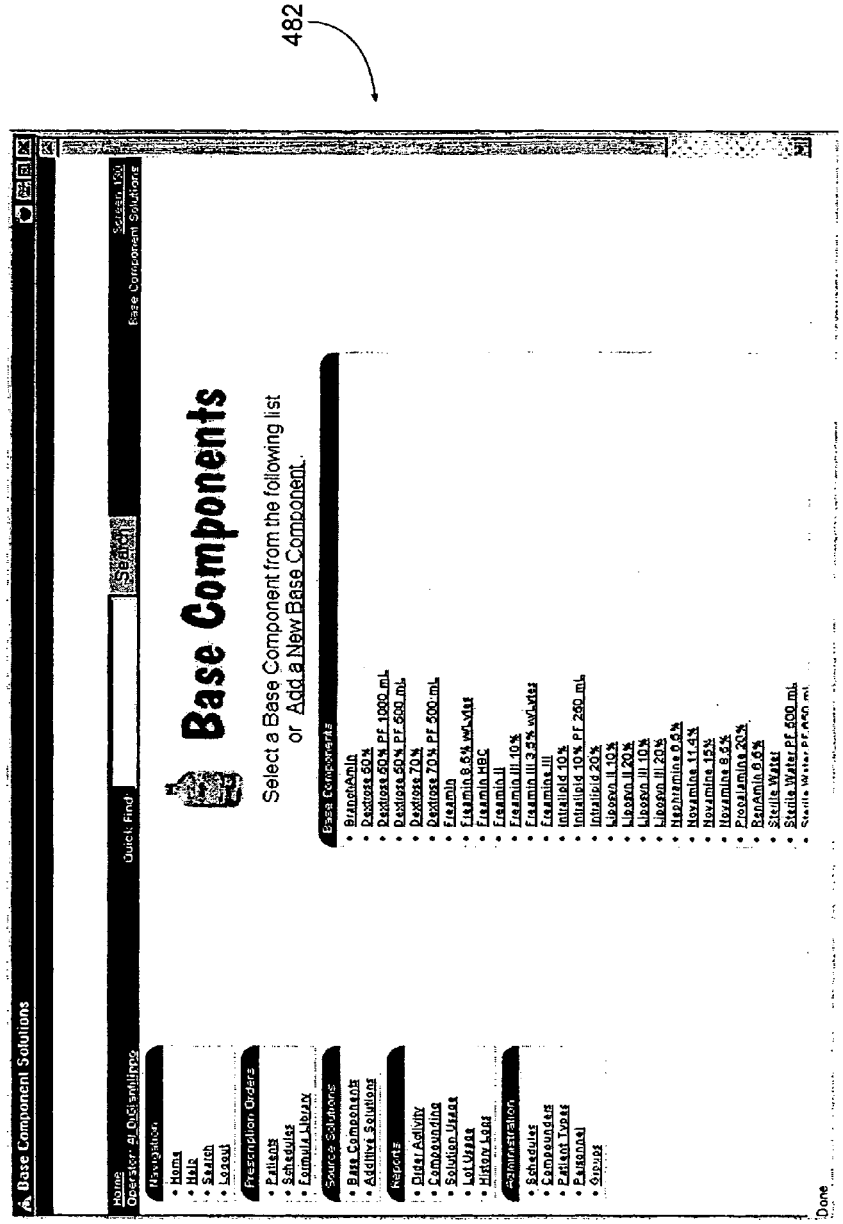
Fig. 11H (1)

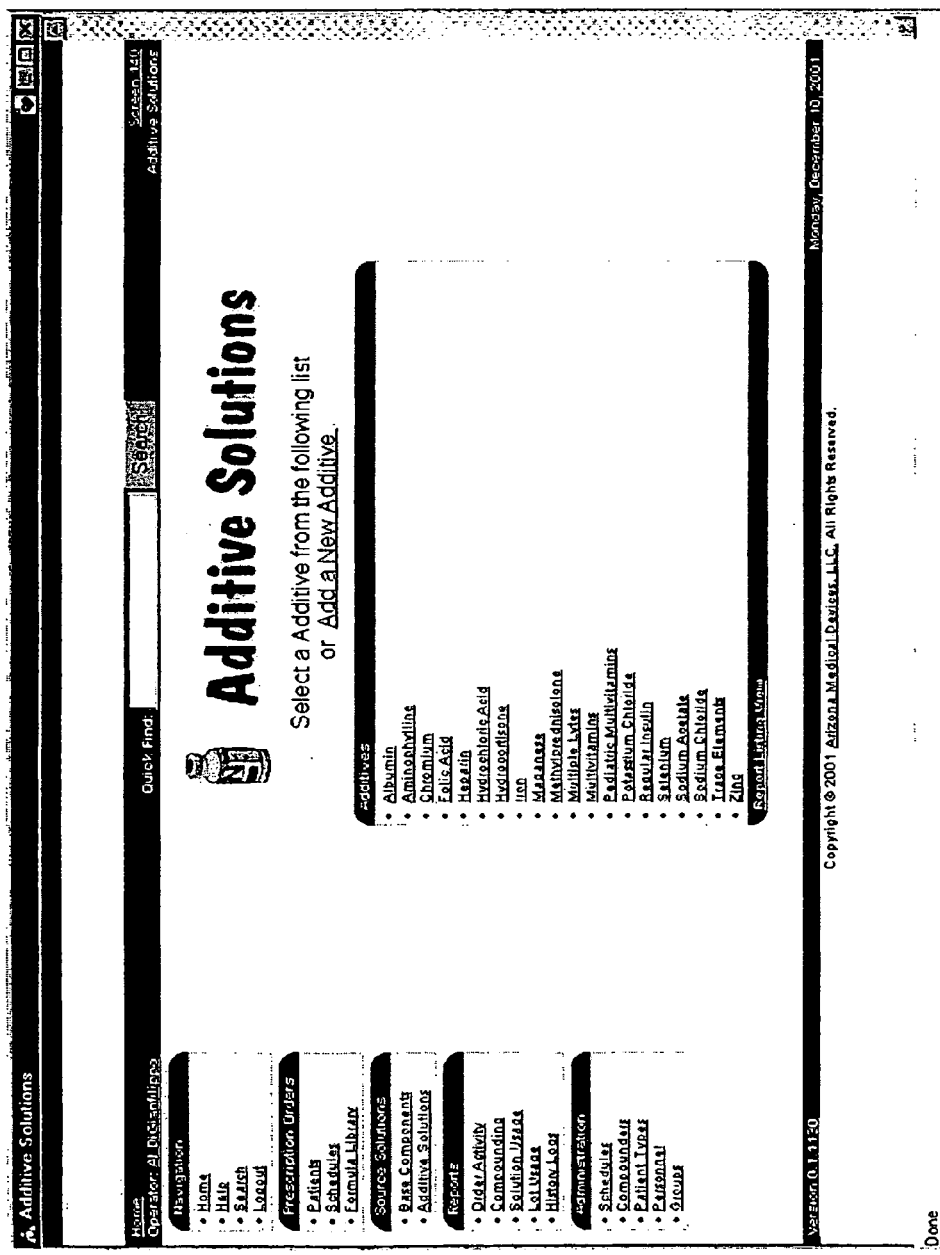
Fig. 11-I (1)

272
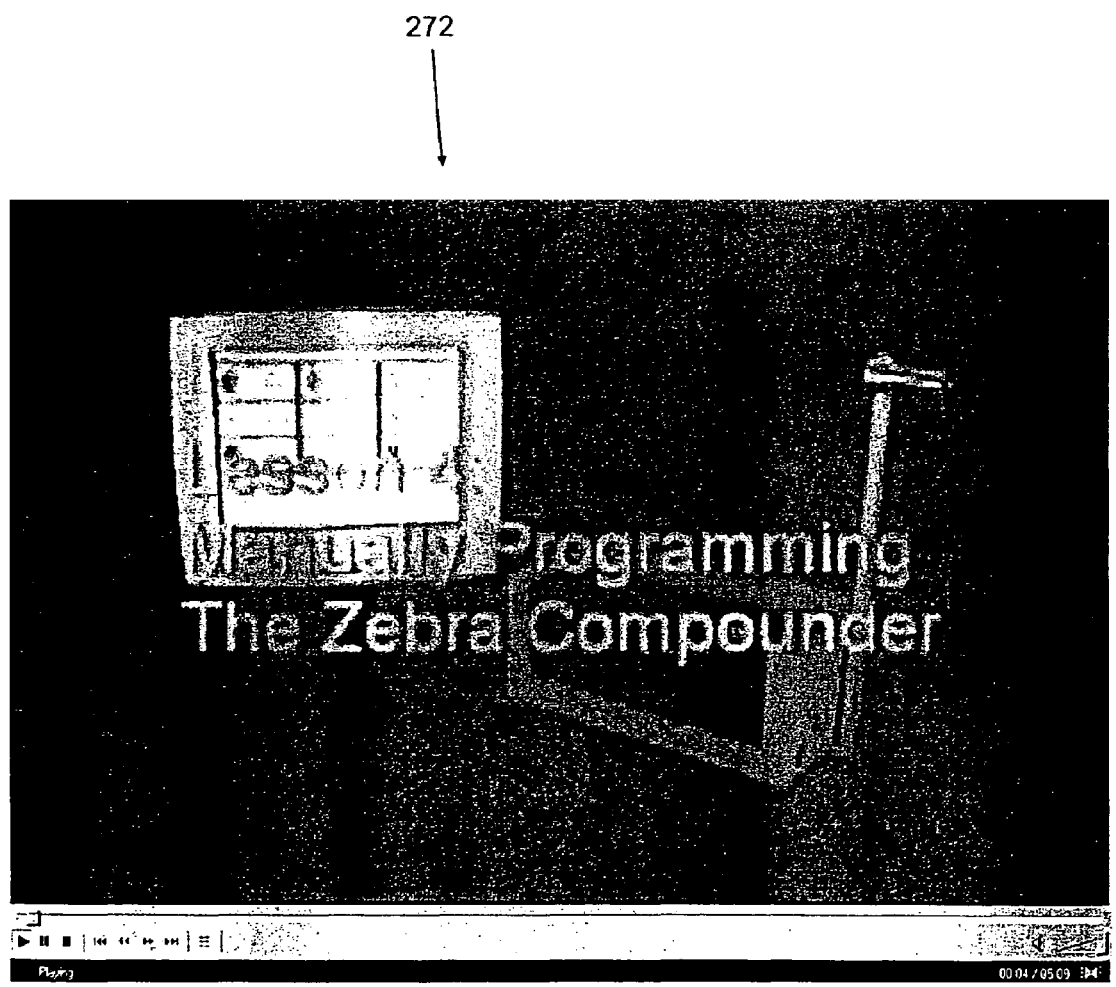
Fig. 14B (1)

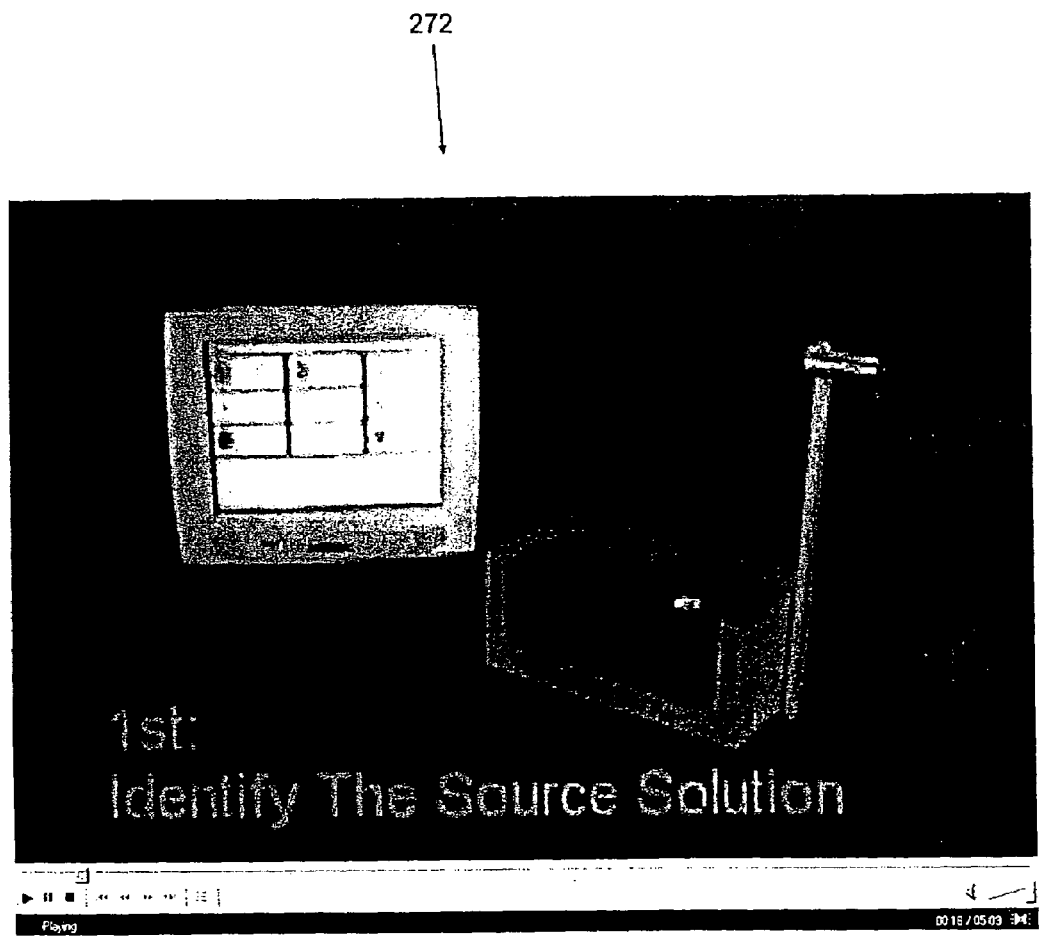
Fig. 14B (2)

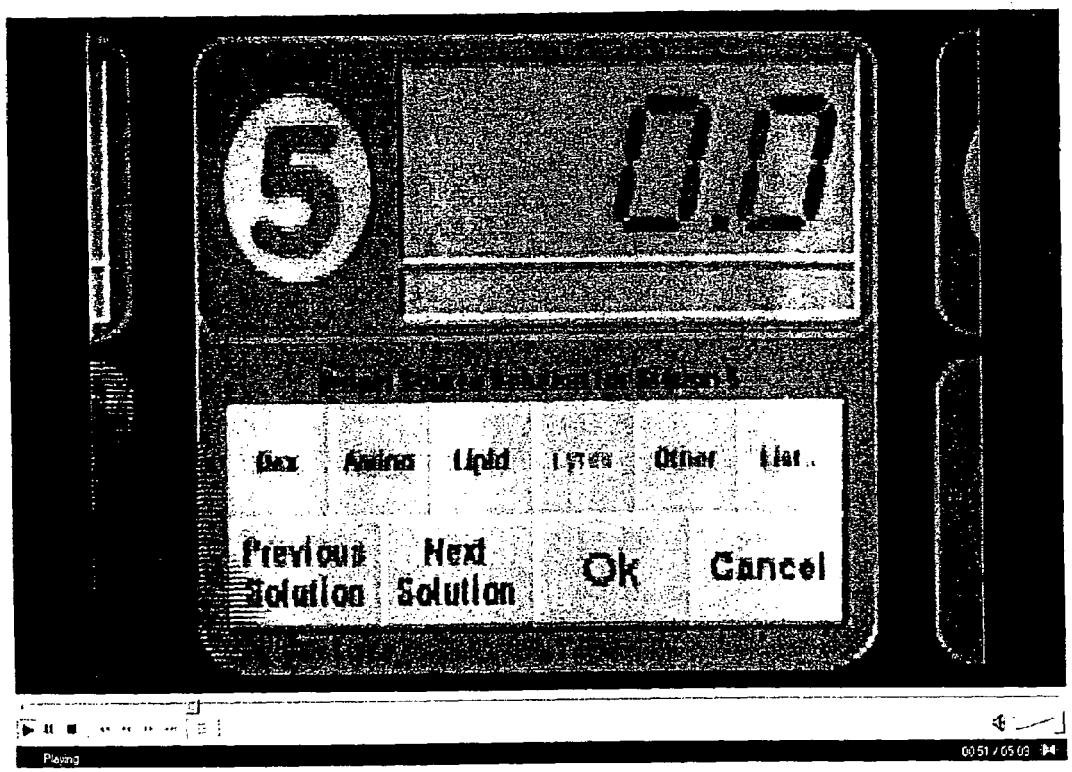
Fig. 14B (3)

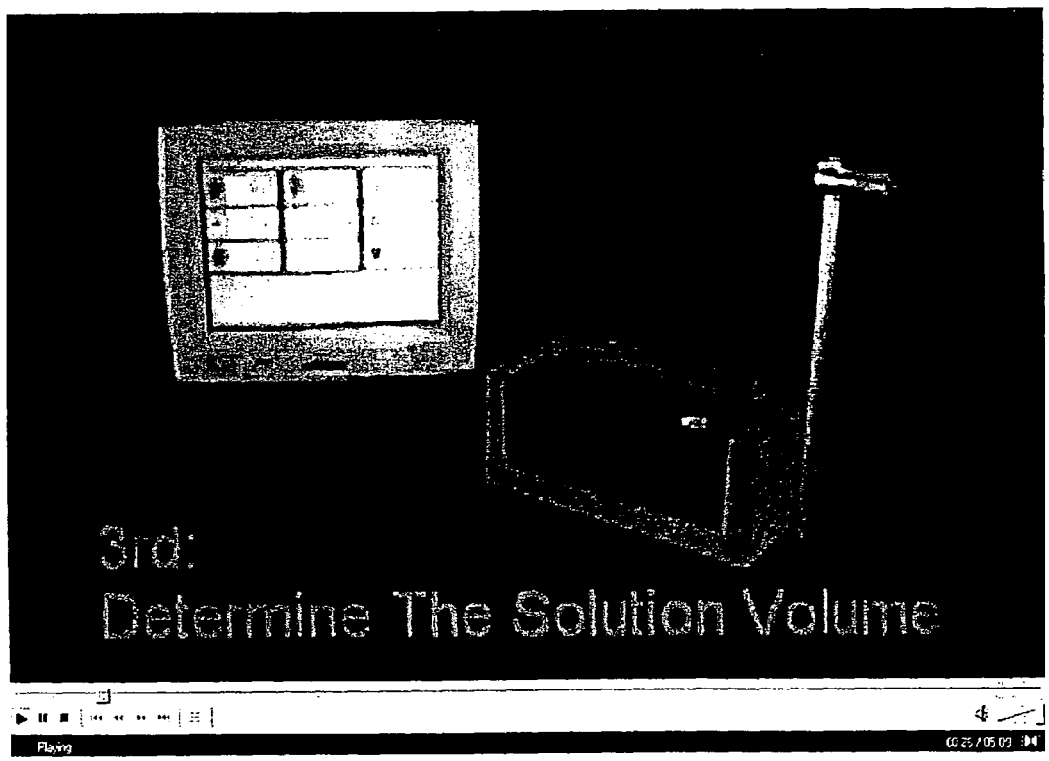
Fig. 14B (4)

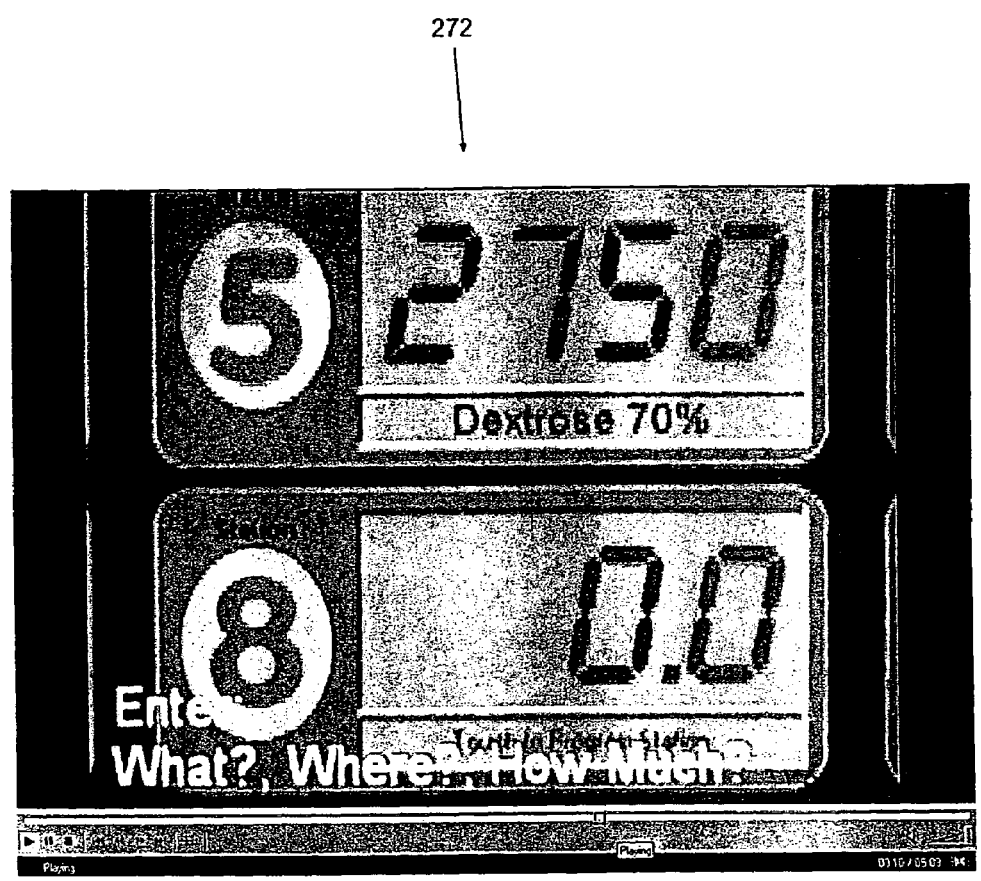
Fig. 14B (5)

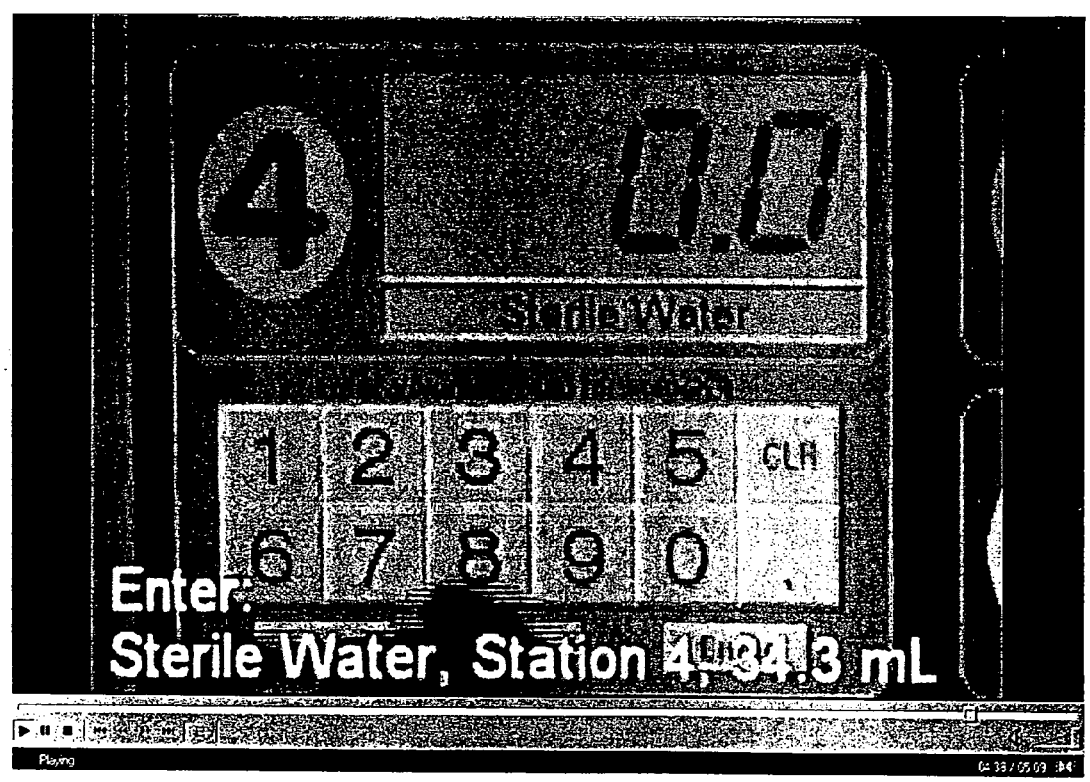
Fig. 14B (6)

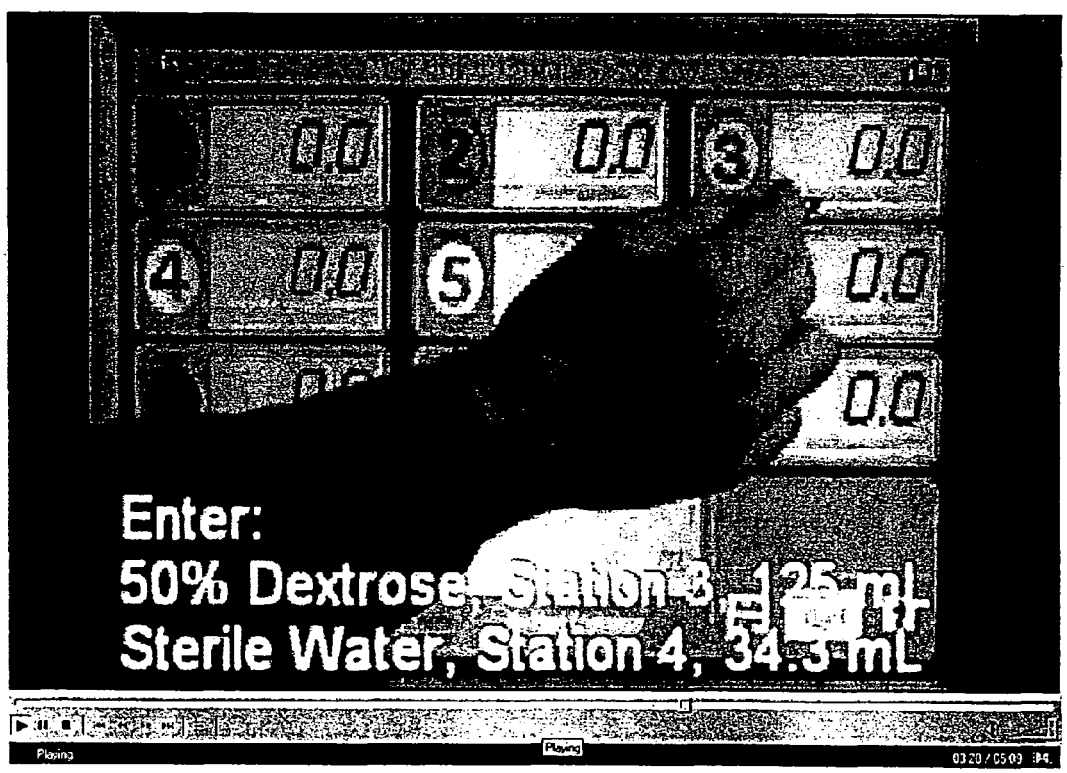
Fig. 14B (7)

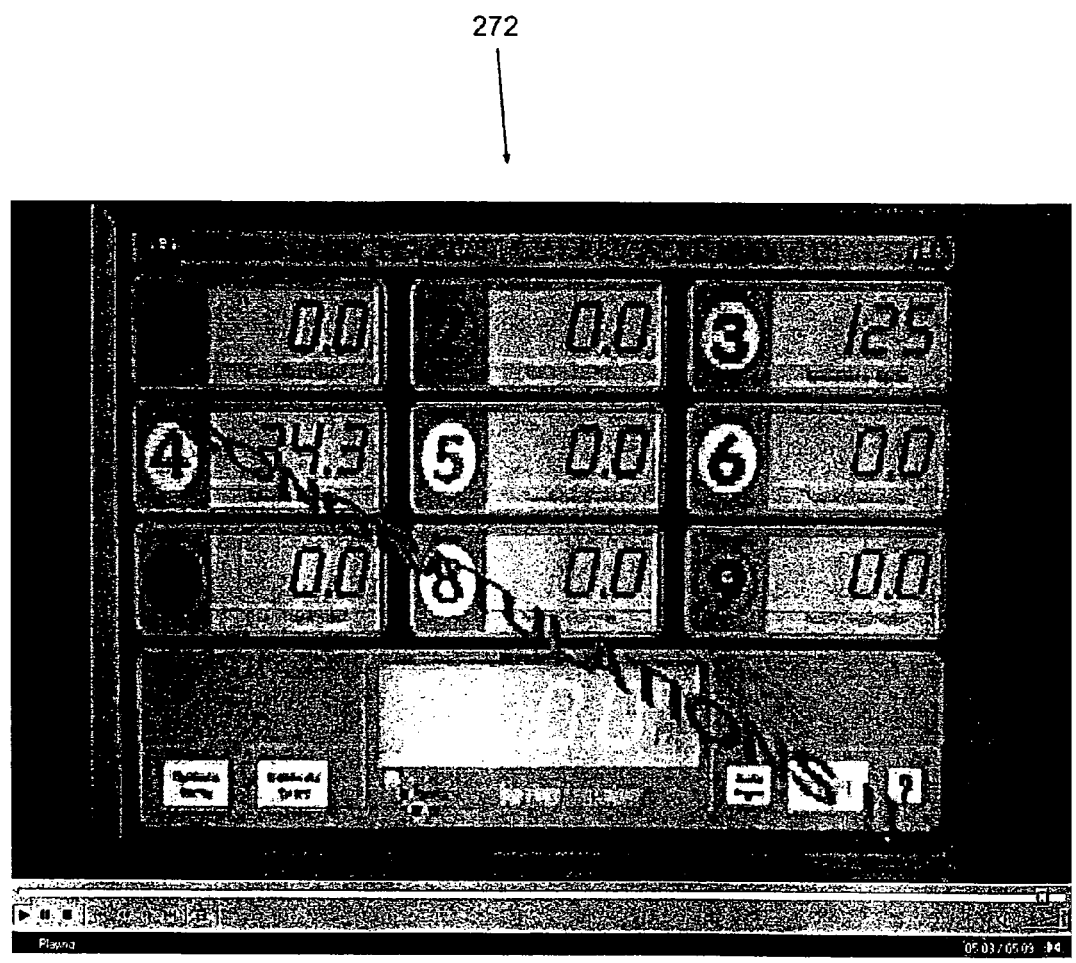
Fig. 14B (8)

PHARMACEUTICAL COMPOUNDER

RELATED APPLICATIONS

This application is a Divisional application of U.S. application Ser. No. 10/335,552, filed Dec. 31, 2002 which claimed the benefit of priority of U.S. Provisional Application No. 60/344,869, filed Dec. 31, 2001.

FIELD OF THE INVENTION

This invention relates to systems and methods for compounding of liquids and/or drugs intended to be administered to a human being or an animal.

BACKGROUND OF THE INVENTION

Pharmaceutical compounding involves the transfer of two or more of individual prescribed liquids and/or drugs from multiple source containers into a single collecting container, for the purpose of administering the mix of liquids and/or drugs intravenously to an individual in need. Presently, the pharmaceutical compounding of liquids and/or drugs takes place primarily at one of three sites. These are: (1) hospital based compounding performed by pharmacists or pharmacy technicians in the hospital pharmacy; (2) alternate site based compounding performed primarily by pharmacists or pharmacy technicians in the home care company pharmacy; and (3) compounding centers operated by any one of several major pharmaceutical or hospital supply companies.

The operational and performance demands upon these compounding systems and methodologies are becoming increasingly more complex and sophisticated, in terms of, e.g., safety, speed, reliability, accuracy, and overall user friendliness and ergonomics. The operational and performance demands upon these compounding systems and methodologies are also becoming increasingly more complex and sophisticated with regard to the management of patient and prescription information, in terms of providing an information path that starts with the clinician and finishes with the final product delivery to the end patient.

SUMMARY OF THE INVENTION

One aspect of the invention provides information management systems and methods adapted to be used with at least one pharmaceutical compounding device. The systems and methods comprise a controller coupled to the compounding device. A compounding control manager resides on the controller to receive compounding order input and generate control commands to the compounding device based, at least in part, upon the compounding order input. An order process control manager is in data communication with the compounding control manager to communicate compounding order input to the compounding control manager. The order entry process manager includes an order function for receiving entry of compounding order input through a browser-based interface.

The browser-based interface can include an order entry workstation separate from the compounding device, or a network of order entry workstations separate from the compounding device, or can reside on the controller.

The order entry process manager can include a database function for retaining the compounding order input in memory, a printing function for generating printable output, e.g., labeling, based, at least in part, upon the compounding order input, or a report function for generating reporting output based, at least in part, upon the compounding order input.

Another aspect of the invention provides a pharmaceutical compounding device that comprises at least one pump element, a controller coupled to the pumping element, and a compounding control manager residing on the controller to receive compounding order input and generate control commands to the pump element based, at least in part, upon the compounding order input. According to this aspect of the invention, the compounding control manager includes a verification function that requires a prescribed bar code input before generation of the control commands. The bar code input can include, e.g., a source solution identification, and/or a source solution lot number, and/or a source solution expiration date.

Another aspect of the invention provides an interface for performing a pharmaceutical compounding procedure using a compounding device. The interface comprises a controller coupled to the compounding device, a display screen coupled to the controller, and a compounding control manager residing on the controller to receive compounding order input and generate control commands to the compounding device based, at least in part, upon the compounding order input. According to this aspect of the invention, the compounding control manager includes a graphical user interface generated on the display screen that includes at least one touch-screen function for receiving compounding order input. The touch-screen function can affect, e.g., the selection of a source solution, or the selection of an amount of liquid to be transferred. The compounding control manager can also include a help function executed through the graphical user interface, or an informational video executed through the graphical user interface.

Another aspect of the invention provides an interface for performing a pharmaceutical compounding procedure using a compounding device. The interface comprises a controller coupled to the compounding device, a display screen coupled to the controller, and a compounding control manager residing on the controller to receive compounding order input and generate control commands to the compounding device based, at least in part, upon the compounding order input. According to this aspect of the invention, the compounding control manager includes at least one informational video displayable on the display screen.

Another aspect of the invention provides a pharmaceutical compounding device that comprises a driver and a drive shaft coupled to the driver for rotation. The drive shaft extends along a first axis. The device also includes an idler shaft that extends along a second axis offset from the first axis. A peristaltic pump rotor is carried on the idler shaft. A drive gear is carried on the drive shaft and coupled to the peristaltic pump rotor. A clutch assembly is carried on the drive shaft and coupled to the drive gear. The clutch assembly is operable in a first mode to disengage the drive gear from the drive shaft and a second mode to engage the drive gear with the drive shaft. The clutch assembly thereby selectively imparts rotation of the drive shaft to the peristaltic pump rotor.

Another aspect of the invention provides a fluid transfer set. The set comprises first transfer tubing, second transfer tubing, and a manifold that joins the first transfer tubing and second transfer tubing in flow communication. A first one way valve is in-line in the first transfer tubing to allow fluid flow in the first transfer tubing toward the manifold but not in an opposite direction. The first one-way valve has a first cracking pressure. A second one way valve is in-line in the second transfer tubing to allow fluid flow in the second transfer tubing toward the manifold but not in an opposite direction. The second one-way valve has a second cracking pressure different than the first cracking pressure. When used in pharmaceutical compounding, the transfer set can mediate lipid hazing.

Other features and advantages of the inventions are set forth in the following specification and attached drawings.

BRIEF DESCRIPTION OF THE DRAWINGS

FIGS. 11A to 11I are representative screens of a browser-based graphical user interface that makes accessible to a remote workstation the functional modules of the order entry process manager shown in FIGS. 10A to 10E.

FIG. 12 is a representative view of labeling that the order entry process manager shown in FIGS. 10A to 10E and FIGS. 11A to 11I can generate.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
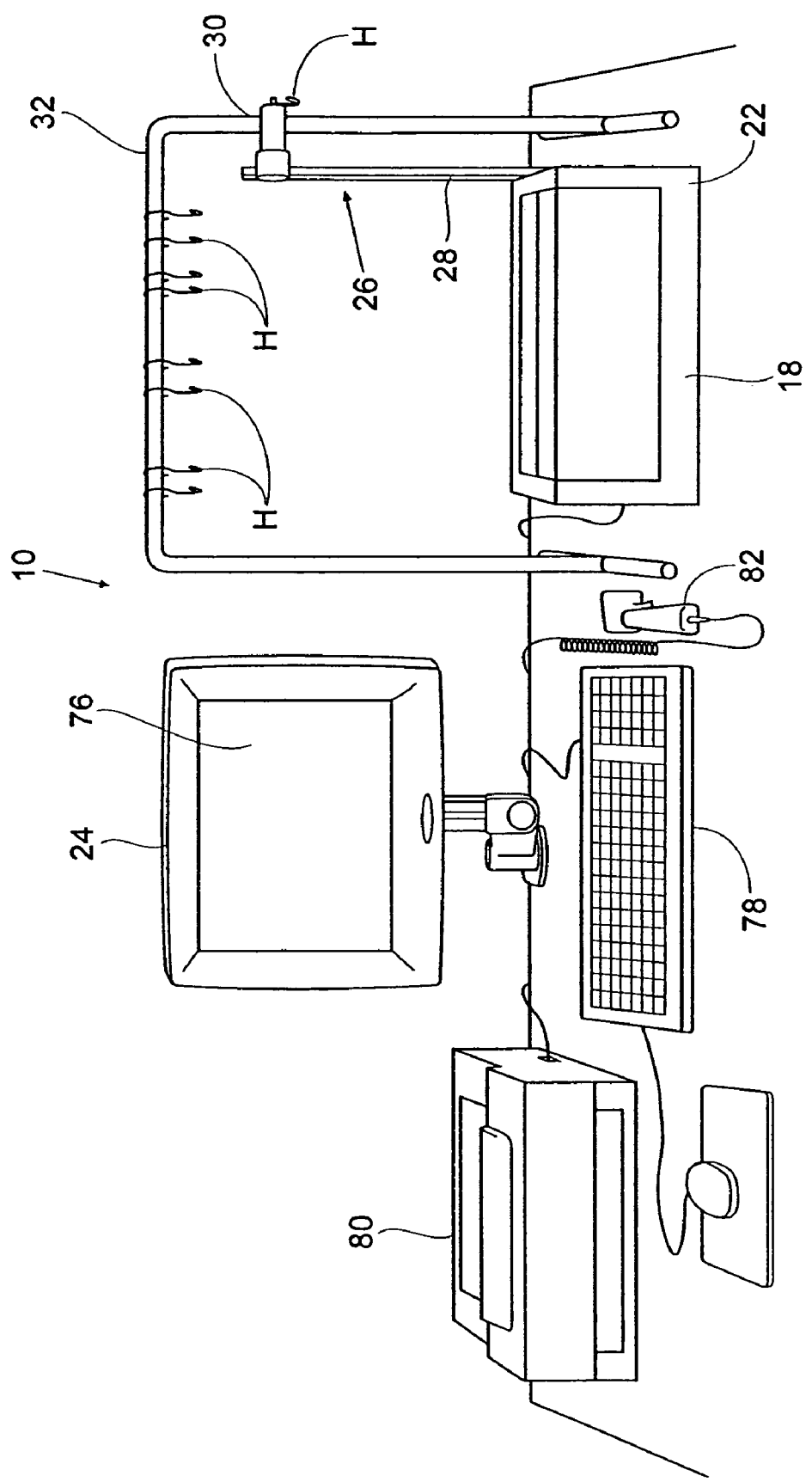
FIG. 1 is a perspective view of a pharmaceutical compounding system that includes a compounding device that, in use, mixes or compounds two or more selected liquids and/or drugs intended to be administered to a human being or an animal.

FIG. 1 shows a pharmaceutical compounding system 10. The system 10 can be used for mixing or compounding two or more selected liquids and/or drugs intended to be administered to a human being or an animal. In use, the system 10 serves to transfer two or more of individual prescribed liquids and/or drugs from multiple source containers (e.g., individual vials, bottles, syringes, or bags) into a single collecting container (e.g., a bottle, syringe, or bag), so that the mix of liquids and/or drugs can be administered (e.g., intravenously) to an individual in need.

As one example, due to injury, disease, or trauma, a patient may need to receive all or some of their nutritional requirements intravenously. In this situation, the patient will typically receive a basic solution containing a mixture of amino acids, dextrose, and fat emulsions, which provide a major portion of the patient's nutritional needs, which is called total parenteral nutrition, or, in shorthand, TPN. In this arrangement, a physician will prescribe a mixture of amino acids, dextrose, and fat emulsions to be administered, as well as the frequency of administration. To maintain a patient for an extended period of time on TPN, smaller volumes of additional additives, such as vitamins, minerals, electrolytes, etc., are also prescribed for inclusion in the mix. Using the system 10, under the supervision of a pharmacist, the prescription order is entered and individual doses of the prescribed liquids, drugs, and/or additives are accordingly transferred from separate individual source containers for mixing in a single container for administration to the individual.

There are other environments where the system 10 is well suited for use. For example, in the medical field, the system 10 can be used to compound liquids and/or drugs in support of chemotherapy, cardioplegia, therapies involving the administration of antibiotics and/or blood products therapies, and in biotechnology processing, including diagnostic solution preparation and solution preparation for cellular and molecular process development. Furthermore, the system 10 can be used to compound liquids outside the medical field.

Nevertheless, for the purpose of explaining the features and benefits of the system 10, the illustrated embodiment describes use of the system 10 in support of TPN.

I. System Overview

The system 10 includes three principal components. These are (i) a liquid transfer set 12 (see FIG. 2A), which, in use, couples a final solution container 14 to individual solution source containers 16; (ii) a compounding or solution mixing device 18 (see FIG. 1), which, in use (see FIG. 3), interacts with the transfer set 12 to transfer liquids from the solution source containers 16 into the final solution container 14; and (iii) a controller 20 (see FIG. 1) that governs the interaction to perform a compounding or solution mixing procedure prescribed by a physician, which is typically carried out by a trained clinician at a compounding site under the supervision of a pharmacist.

The compounding device 18 and controller 20 are intended to be durable items capable of long-term use. In the illustrated embodiment (see FIG. 1), the compounding device 18 is mounted inside a housing or case 22, and the controller 20 is mounted, in most part, within a control panel 24 mounted to a surface outside the case 22. The case 22 presents a compact footprint, suited for set up and operation upon a tabletop or other relatively small surface. The case 22 and panel 24 can be formed into a desired configuration, e.g., by molding or forming. The case 22 and panel 24 are preferably made from a lightweight, yet durable material, e.g., plastic or metal.

The transfer set 12 (FIG. 2A) is intended to be a sterile, single use, disposable item. As FIG. 3 shows, before beginning a given compounding procedure, the operator loads the various components of the transfer set 12 in association with the device 18.

Figure 3:
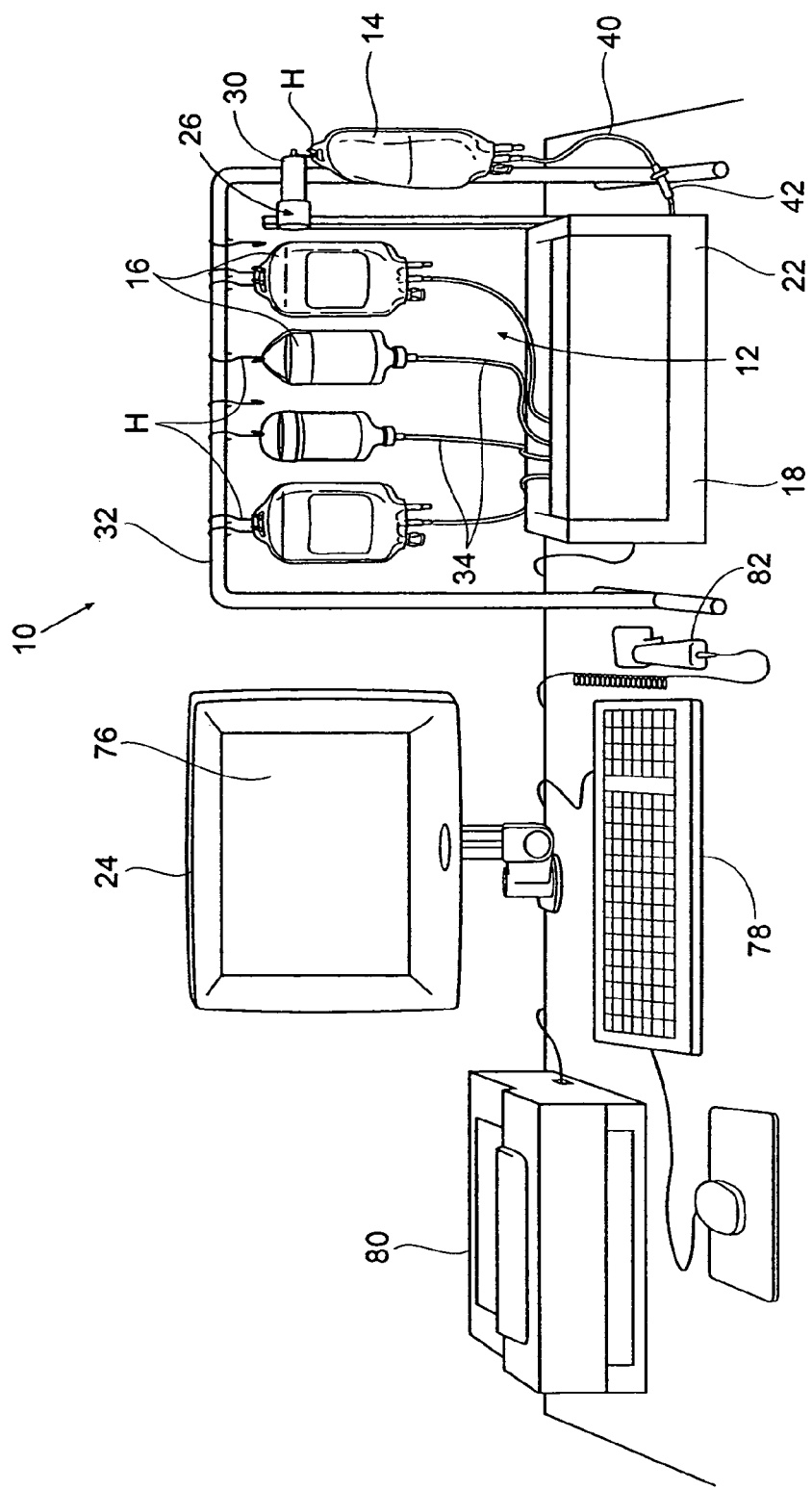
FIG. 3 is a perspective view of the system shown in FIG. 1 with the transfer set shown in FIG. 2A mounted for use on the compounding device.

As illustrated, the device 18 includes a weigh station 26 that, in use, carries the final solution container 14 (as FIG. 3 shows). The weigh station 26 includes a support arm 28, which in the illustrated embodiment, is attached to a side or bottom of the case 22. The weigh station 26 also includes a conventional load cell 30, which suspends from a top of the support arm 28. During compounding, the final solution container 14 hangs from a hanger H on the load cell 30 (see FIG. 3). As also illustrated, the device 18 includes a source solution support frame 32. The support frame 32 carries several individual hangers H, which, during compounding, support the individual source containers 16.

As illustrated, the support frame 32 comprises a separate component; however, the support frame 32 can be attached in a suitable manner to the case 22. Typically, during compounding, the device 18, with source containers 16 and final container 14, are located within a laminar flow hood in a "clean room" environment.

Figure 2A:
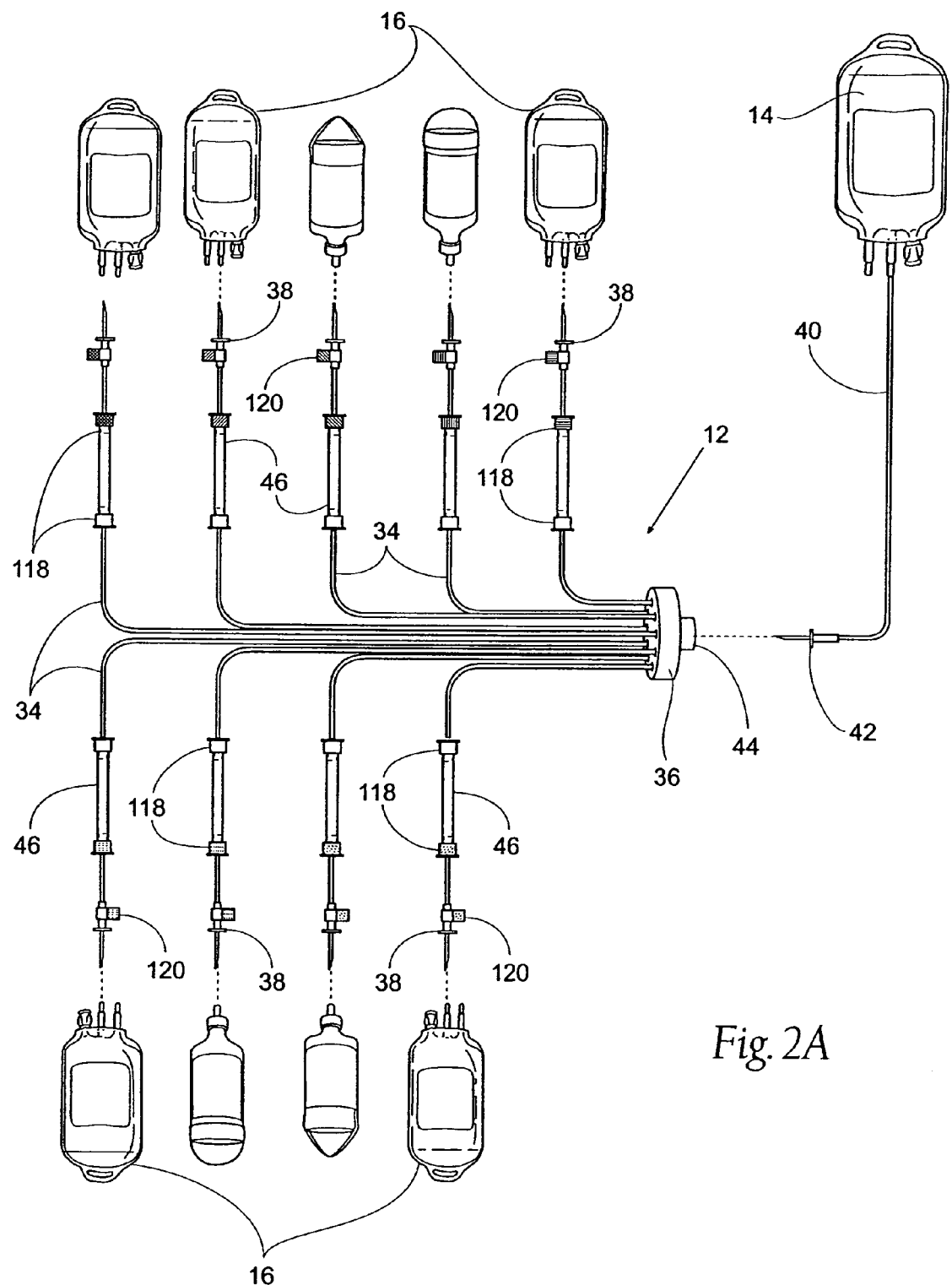
FIG. 2A is a view of a disposable transfer set that can be used in association with the compounding device shown in FIG. 1.

The transfer set 12 shown in FIG. 2A can in general include lengths of source transfer tubing 34, which are joined at one end to a common junction or manifold 36. The opposite ends of the source transfer tubing 34 each includes a spike 38 or suitable releasable coupling, which can be inserted in conventional fashion through a diaphragm carried by the associated source solution container 16, to open flow communication between that source solution container 16 and the respective source transfer tubing 34. A length of final transfer tubing 40 is coupled to the final solution container 14. The opposite end of the final transfer tubing 40 includes a spike 42 or suitable releasable coupling, which can be inserted into an outlet 44 in the manifold 36, to couple the final solution container 14 to the source solution containers 16. The source transfer tubing 34 and the final transfer tubing 40 can be made from flexible, medical grade plastic material, such as polyvinyl chloride plasticized with di-2-ethylhexyl-phthalate. One or more of the source containers 16 or final containers 14 can likewise be made from medical grade plastic material selected for inertness and compatibility with the intended source solution. Likewise, one or more of the source or final containers 16 or 14 can be made from glass.

Each source transfer tubing 34 includes an in-line pump segment 46 between the spike 38 and the manifold 36. The pump segments 34 can be made, e.g., from silicone rubber. Each source transfer tubing 34 also includes an in-line, one way valve 48 (e.g., a duckbill, disk, or umbrella valve)—which, in the illustrated embodiment, is carried within the manifold 36 (see FIG. 2B)—which permits liquid flow from the source containers 16 toward the manifold 36, but prevents backflow from the manifold 36 toward any of the source containers 16. Each valve 48 opens in response to forward fluid flow, to allow liquid flow into the manifold 36 and through the spike-receiving outlet 44 (i.e., toward the final solution container 14). Each valve 48 closes in response to back flow of liquid in the manifold 36 from the outlet 44.

Figure 4:
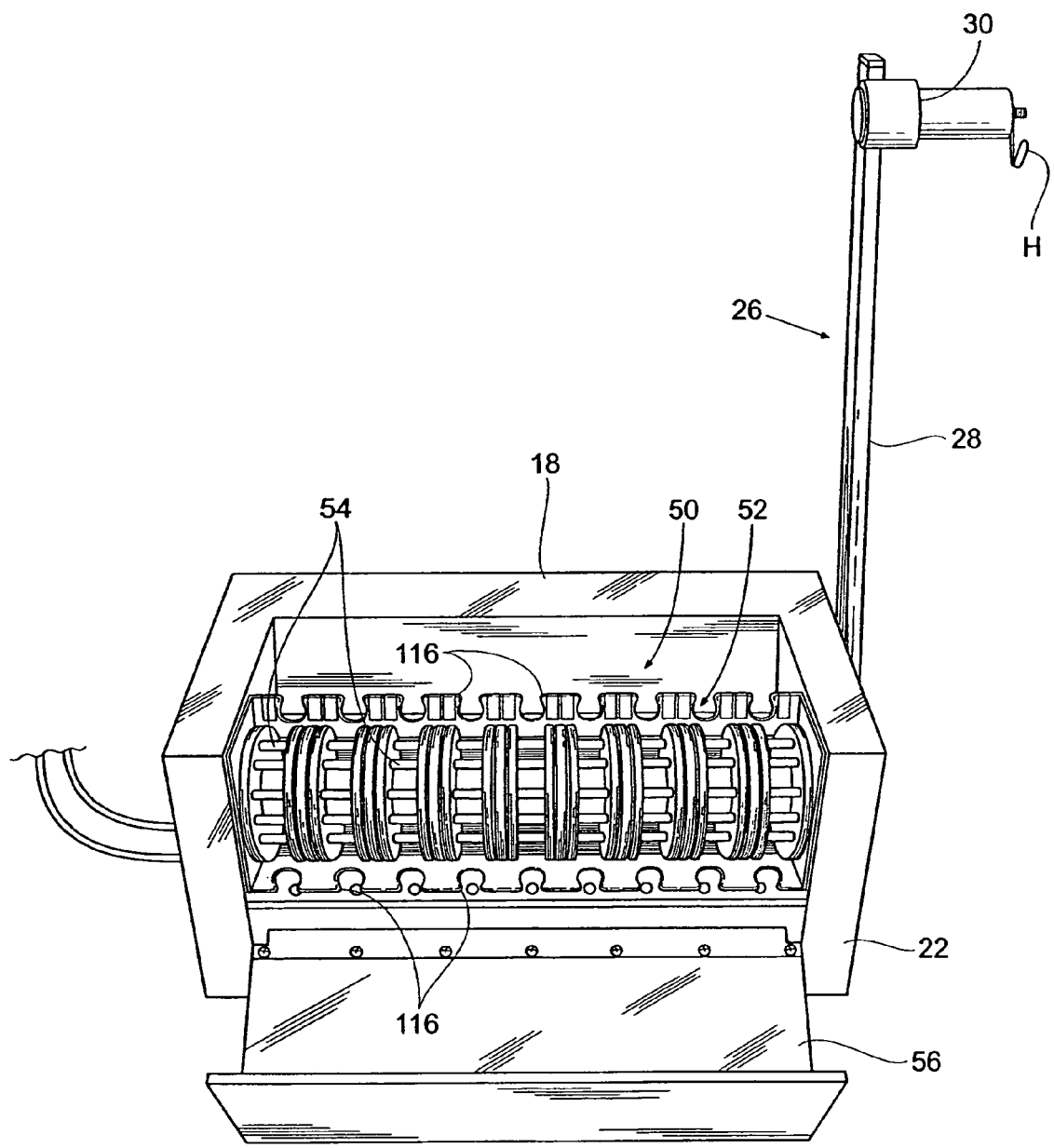
FIG. 4 is a perspective view of the compounding device shown in FIG. 1, with its peristaltic pumping station open for loading a transfer set of the type shown in FIG. 2A.

Each pump segment 46 is designed for use in association with a peristaltic pump rotor. Accordingly, as FIG. 4 shows, the compounding device 18 includes a peristaltic pumping station 50. As FIG. 4 shows, the peristaltic pumping station 50 occupies a pump bay 52 or compartment formed in the device. As shown, the peristaltic pumping station 50 includes an axial array of individual peristaltic pump rotor assemblies 54, although non-axial arrays can be used. Furthermore, the pumping station 50 can includes multiple side-by-side banks of peristaltic pump rotor assemblies 54.

Figure 5:
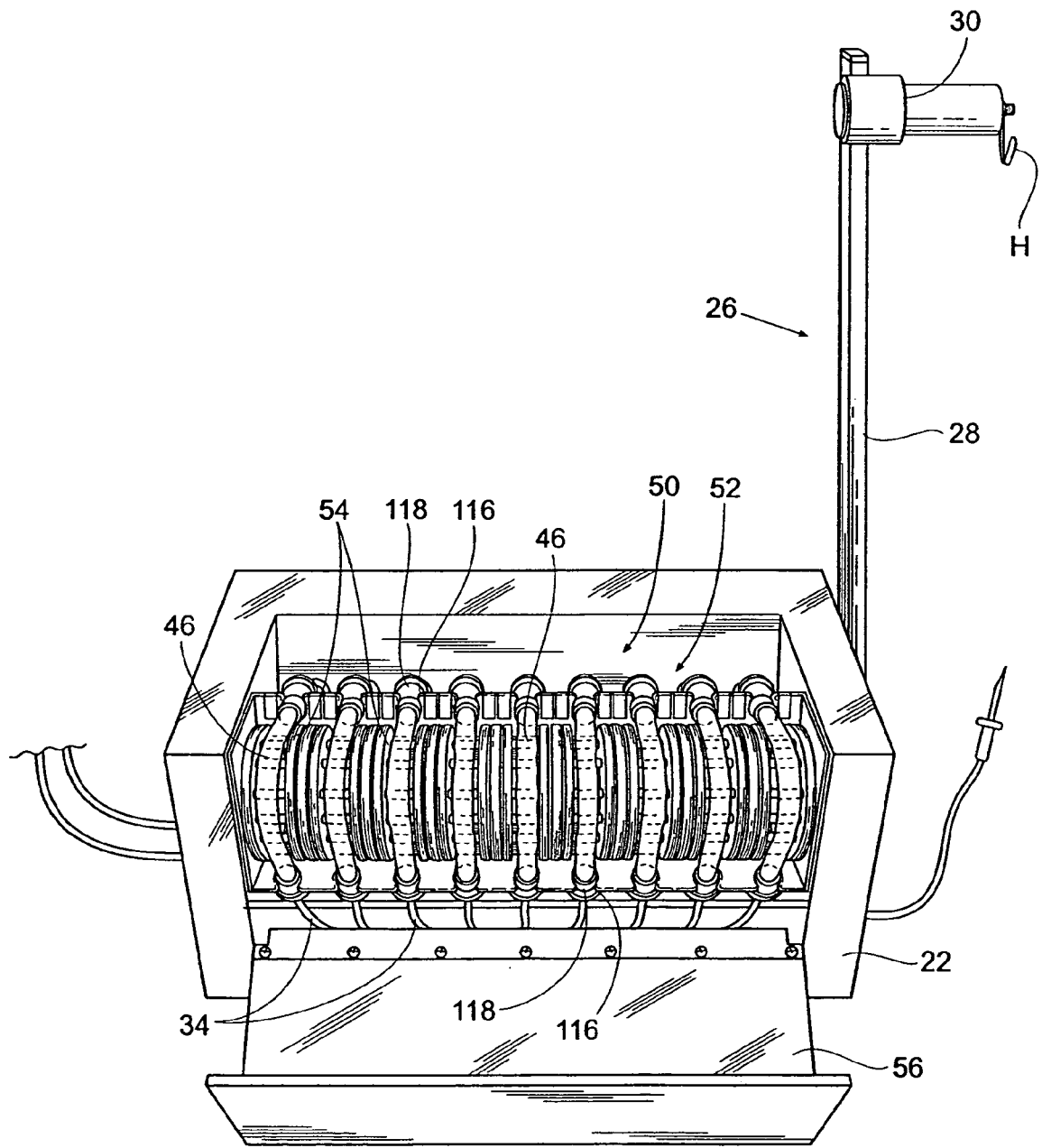
FIG. 5 is a perspective view of a compounding device shown in FIG. 4, with a transfer set mounted in the peristaltic pumping station.

The peristaltic pumping station 50 includes a door 56, which opens and closes the pump bay 52. The door 56 opens (as FIG. 4 shows) to allow loading of a selected one of the pump segments 46 in association with a selected one of the peristaltic pump rotor assemblies 54, as FIG. 5 shows. The door closes (as FIG. 3 shows) to enclose the peristaltic pumping station 50 during operation. Desirably, the controller 20 is coupled to an electrical interlock 66 (see FIG. 13) to prevent operation of the peristaltic pump rotor assemblies 54 when the door 56 is opened.

The controller 20 executes a compounding protocol or procedure based upon prescribed data entry orders and preprogrammed pump control rules, which also can include other input from the operator. During operation, the peristaltic pump rotor assemblies 54 are individually, selectively operated in series—or simultaneously, selectively operated in parallel—as dictated by the controller 20, to transfer desired amounts of source solutions from the individual source containers 16 through the manifold 36 and into the final container 14. The load cell 30 is coupled to the controller 20, to gravimetrically monitor the incremental transfer of the individual source solutions into the final container 14. The controller 20 monitors incremental changes in weight, which are processed according to preprogrammed rule to govern the speed at which a given peristaltic pump assembly 54 is operated and, ultimately, stopped when the prescribed amount of source solution is delivered.

The controller 20 (see FIG. 13) can comprises a main processing unit (MPU) 58. The MPU 58 comprises a conventional PC that is, in the illustrated embodiment, mounted within the control panel 24, outside the case 22 of the compounding device 18. Alternatively, the MPU 58 could be mounted within the case 22 of the compounding device 18. The MPU 58 can comprise one or more conventional microprocessors that support the Microsoft® Windows® operating environment. The MPU 58 includes conventional RAM 122 and a conventional nonvolatile memory device 74, such as a hard disk drive. The MPU 50 includes an input device 124 to upload programs into the memory device 74, e.g., a CD-reader. In the illustrated embodiment, a compounding control manager function 72 resides as process software in the memory device 74 of the MPU 58.

In the illustrated embodiment, the controller 20 also includes a supervisor CPU 126 and peripheral processing unit (PPU) 60. Both the CPU 126 and PPU 60 are desirably implemented on a printed circuit board. The CPU comprises a conventional microprocessor capable of running the uC/OS-II operating system. The PPU is a dedicated microchip PIC, driven by firmware specific to its processing tasks and control functions. In the illustrated embodiment, the CPU 126 and PPU 60 are mounted inside an electronics bay 62 or compartment with the case 22 of the compounding device 18 (see FIGS. 6A, 6B, and 7). An AC power supply (not shown) supplies electrical power to the CPU 126, PPU 60, and other electrical components of the device 18.

Figure 13:
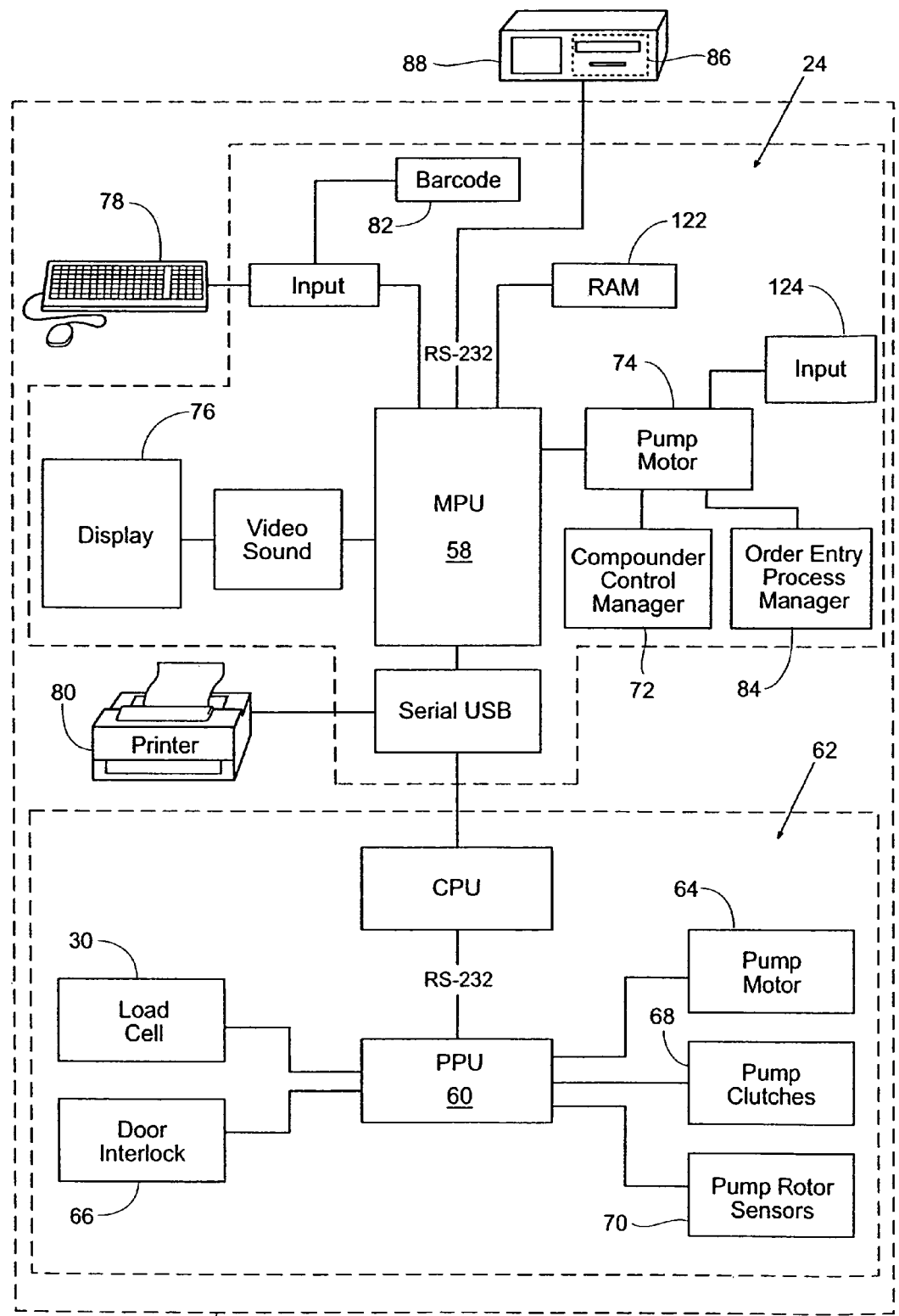
FIG. 13 is a schematic view of a controller that the compounding device shown in FIG. 1 can incorporate, which can execute the compounding control manager and order entry process manager functions shown in FIGS. 9A to 9W; 10A to 10E; 11A to 11I.

The CPU 126 is coupled via a USB, RS-232, or Ethernet port, or other connective means, to the MPU 58 (see FIG. 13). The CPU 126 receives high-level instructions from the MPU 58 generated by the compounding control manager 72. The PPU 60 (see FIG. 13) is coupled via an RS-232 link to the CPU 126. The high-level instructions generated by the compounding control manager 72 are conveyed by the CPU 126 as medium level commands to the PPU 60. The PPU 60 is connected to various hardware of the peristaltic pump station 50 and weigh station 26—e.g., the door interlock 66 (as previously described), a pump motor 64 (see also FIG. 6A, as will be described later), pump clutches 68 (a will be described later), Hall effect pump rotor sensors 70 (as will also be described later), the load cell 30 (previously described), etc. The PPU 60 provides hardware-specific commands, based upon the medium level control commands generated by the CPU 126, as well as a first level of safeguards (e.g., to stop the pump motor 64 if the door 56 is open, as previously described). The PPU 60 and CPU 126 communicate with and monitor each other, to backup individual failures and take corrective action.

The compounding control manager 72 function 72 resides on the MPU 58. The compounding control manager 72 includes preprogrammed rules that prescribe procedures for receiving and manipulating input data, monitoring device status and operating conditions, outputting or storing data, and commanding operation of the peristaltic pump station 50 to achieve prescribed compounding tasks. The MPU 58 communicates high level instructions to the CPU 126 (e.g., the amount of liquid each peristaltic pump assembly 54 is to convey), which are created by the compounding control manager 72 in response to operator input. The CPU 126, in turn, communicates medium level instructions to the PPU 60, which communicates specific pump commands to the peristaltic pump assemblies 54 to carry out the pumping instructions, well as receives and evaluates operational status data from sensors and the load cell, to generate closed-loop feedback control and corresponding alarms. The PPU 60 also relays operational status data to the CPU 126, which also evaluates the operational status data in parallel with the PPU 60. In this respect, the CPU 126 provides a second level of safeguards if an alarm condition is not detected by the PPU 60 (e.g., to halt pumping if over-delivery—not otherwise sensed by the PPU 60—is occurring).

In the illustrated embodiment (see FIG. 1), the controller 20 includes a display device 76, which is part of the control panel 24, data entry devices 78 (e.g., a keyboard and a mouse), and a data output station 80 (e.g., a printer), which are coupled via appropriate inputs and outputs to the MPU 58. In the illustrated embodiment (see FIG. 1), the display device 76 also desirably serves as another data entry device using, e.g., conventional touch screen methodologies implemented by the compounding control manager 72 using a Windows®-based operating platform resident in the compounding control manager 72. The combined data display and data entry capabilities that the compounding control manager 72 executes in this arrangement provide an interactive user interface on the display device 76 that, under preprogrammed rules resident in the compounding control manager 72, accepts data entry and displays for the operator information prompting or confirming the entered data, as well as monitored operational status and conditions of the compounding device 18. The compounding control manager 72 also provides a third level of safeguards by verification of the original order with the actual pump delivery results. The display can be in alpha-numeric format and/or as graphical or pictorial images, as desired. The compounding control manager 72 also enables output of selected information to the printer 80 in a desired format, e.g., as activity reports. The interactive user interface of the compounding control manager 72 allows the operator to conveniently enter, view, and assimilate information regarding the operation of the system 10. Further details of the compounding control manager 72 and the touch screen interactive user interface that can be implemented by the compounding control manager 72 will be described later.

As also shown in FIG. 1, the MPU 58 also includes an input for a bar code reader 82 or the like, for scanning information into the compounding control manager 72. Further details of this aspect of the system 10 will be described later.

As FIG. 1 also shows, the MPU 58 also includes input for keyboard and mouse data entry devices 78. These devices 78 allow the operator to enter data for manipulation by the compounding control manager 72 and to interact with information presented by the display device 76 in different ways, and without use of the touch screen data entry capabilities of the compounding control manager 72. In this arrangement (see FIG. 13), the controller 20 desirably includes an order entry process manager 84, which can reside on the memory device 74 of the MPU 58 in the control panel 24. The order entry manager 84 makes possible other forms of interactive data entry and data viewing platforms, as well as other forms of data output to the printer 80 in a selected format, e.g., as labeling for the final solution container 14, as will be described in greater detail later.

Desirably (as FIG. 13 shows), the order entry process manager 84 can be accessed by browser software 86 residing on one or more external microprocessors 88 linked to the compounding control manager 72 of the device controller 20. In this arrangement, the controller 20 desirably includes an RS-232 link or another alternative data communication connections (e.g., radio, microwave, infrared, or other electromagnetic wave communication systems), to enable electronic or electromagnetic data communication between the compounding control manager 72 and external input or output devices (e.g., other data entry workstations and/or printers), using, e.g., single-station hubless local area network connections, multiple-station hub or switch local area network connections, multiple-station hub connections with facility network servers, and/or multiple-station connections through the public internet. Conversely, or in addition, multiple compounding devices 18 can be linked through their onboard controllers to multiple data entry workstations or sites. These capabilities of the controller 20 make diverse arrangements of fully networked pharmaceutical compounding possible. Further details of these networked forms (e.g., internet, intranet, or loopback) of interactive data entry and data viewing platforms, that can be accommodated by the controller 20 in association with the compounding control manager 72, will be described later.

Upon completing a compounding procedure, the operator seals the inlet tubing 40 of the final solution container 14 and detaches the final transfer tubing spike 42 from the manifold 36. When there are a series of compounding orders that require mixtures of at least some of the same source solutions, which typically is the case, the operator will proceed to the next compounding order by attaching the spike 42 of the inlet tubing 40 of a new final solution container 14 to the manifold 36 and executing another compounding procedure. Otherwise, the operator can decouple the source transfer tubing 34 from the source containers 16 and remove the transfer set 12 and source containers 16 from association with the device 18. The transfer set 12 can be discarded. Each final solution container 14, and its compounded liquid contents, is retained for storage, infusion, transfusion, or further processing.

II. Technical Features of the Compounding Device

Figure 6A:
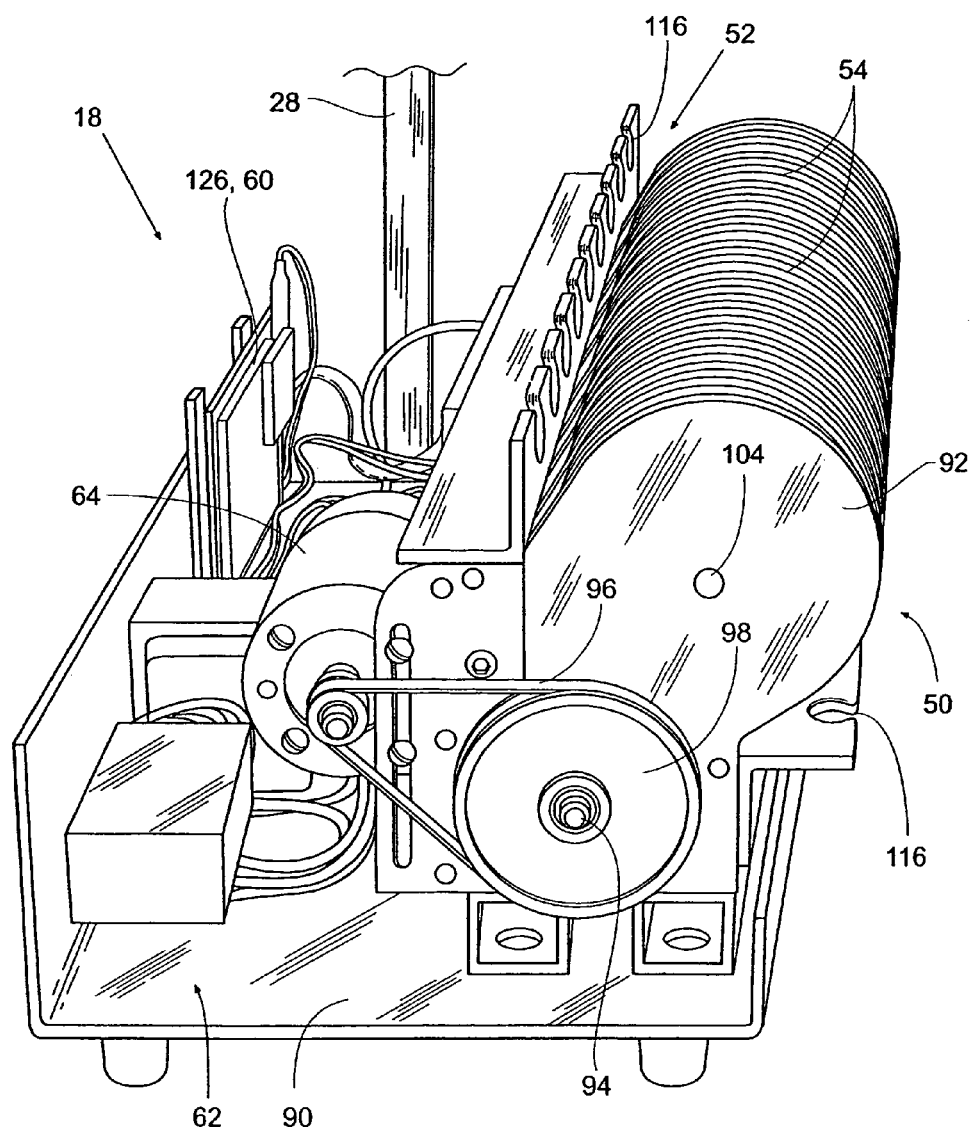
FIG. 6A is a perspective side view of the compounding device shown in FIG. 4 with its exterior case removed to show the peristaltic pump components and other internal components.
Figure 6B:
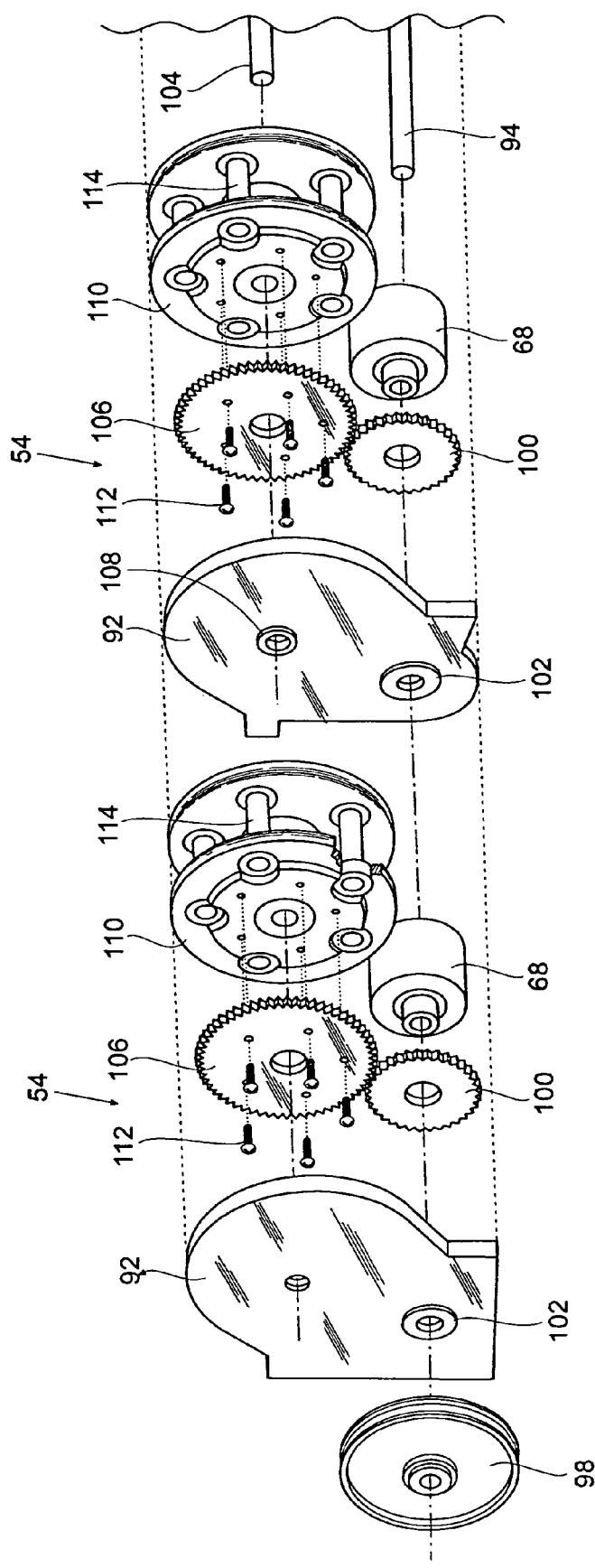
FIG. 6B is an exploded perspective view of the peristaltic pump components shown in FIG. 6A.
Figure 7:
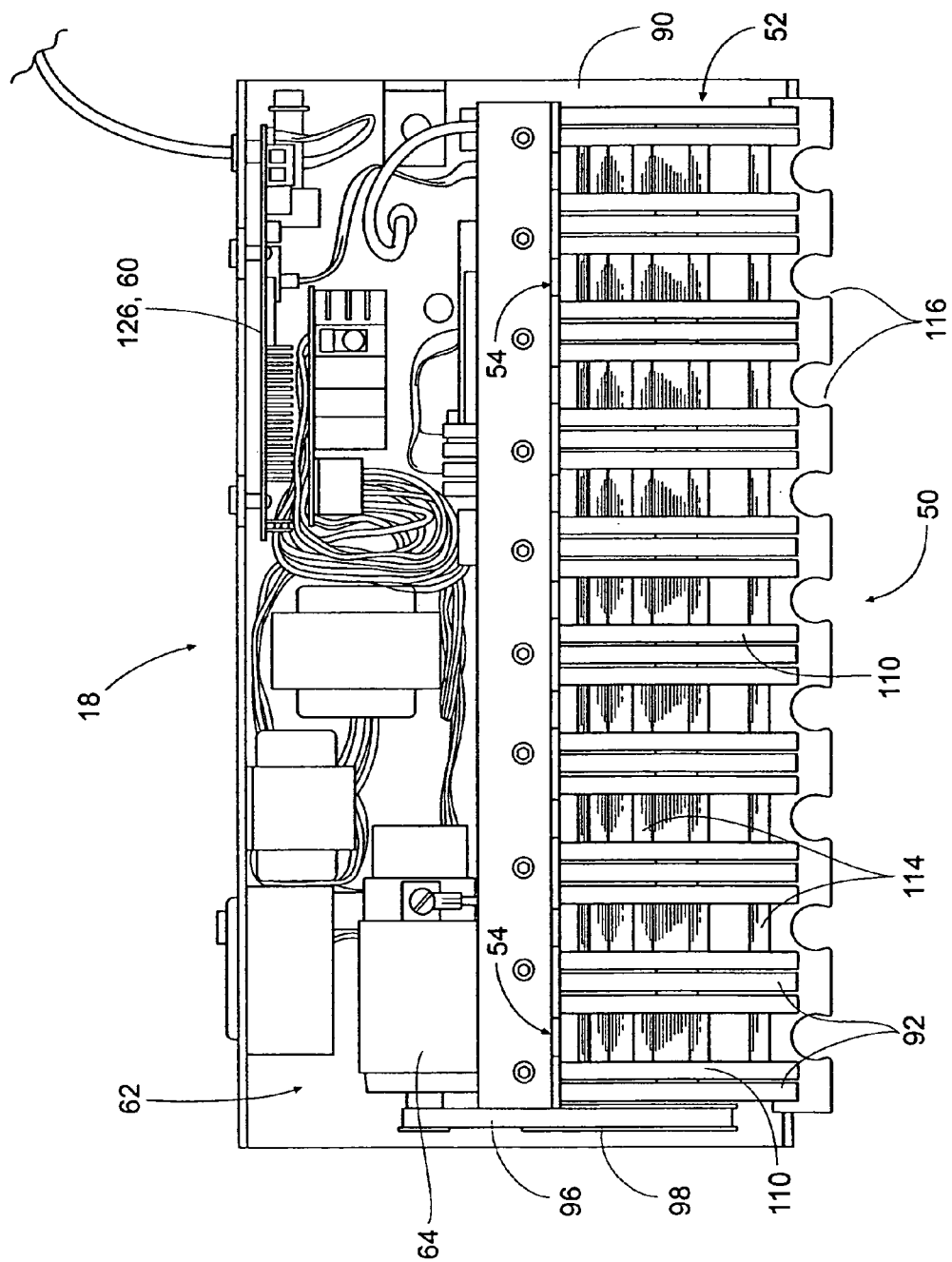
FIG. 7 is a top view of the compounding device shown in FIG. 6A.

FIGS. 6A, 6B, and 7 best show the details of construction of a representative embodiment of the compounding device 18. As illustrated, the device 18 includes a frame 90 that is divided into the pump bay 52 and the electronics bay 62, as previously described. Hardware components of the peristaltic pumping station 50 occupy the pump bay 52. The electrical components of the pumping station 50 and the load cell 30, as well as the PPU 60, occupy the electronics bay 62. The case 22 shown, e.g., in FIGS. 4 and 5, encloses the frame 90 and the components it carries.

A. The Peristaltic Pumping Station

Within the pump bay 52, the peristaltic pumping station 50 includes an array of peristaltic pump rotor assemblies 54, as already generally described. The number and configuration of peristaltic pump rotor assemblies 54 can vary according to design considerations and the compounding requirements of the device 18. In the illustrated embodiment (shown in FIG. 4), there are nine peristaltic pump rotor assemblies 54.

As illustrated (see FIGS. 6A and 6B), each peristaltic pump rotor assembly 54 is constructed in the same manner. Each assembly 54 is supported on a bearing plate 92 secured to the frame 90. The bearing plates 92 are arranged sequentially in an axial spaced relationship along a drive shaft 94. The drive shaft 94 is coupled at one end to the electric drive motor 64 (see FIG. 6A) (carried in the electronics bay 62) via a drive belt 96 and drive pulley 98. Alternatively, the drive shaft 94 can be coupled directly to the drive motor 64. Operation of the drive motor 64, which is governed by the controller 20, rotates the drive shaft 94 at a desired rate of rotation. In a representative implementation, the drive motor can rotate the drive shaft 94 at variable rates. Each pump rotor assembly 54 includes a drive gear 100, which is carried by a bearing 102 on the drive shaft 94. A conventional electromagnetic clutch assembly 68 is coupled to each drive gear 100. Each clutch assembly 68 is individually coupled to the controller 20 (as FIG. 13 shows). When actuated by the controller 20, a given clutch assembly 68 frictionally couples the drive gear 100 to the drive shaft 94, causing rotation of the drive gear 100. When the clutch assembly 68 is not actuated by the controller 20, rotation of the drive shaft 94 is not imparted to the associated drive gear 100.

A fixed idler shaft 104 extends through the bearing plates 92, spaced from and offset from the drive shaft 94. Each pump rotor assembly 54 also includes a driven gear 106 carried on a bushing 108 on the idler shaft 104. The driven gears 106 are individually coupled to the drive gears 100, such that rotation of a given drive gear 100 will impart rotation to its respective driven gear 106. In this arrangement, each pump rotor assembly 54 includes a pump rotor 110 coupled (e.g., by gear attachment screws 112) for rotation with each driven gear 106. Each pump rotor 110 carries an array of pump rollers 114, which, in use, engage an in-line pump segment 46 of the transfer tubing 34.

Actuation of a given clutch assembly 68 by the controller 20 couples the associated drive gear 100 to the drive shaft 94—to which rotation is imparted by the drive motor 64—which, in turns, imparts rotation through the driven gear 106 to the associated pump rotor 110. During rotation of the pump rotor 110, the pump rollers 114 engage the associated pump segment 46 and convey liquid through the transfer tubing 34 by well-understood peristaltic pumping action.

Each pump rotor assembly 54 includes a pair of holding brackets 116 aligned with the associated pump rotor 110. The holding brackets 116 are sized and configured to releasably mate with mounts 118 (see FIG. 2A) formed on opposite ends of each pump segment 46. The holding brackets 116 frictionally engage the pump segment mounts 118, and thereby hold the pump segments 46 in desired operative association with the pump rollers 114 during use, as FIG. 5 shows.

As will be described in greater detail later, the holding brackets 116 of the pump rotor assemblies 54 and pump segment mounts 118 of the transfer tubing 34 are desirably uniquely coded (e.g., by matching numbers and/or by a matching color or the like) to prompt a desired order to the mounting of a selected pump segment 46 in relation to a selected pump rotor 110. The unique matching code is also carried by the spike 38 of the associated transfer tubing 34 (e.g., by a numbered, colored tab 120), to prompt a desired coupling of the transfer tubing 34 in relation to a selected source container 16. As will be described in greater detail later, the graphics of the user interface generated by the compounding control manager 72 desirably incorporates this unique code, thereby matching the disposable components of the transfer set 12 with the hardware components of the pump station 50, as well as with the desired software functionality provided by the compounding control manager 72.

Desirably, the unique matching code includes bar-code indicia, e.g., one or two-dimensional bar code. In this arrangement, the compounding control manager 72 can require the operator to perform the physical act of scanning in bar code indicia on a solution container and on the transfer set, to eliminate potential error sources prior to compounding. This marriage between software, hardware, and disposable components minimizes sources of compounding errors due to human error.

Figure 2B:
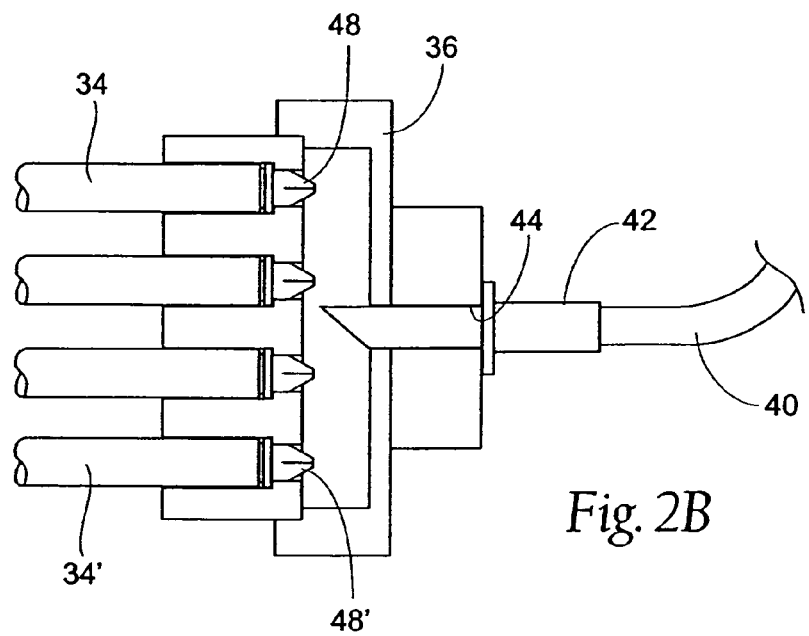
FIGS. 2B and 2C are enlarged views, partially broken away and in section, of an embodiment of a manifold that the transfer set shown in FIG. 2A can incorporate to mediate against lipid hazing.
Figure 2C:
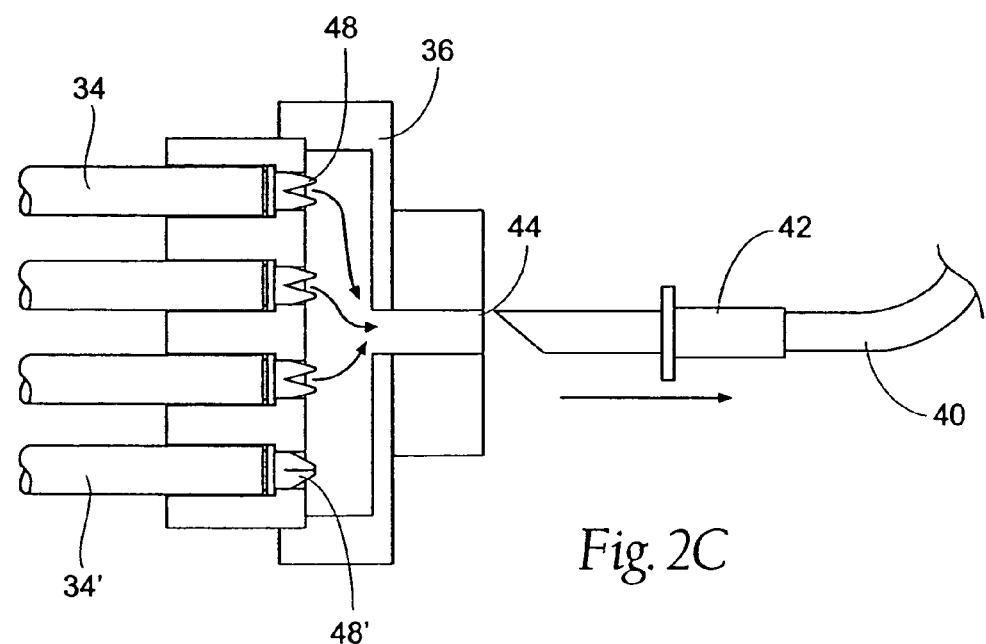
Figure 2D:
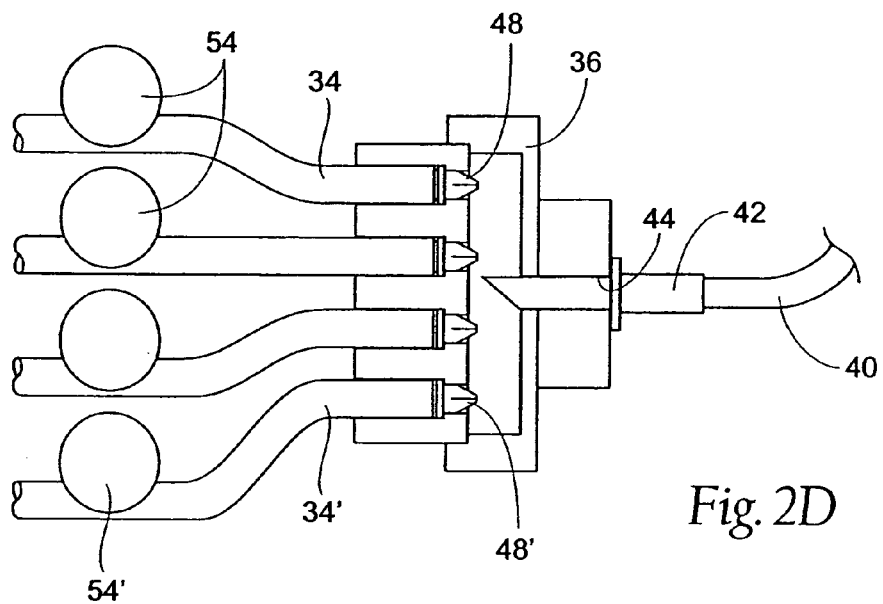
FIGS. 2D and 2E are enlarged views, partially broken away and in section, of another embodiment of a manifold that the transfer set shown in FIG. 2A can incorporate to mediate against lipid hazing.
Figure 2E:
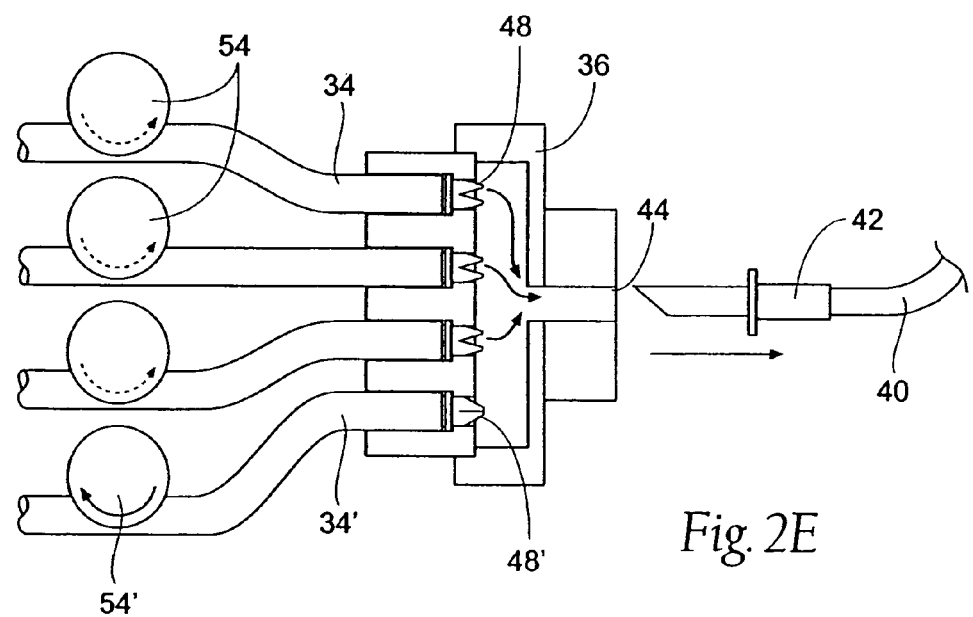
Figure 2F:
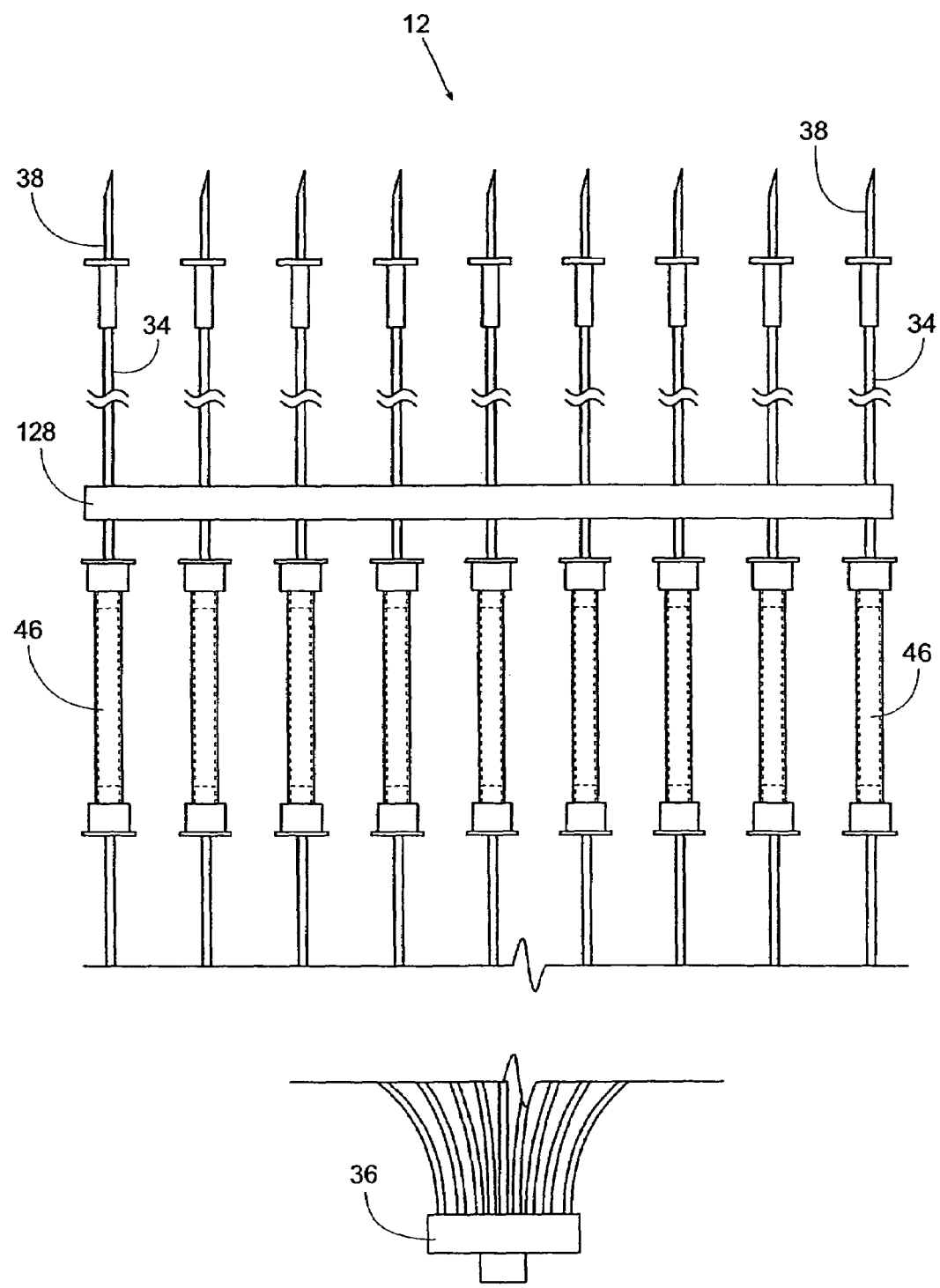
FIG. 2F is a view of a portion of the disposable transfer set shown in FIG. 2A, which includes a transfer tube organizer to facilitate use of the transfer set with the compounding device shown in FIG. 1.

As shown in FIG. 2F, the transfer set 12 can also include a tubing organizer 128, which comprises a molded or fabricated strip of plastic sized and configured to capture, as a unit, all the transfer tubing 34 between the pump segments 46 and the spikes 38 in a desired order. In this arrangement, the organizer 128 requires the operator to mount the pump segments 46 as a unit to the holding brackets 116, with the order of the transfer tubing 24 with respect to the pump rotor assemblies 54 preordained by the organizer 128. The organizer 128 further assures that the transfer tubing 34 is loaded in a desired order on the compounding device 18.

The system 10 makes possible systematic process control at every stage of the compounding process, starting at the physician order point and continuing through compounding and final product delivery and receipt. As above described, orders can be received from the patient site via hospital based electric ordering systems. Upon the electronic receipt of data, such data can be entered or transmitted electronically into the compounding control manager 72. Final solution containers 14 can be labeled automatically as the step preceding the compounding process. The compounding process can thereafter be controlled and verified through labeling on the final solution container 14 in combination with source container labeling and bar coding.

B. Pump Control Criteria

As has been generally described, and as will be described later in greater detail, a desired compounding order is entered by an operator, and the compounding control manager 72 in the MPU 58 of the control panel 24 executes the compounding order. Typically, the compounding order identifies the source solutions and the amounts of each source solution (by weight or volume) that are to be mixed in the final solution. The compounding control manager 72 can operate the individual pump rotor assemblies 54 (through the PPU 60 in the compounding device 18) in a serial compounding mode, i.e., operating a first pump rotor assembly 54 to convey the desired amount of a first source solution into the final container 14, then next operating a second pump rotor assembly 54 to convey the desired amount of a second source solution into the final container 14, and so on until the desired amount of each source solution has been delivered to comprise the desired mixture.

In controlling the individual pump rotor assemblies 54, the preprogrammed rules of the compounding control manager 72 desirably take into account pre-established delivery accuracy criteria. The criteria can vary according to the compounding tasks to be accomplished. For example, for TPN, delivery accuracy criteria can be established of +/−5%, or better, for any ingredient of 0.2 mL or more. A delivery accuracy criteria of +5%/−0% could be established to eliminate the possibility of underfills.

The preprogrammed rules of the compounding control manager 72 also desirably include a delivery time criteria that takes into account the delivery volume. Keeping absolute errors as small as possible is mandated at smaller delivery volumes to achieve a system delivery accuracy goal of +/−5% or better. Such smaller absolute delivery errors require the compounding control manager 72 to incorporate tighter process control, which, for smaller delivery volumes, can result in longer delivery times per mL of delivery. However, larger absolute errors are acceptable at larger delivery volumes to achieve a system delivery accuracy goal of +/−5% or better. For example, a 1% error on a 10 mL delivery is 0.1 mL. The same 1% error on a 1000 mL delivery is 10 mL. Thus, the compounding control manager 72 can institute different process control for larger volumes, which, for larger delivery volumes, can result in a faster delivery times per mL of delivery.

The compounding control manager 72 can also accommodate parallel processing of the same source solution. For example, if the same source solution is present on two pump rotor assemblies 54, both source solutions can be pumped in parallel (at the same time) to shorten overall delivery time. Thus, if it takes two minutes to fill a single container using serial compounding (i.e., one solution after the other), it is expected that parallel compounding can potentially reduce this time requirement down to one minute, depending upon the solution components that comprise the final product.

The preprogrammed rules of the compounding control manager 72 institute desirable closed-loop control of the pump drive motor 64. The close-loop control desirably implement convention proportional-integral-derivative (PID) control schemes to control pump speed to achieve a desired target delivery. The PID control schemes generate pump correction commands that take into account not only the absolute difference between the present delivery amount and the target amount, but also the how quickly the absolute difference is changing over time. The control schemes can use a purely mathematical PID model, or they can incorporate "fuzzy logic" techniques, making use of estimations and interpolations to determine how to adjust the motor speed to obtain the desired flow rate. Use of fuzzy logic techniques permit a motor speed control function without use of multiply and divide instructions, thereby minimizing processing complexity.

In one representative implementation, the compounding control manager 72 conducts a high speed flow rate control regime until the absolute difference between the volume delivered and the target approaches a preset amount. At this "slow down" point, the compounding control manager 72 ramp-downs the flow rate and conducts a low speed flow rate control regime. During this regime, the correction commands become successively smaller as the difference between the volume delivered and the target diminishes. The rate of the flow rate reduction during this regime can be linear or non-linear, and the slope of the non-linear reduction can be either concave, or convex, or a combination thereof.

In a desired implementation, the compounding control manager 72 steps or pulses the respective pump rotor assembly as the target volume is approached. In this arrangement, the PPU 60 can communicate with rotor rotation sensors 70, so that a rotor revolution can be correlated with a number of incrementally sensed steps, which, in turn, can be correlated with incremental degrees of rotor rotation—e.g., one full revolution (360 degrees) equals five hundred incrementally sensed steps, so each incrementally sensed step equals 0.72 degrees of rotation. In this way, the PPU 60 can generate very precise pump commands in terms of small incremental units of pump rotor rotation when the target volume is approached, to prevent an overfill.

III. Technical Features of the Transfer Set

As before described, for a typical compounding session, there are usually a series of compounding orders that require mixtures of at least some of the same source solutions. In this arrangement, an operator will repeatedly exchange final solution containers 14 with the same manifold 36.

In these circumstances, a compounding order that requires a fat emulsion as a source solution can leave a fat emulsion residue in the manifold 36. This residue left in the manifold 36, although small in volume, can be introduced into the final solution container 14 of a subsequent compounding order, which may not specify a fat emulsion. The unintended residue causes what is generally called "lipid hazing" in the final solution container 14 of a compounding order that is supposed to be free of a fat emulsion.

To minimize the lipid hazing effect, in FIG. 2B, there is one transfer tubing 34' that is intended, during use, to be dedicated to the conveyance of a fat emulsion. As before explained, a unique coding arrangement, coupled with required bar code scanning, can be incorporated to assure that this transfer tubing 34' is dedicated during use to the conveyance of fat emulsion from a source container. During compounding, fat emulsion is conveyed into the final solution container 14 in advance of the other source solutions.

Thus, the compounding of other source solutions after the fat emulsion serves to flush residual fat emulsion from the manifold 36 and into the final solution container 14.

Following compounding, when the spike 42 is withdrawn from the outlet 44, a temporary vacuum is created within the manifold 36. The valves 48 can open in response to the temporary vacuum created by withdrawal of the spike 42 from the outlet 44, drawing a small bolus of source solutions into the manifold 36. A residue of fat emulsion can be included in this bolus.

In the illustrated arrangement, the valve 48' in the manifold 36 that is in-line with the fat emulsion transfer tubing 34' is sized and configured to have a valve opening or "cracking" pressure that is greater than the valve opening or cracking pressure of the other valves 48 in the manifold 36, which are in-line with transfer tubing 34 that is not coupled to a fat emulsion source container. The greater cracking pressure of the valve 48' that is in-line with the fat emulsion transfer tubing 34' is selected to keep the valve 48' closed when the spike 42 is withdrawn from the outlet 44.

In use (as FIG. 2C shows), when a spike 42 is withdrawn from the outlet 44, due to the lesser cracking pressures of the valves 48 that are not in-line with the fat emulsion transfer tubing 34', these valves 48 can open in response to the temporary vacuum created by withdrawal of the spike 42 from the outlet 44. However, due to the greater cracking pressure of the valve 48' that is in-line with the fat emulsion transfer tubing 34', the valve 48' remains closed when the spike 42 is withdrawn from the outlet 44. Thus, as the spike 42 is withdrawn and the temporary vacuum is created within the manifold 36, the small bolus of source solutions from all the source containers that may be drawn into the manifold 36 will not include the fat emulsion. Thus, a residue of fat emulsion is prevented from entering the manifold 36 when the final solution container 14 is exchanged.

In an alternative arrangement (see FIGS. 2D and 2E), the peristaltic pump rotor assembly 54' serving the one transfer tubing 34' dedicated to the conveyance of fat emulsion can be capable of reverse rotation under the direction of the controller 20. Reverse rotation creates a negative pressure and draws the in-line valve 48' closed. In this arrangement, the controller 20 commands reverse rotation of the fat emulsion pump assembly 54' prior to the operator removing the spike 42 from the outlet 44. As FIG. 2E shows, removal of the spike 42 can open the valves 48, except the valve 48' in the fat emulsion tubing 34', which remains closed due to the counterforce of negative pump pressure. As before described, as the spike 42 is removed, a bolus of source solutions from all the source containers can be drawn into the manifold 36, except for the fat emulsion.

The vacuum created by removal of the spike 42 can be augmented by pulsing the other peristaltic pump rotor assemblies 54 in a forward direction as the spike 42 is withdrawn. In this arrangement, the cracking pressure of the valve 48' serving the fat emulsion transfer tubing 34' need not be different that the cracking pressure of the other valves 48.

IV. Technical Features of the Controller

A. The Compounding Control Manager

The compounding control manager 72 resides in the MPU 58 in the control panel 24. The compounding control manager 72 allows a clinician to enter, view, adjust and offload information pertaining to a given compounding protocol.

In general, the compounding control manager 72 is the program language that provides the operator with real time feedback and interaction with the compounding device through graphic user interface (GUI) elements. The GUI elements, created in a Windows®-based graphical format, display the various inputs and outputs generated by the compounding control manager 72 and allow the user to input and adjust the information used by the compounding control manager 72 to operate the compounding device 18.

To develop the GUI elements, the compounding control manager 72 can utilize certain third party, off-the-shelf components and tools. Once developed, the compounding control manager 72 can reside as a standard window-based software program on a memory device.

Figure 9A:
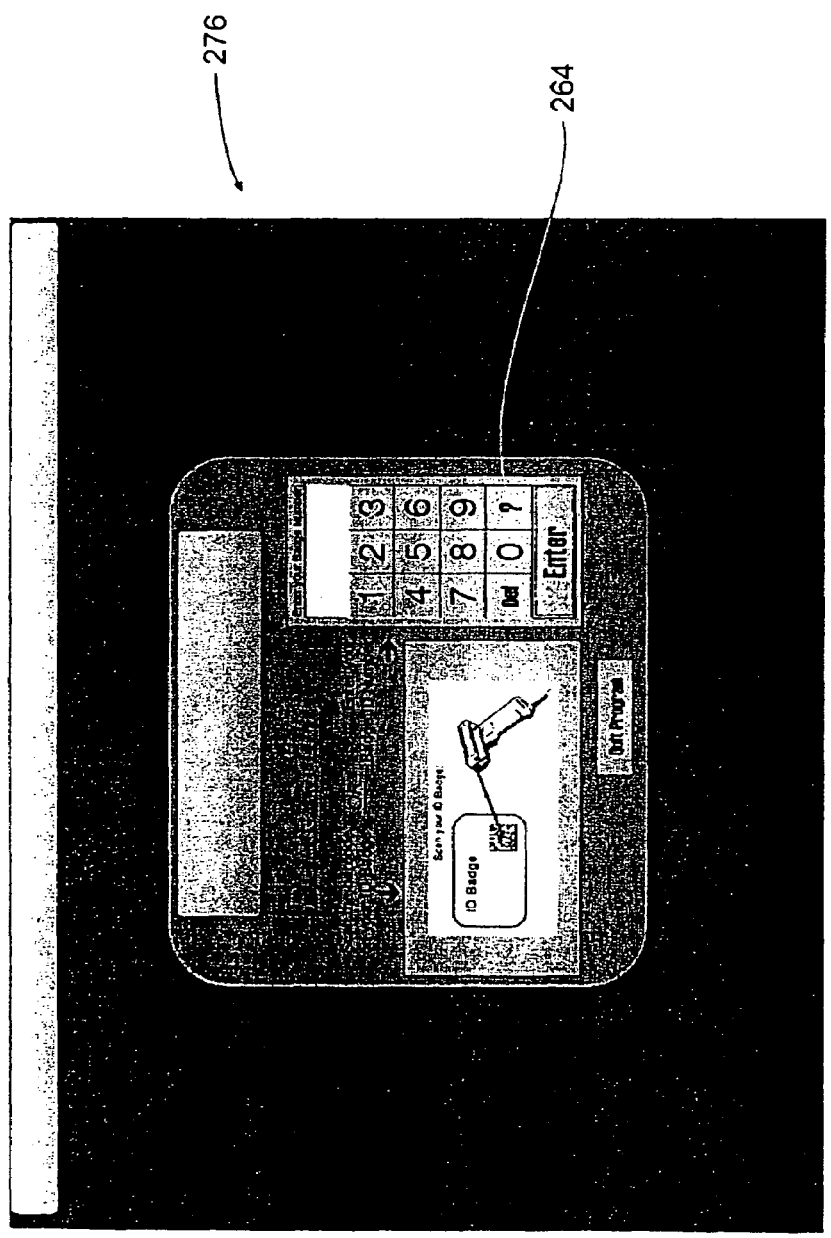
FIGS. 9A to 9W are representative screens of a graphical user interface that a compounding control manager function residing on the compounding device shown in FIG. 1 can generate in the process of enabling and controlling a compounding procedure.
Figure 9B:
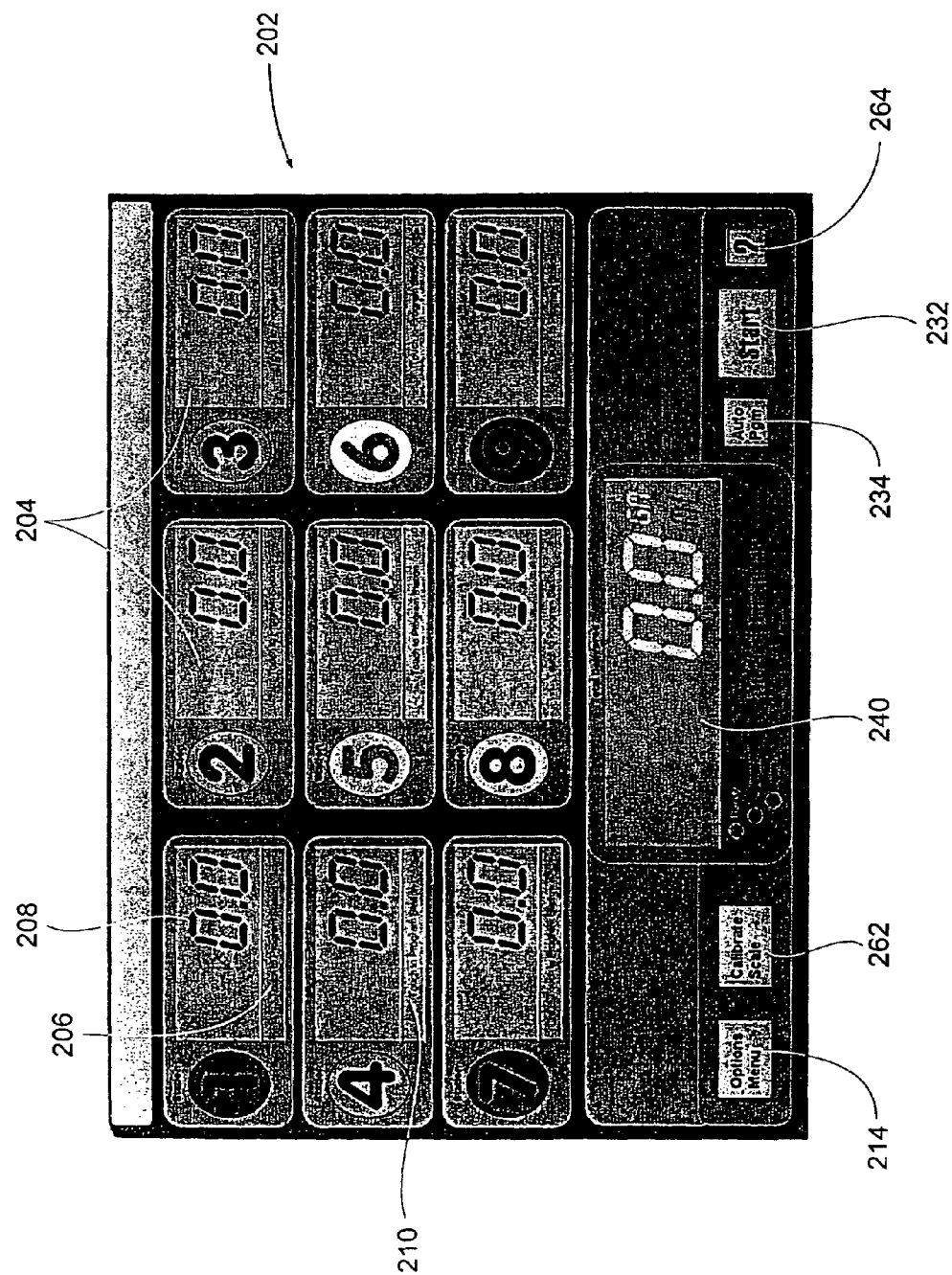
Figure 9C:
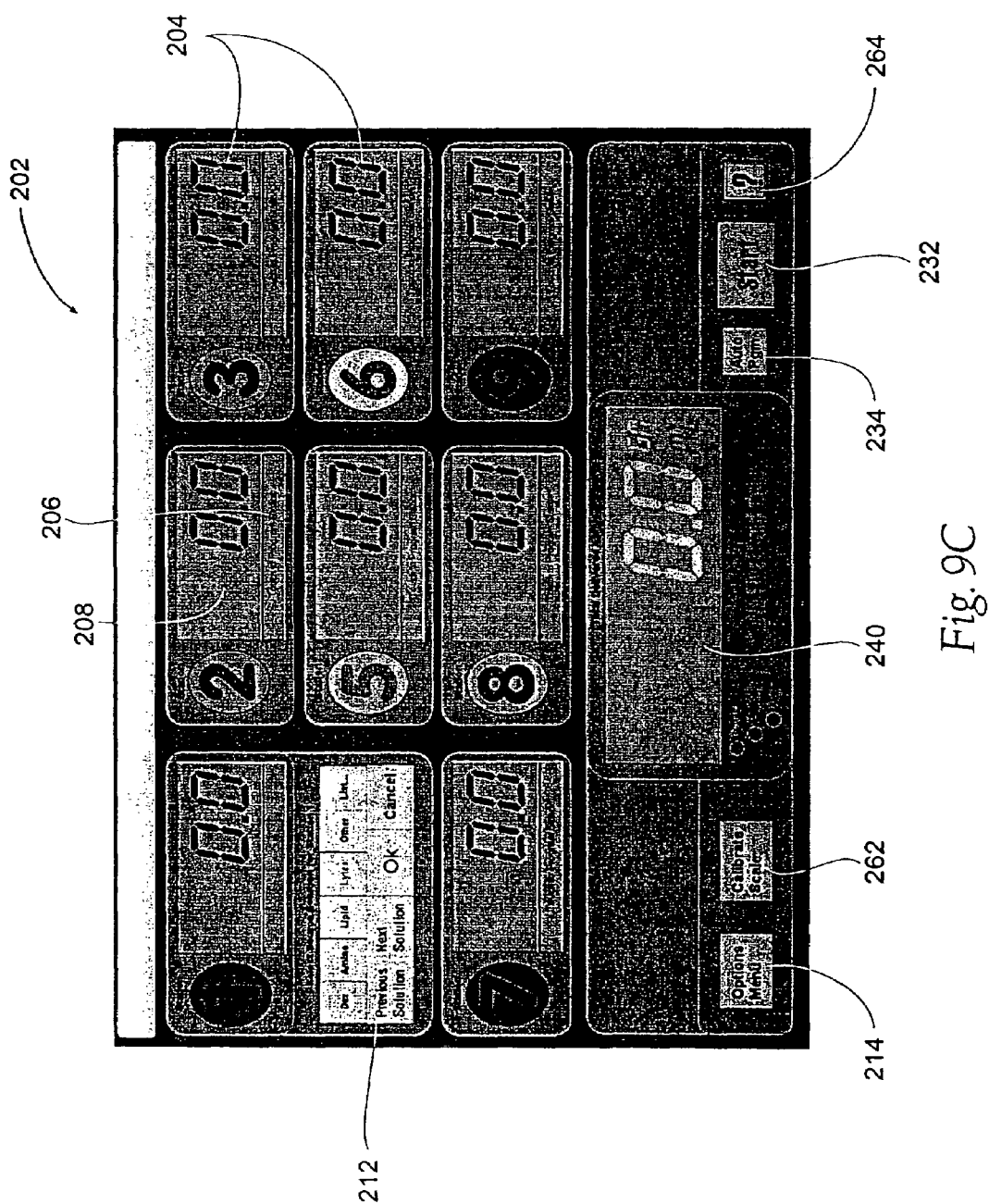
Figure 9D:
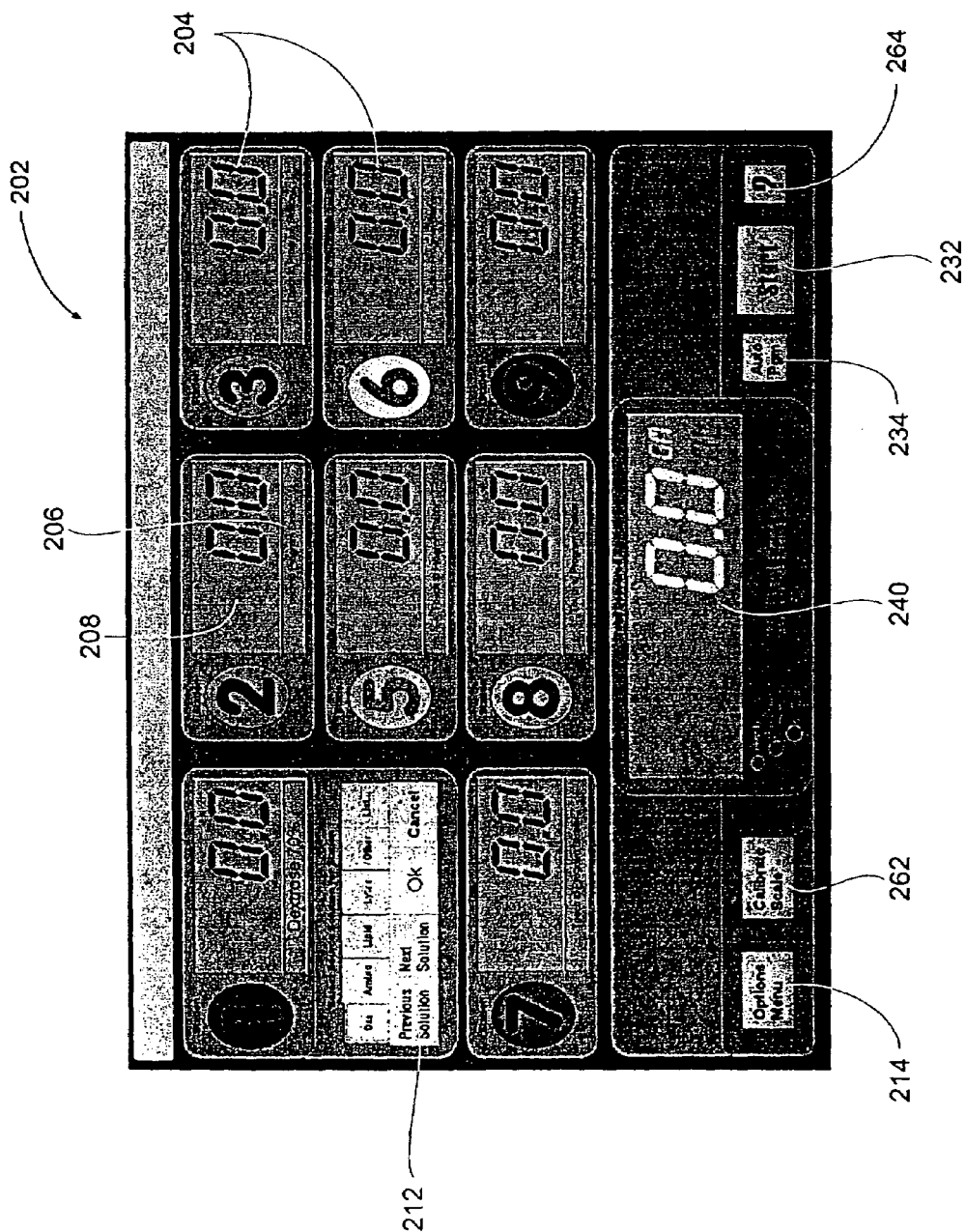
Figure 9E:
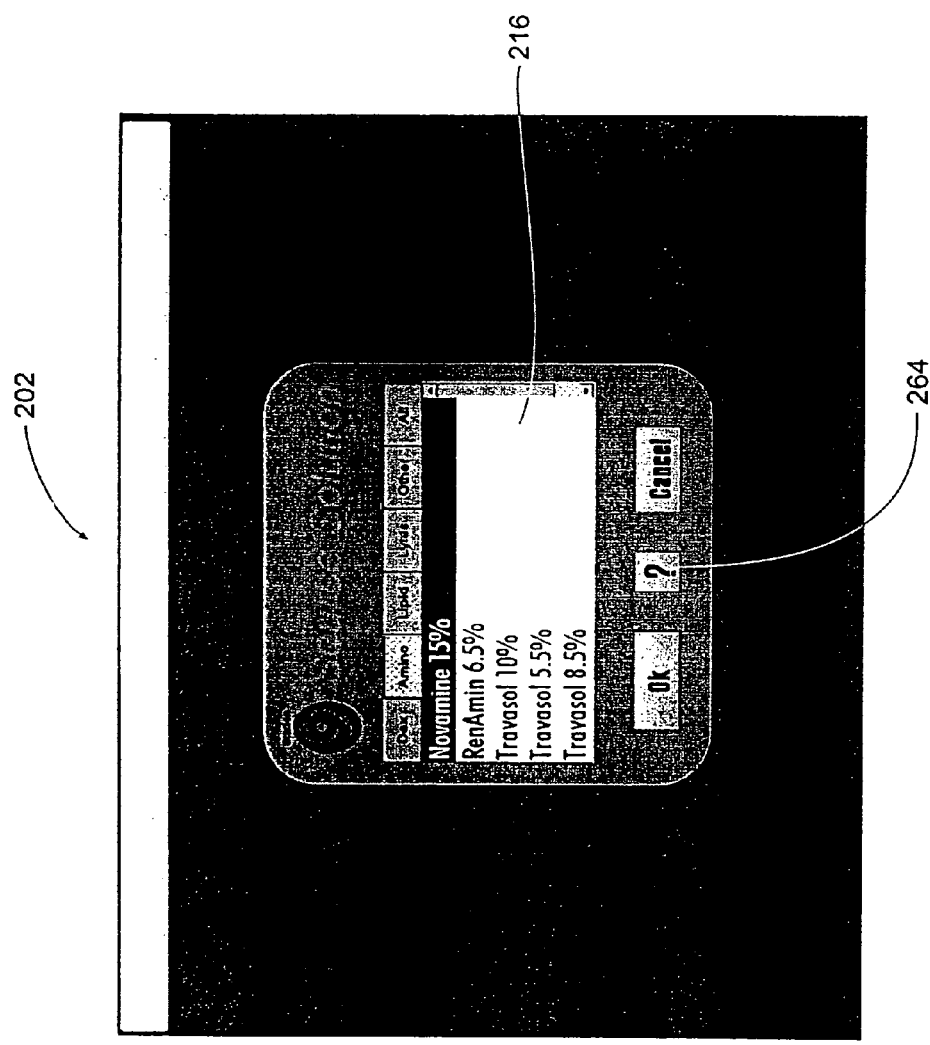
Figure 9F:
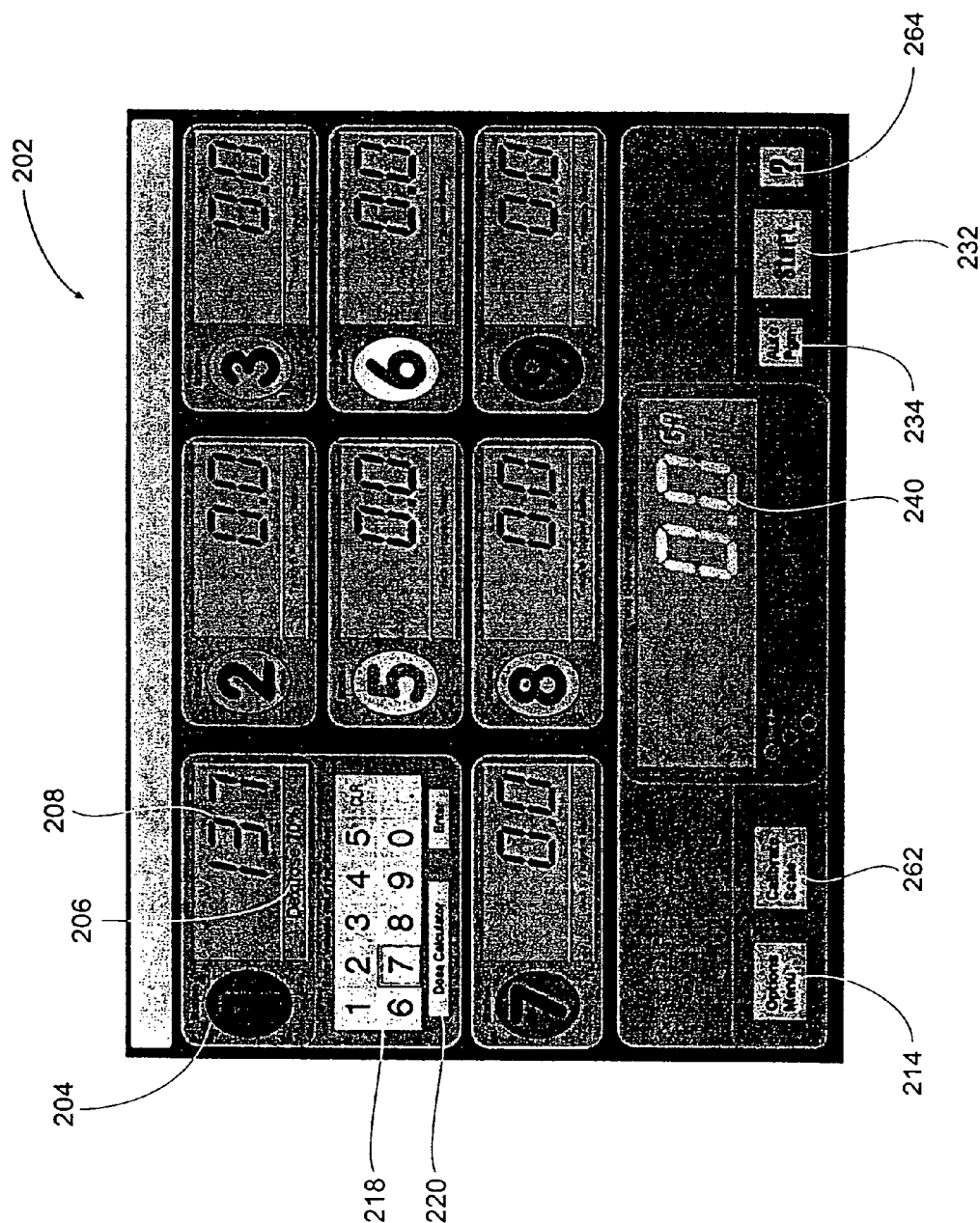
Figure 9G:
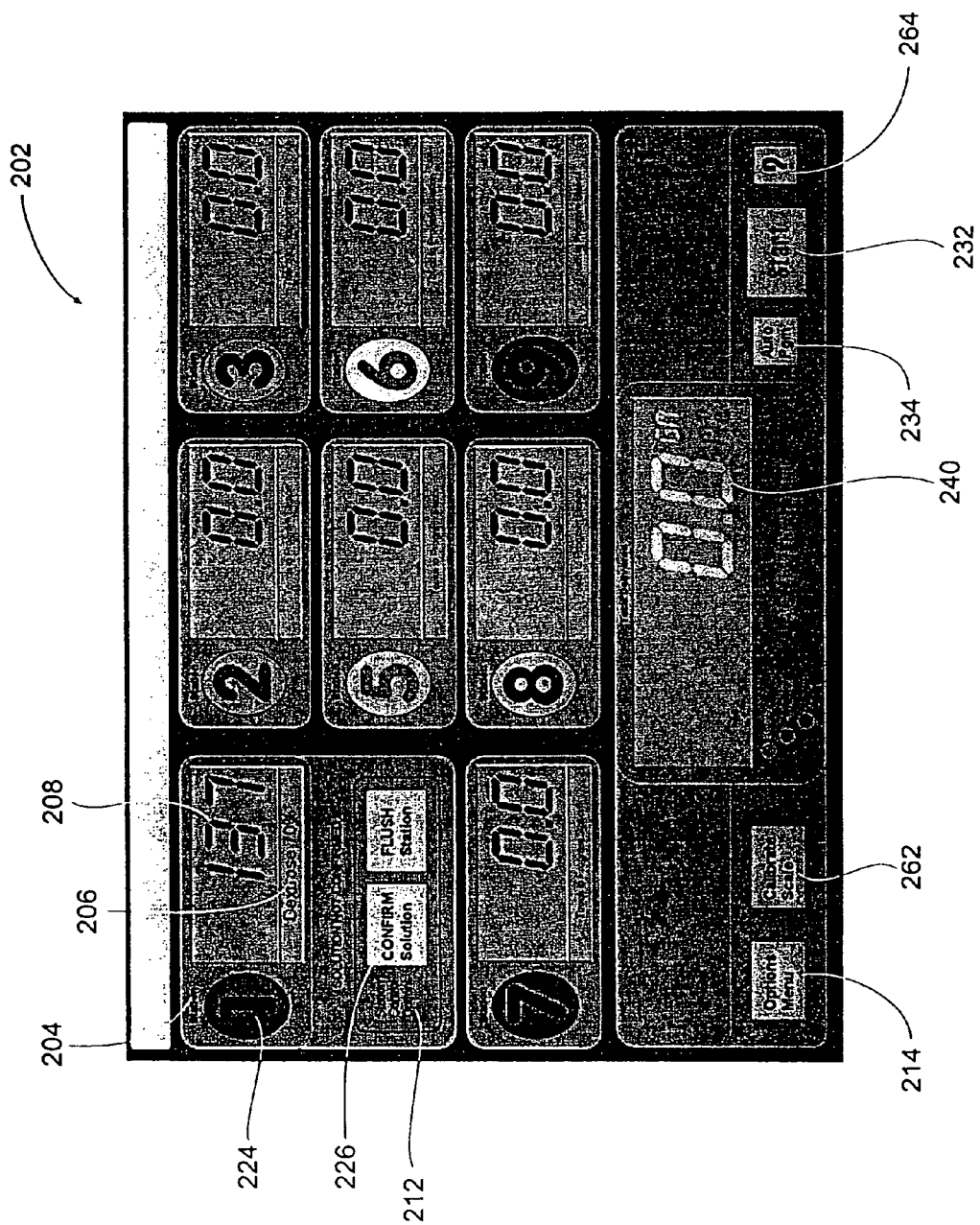
Figure 9H:
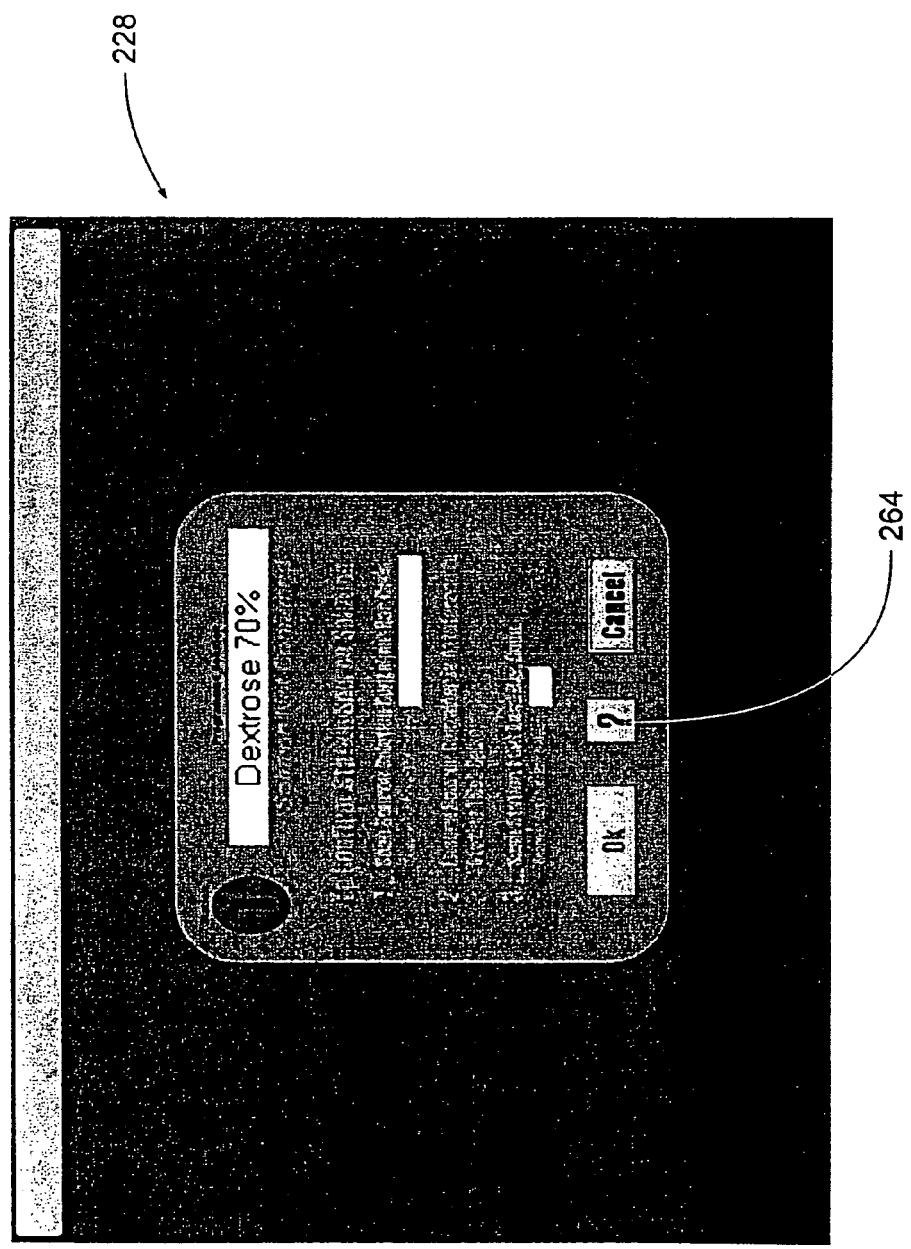
Figure 9I:
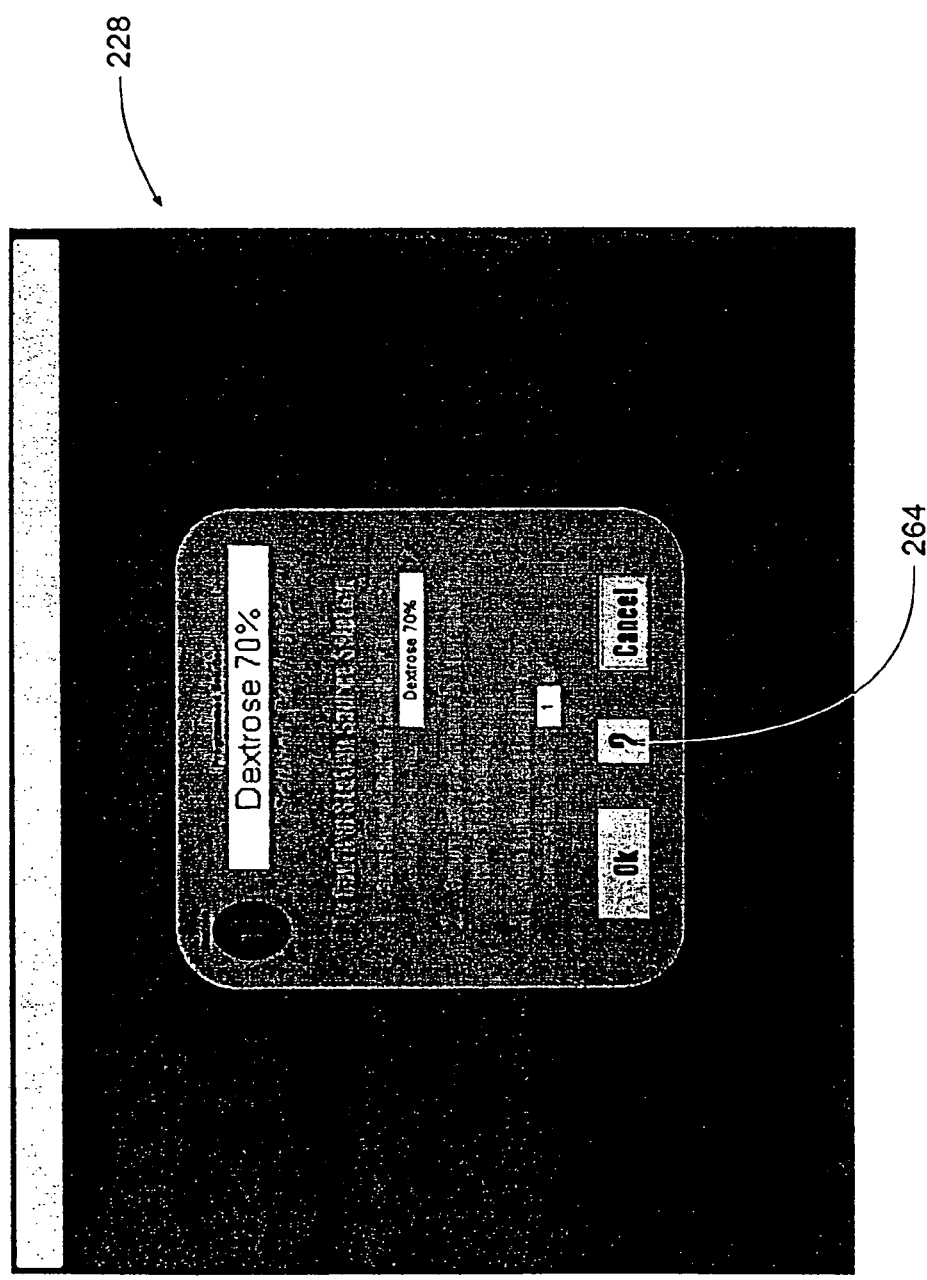
Figure 9J:
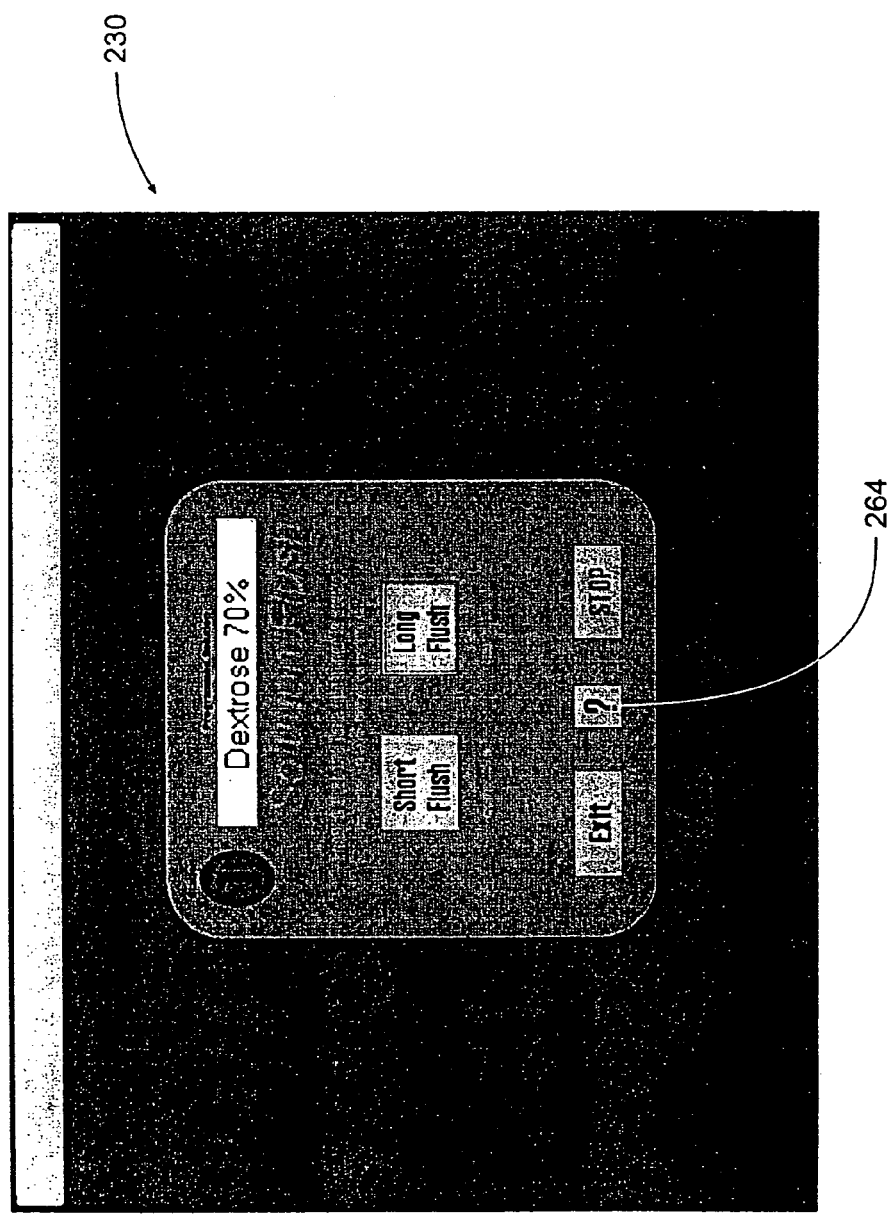
Figure 9K:
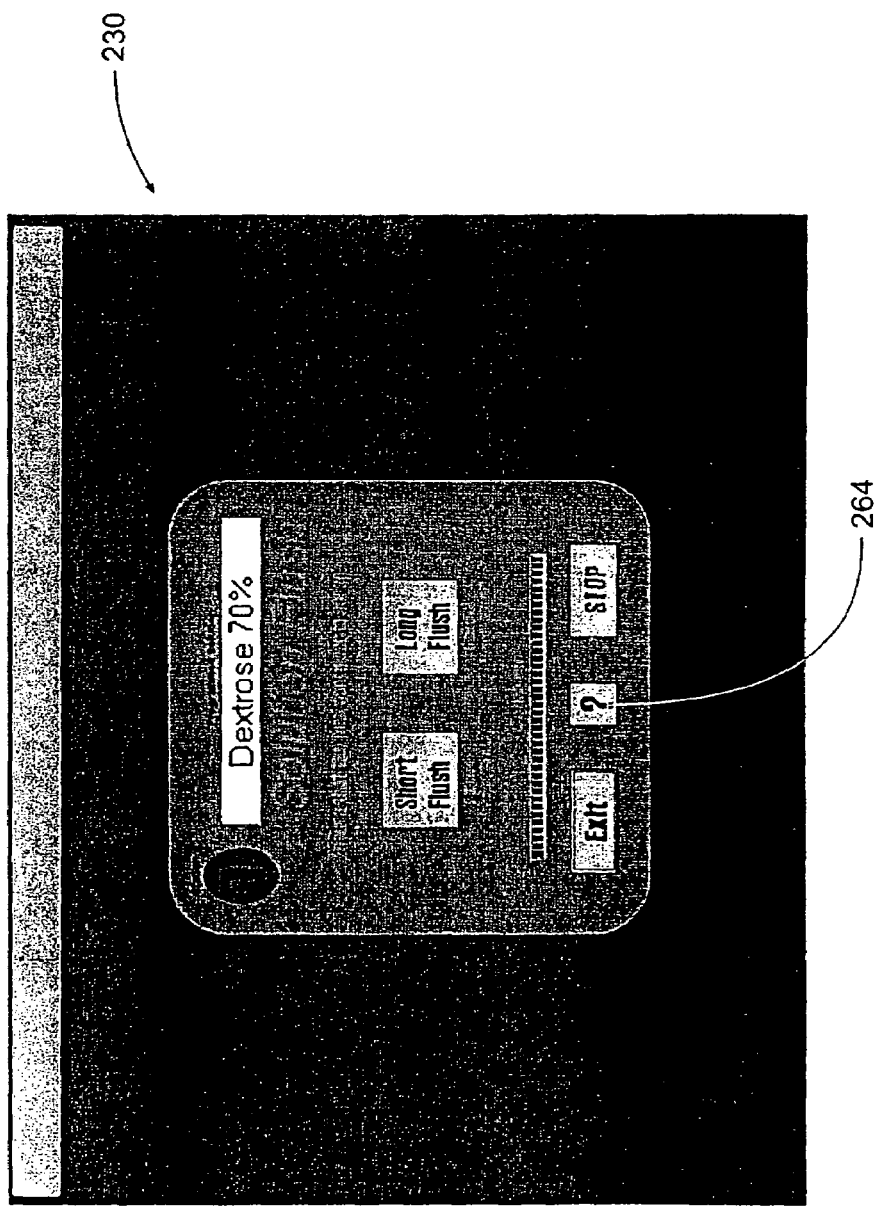
Figure 9L:
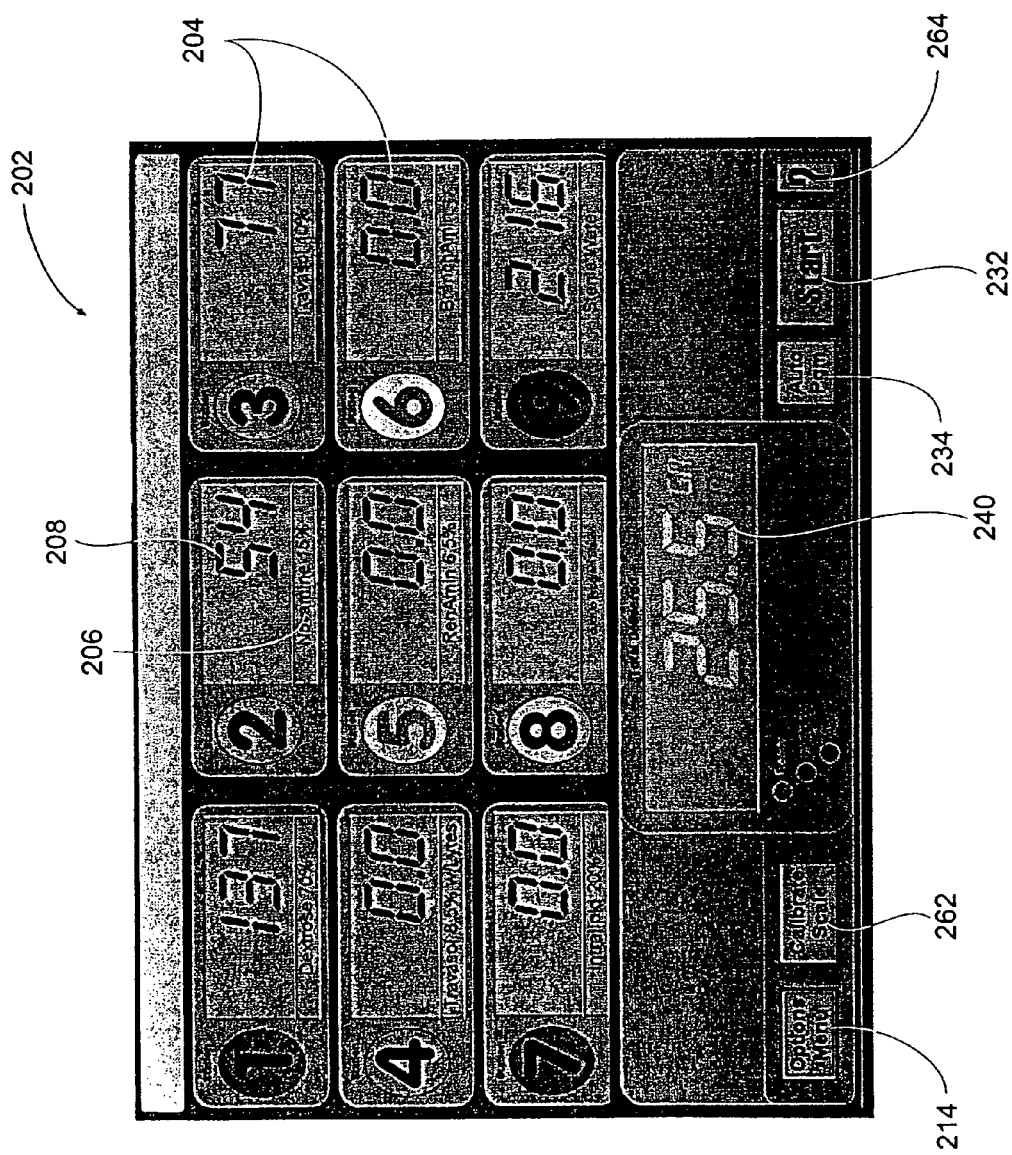
Figure 9M:
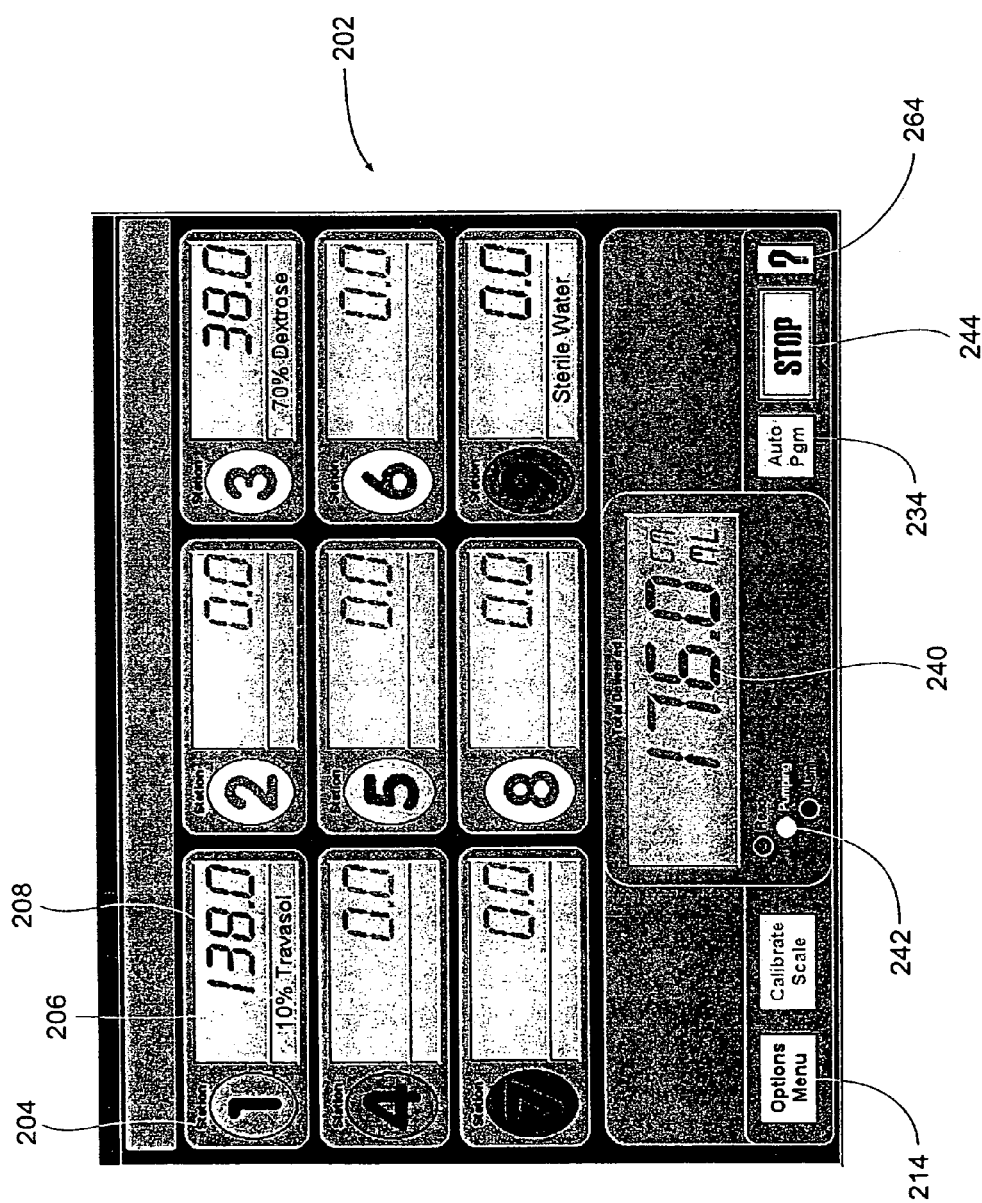
Figure 9N:
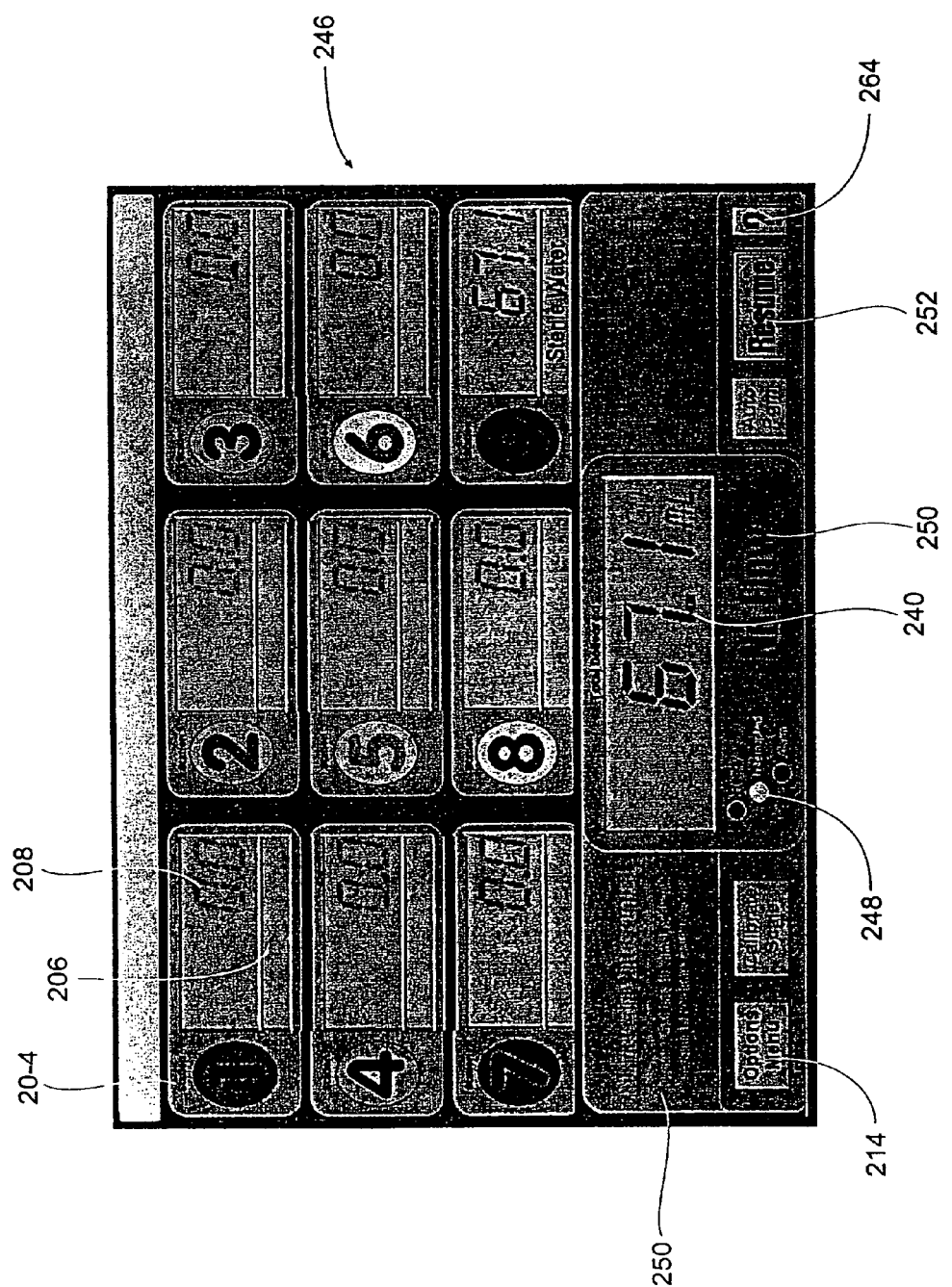
Figure 9P:
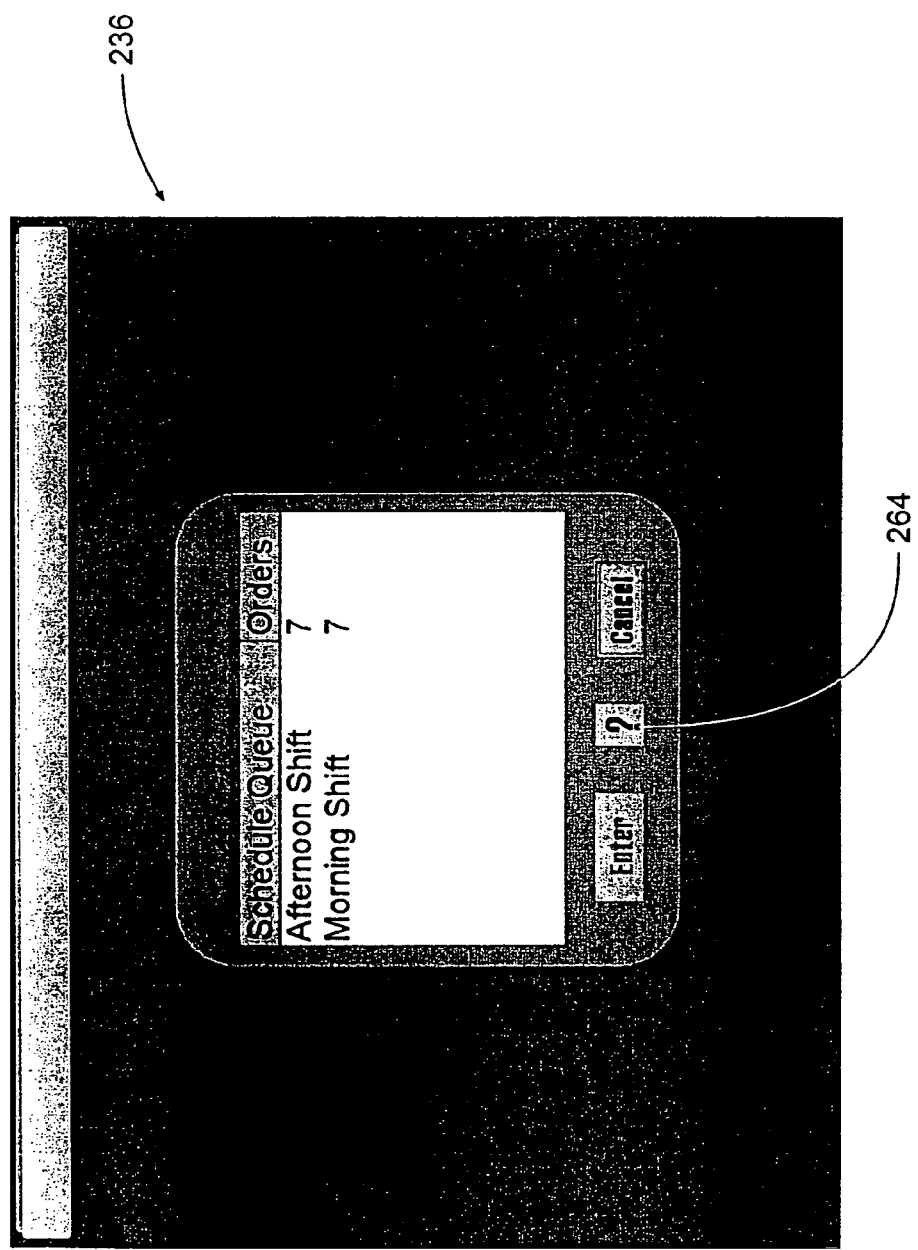
Figure 9Q:
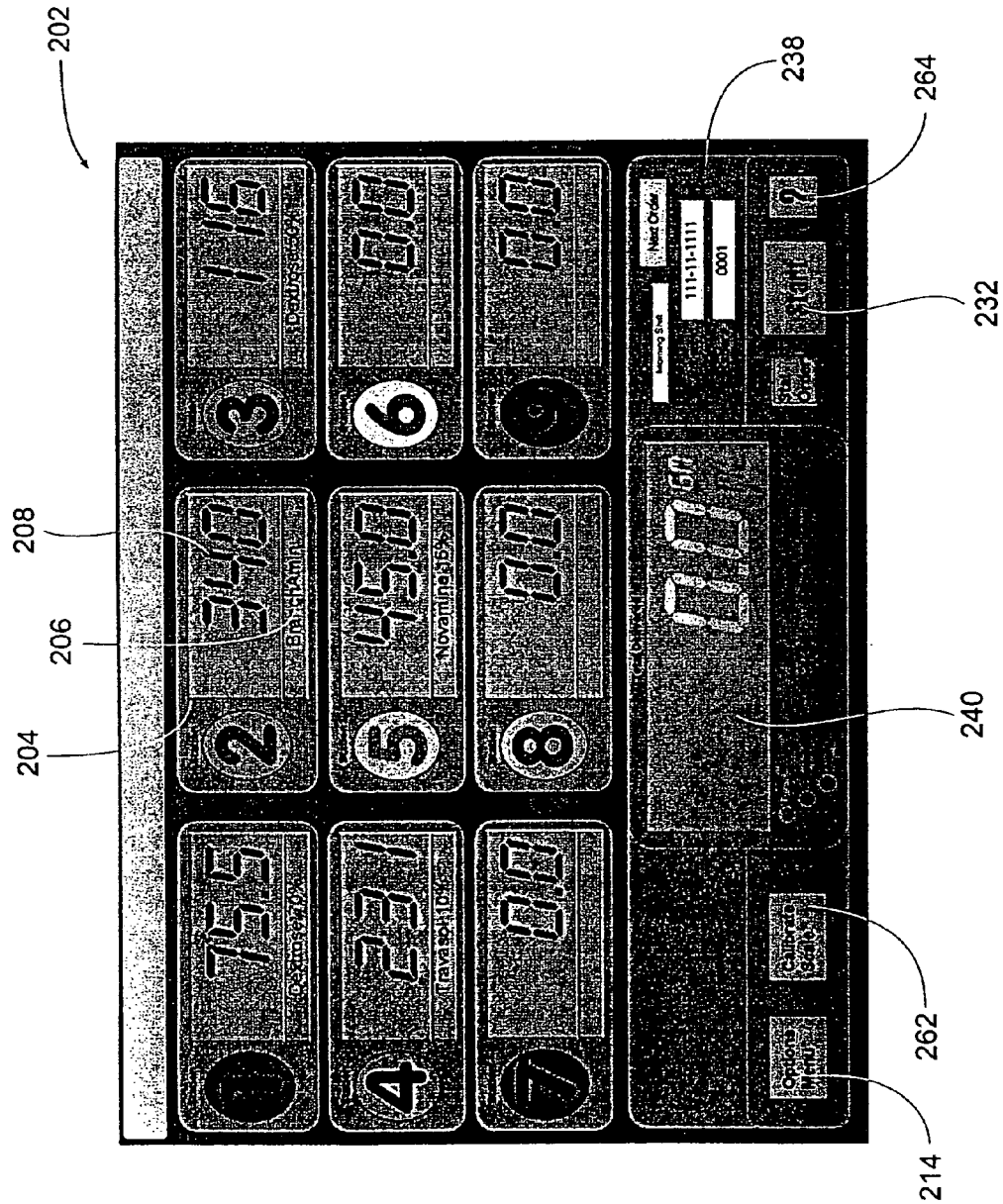
Figure 9R:
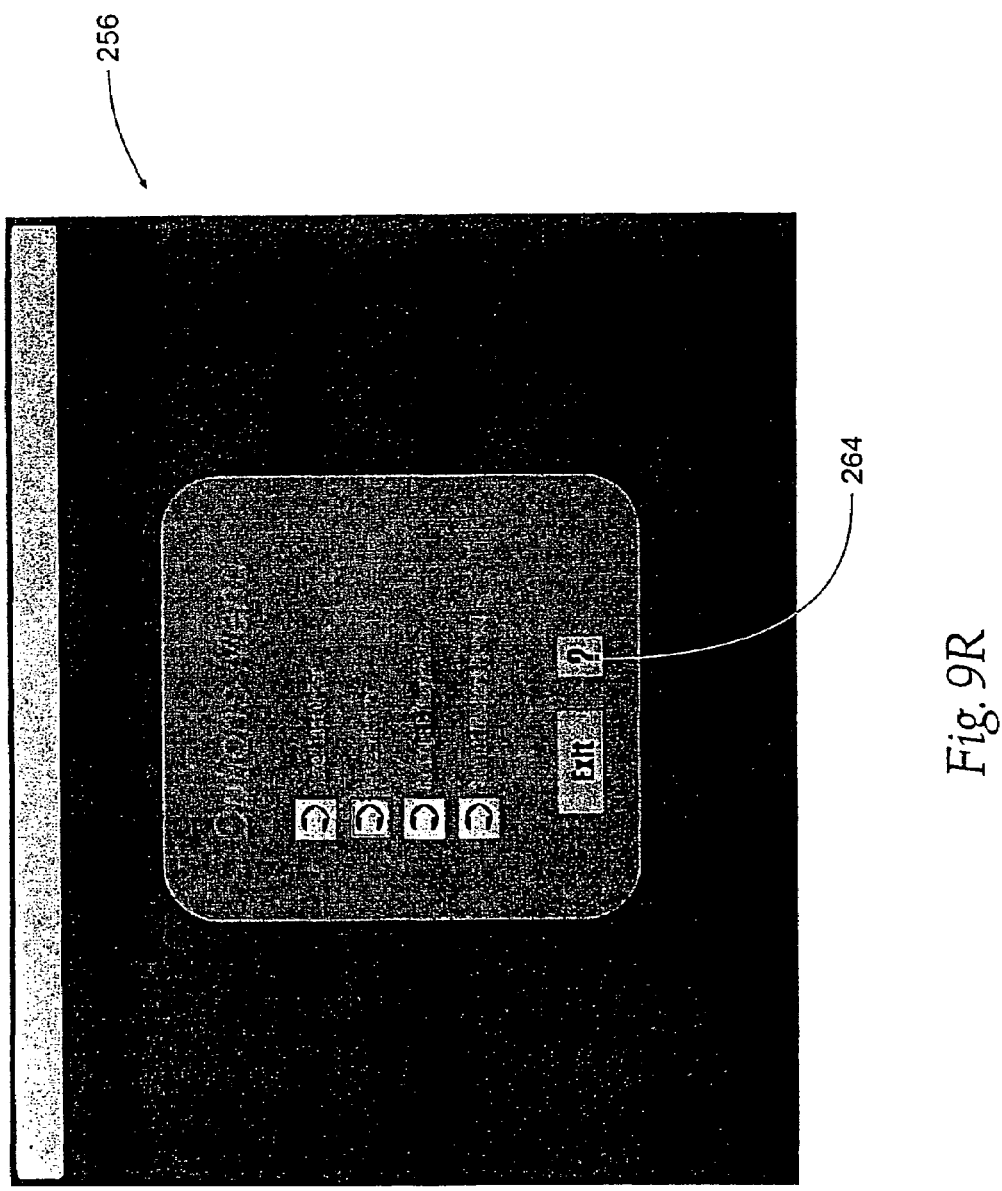
Figure 9S:
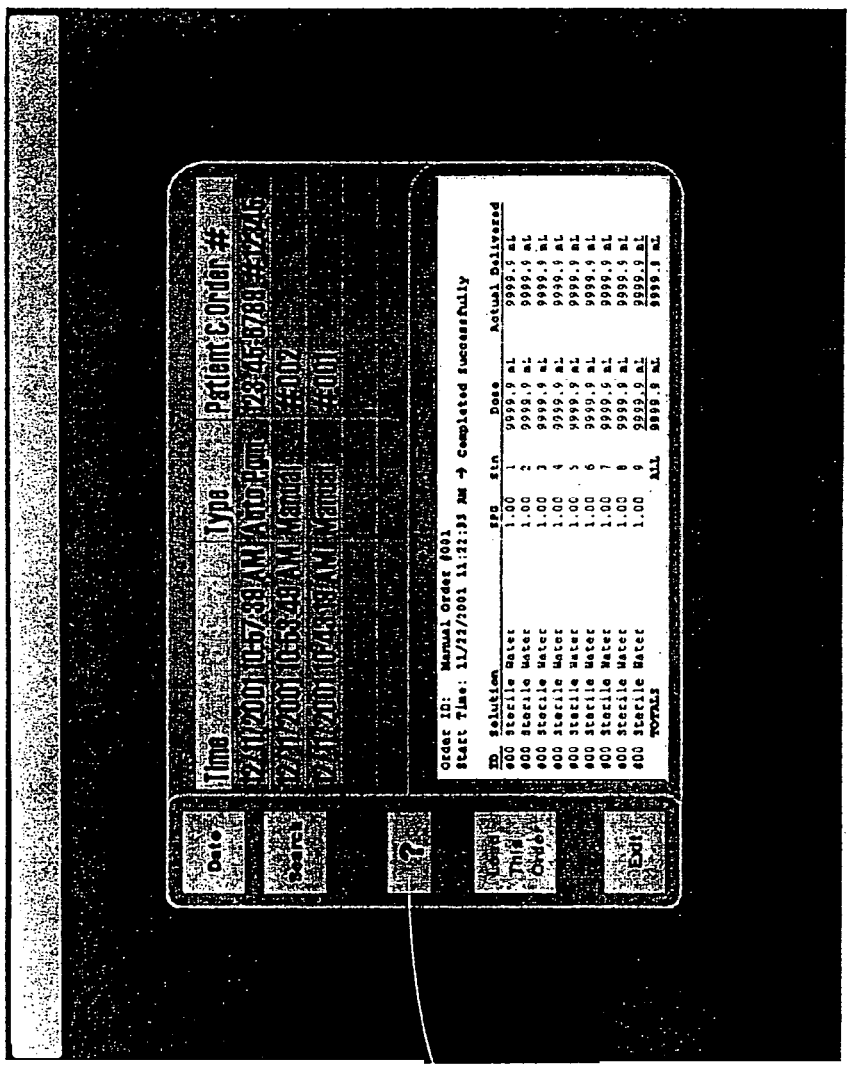
Figure 9T:
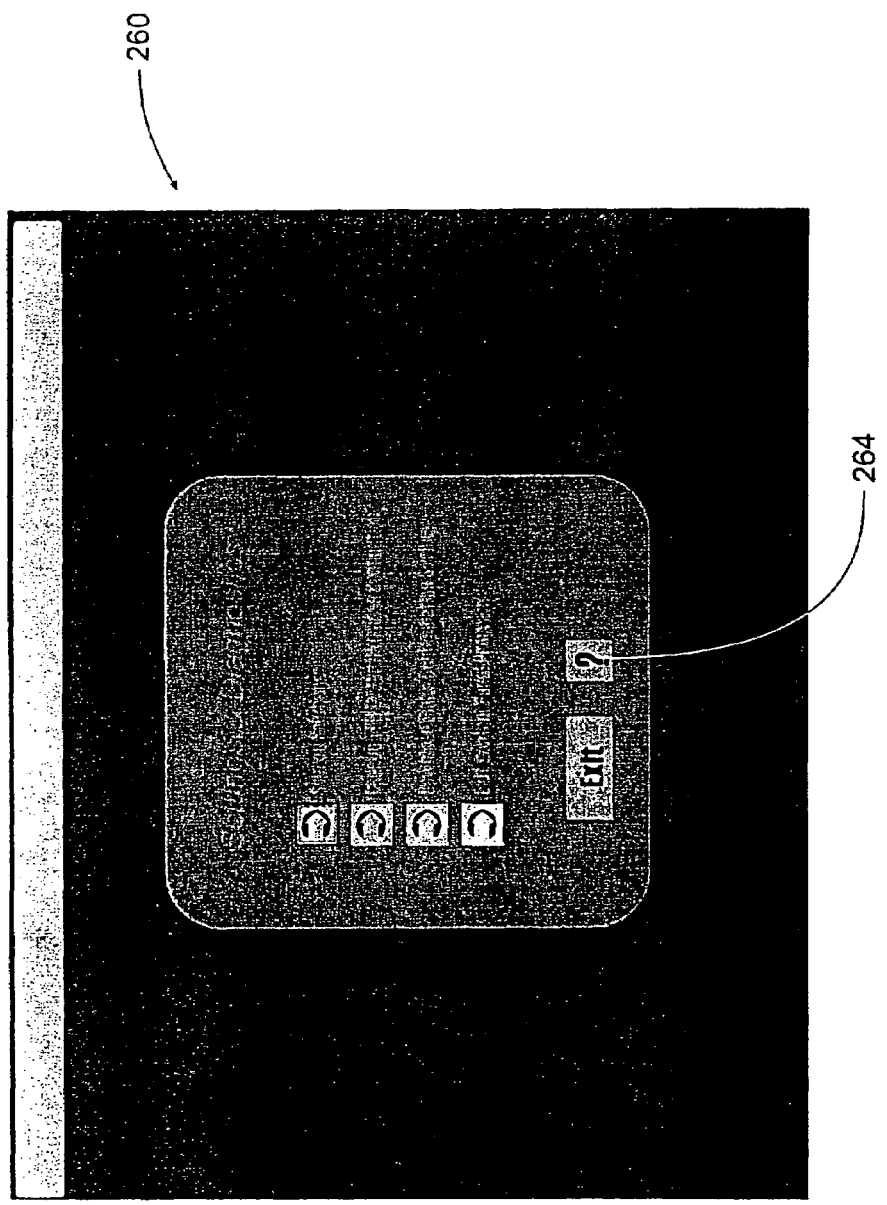
Figure 9U:
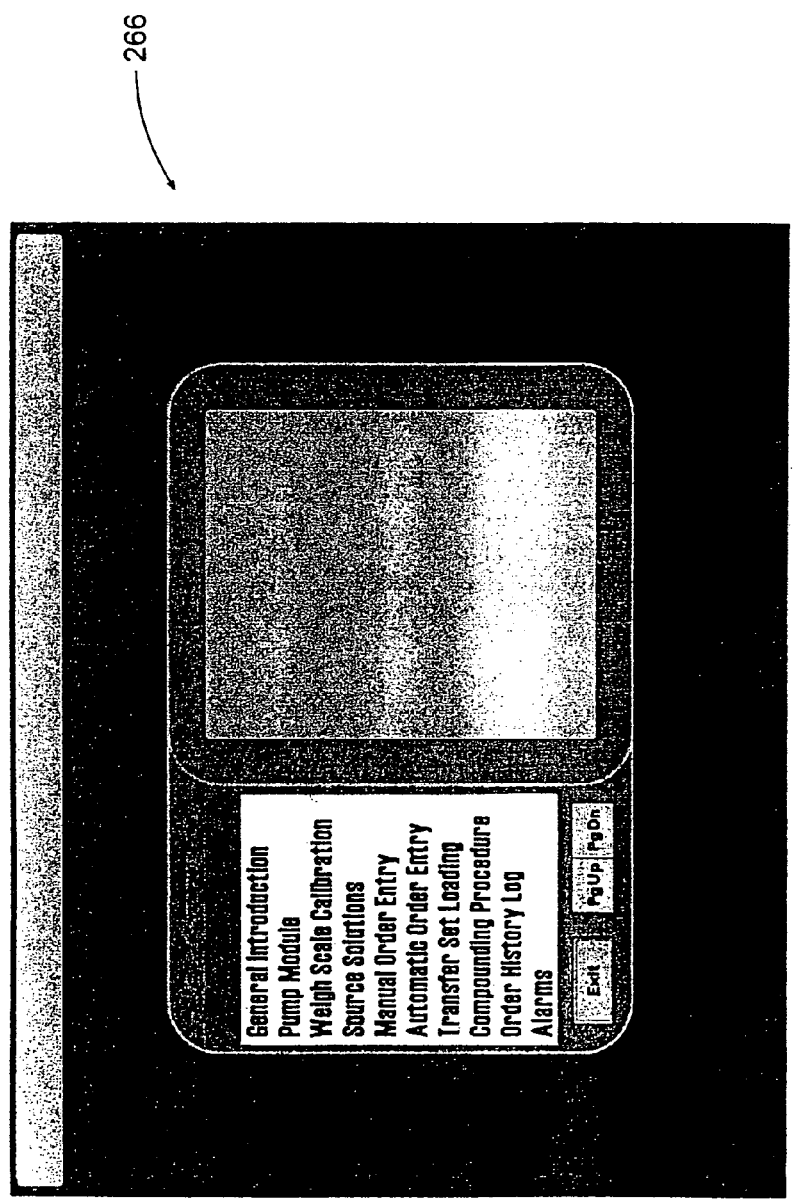
Figure 9V:
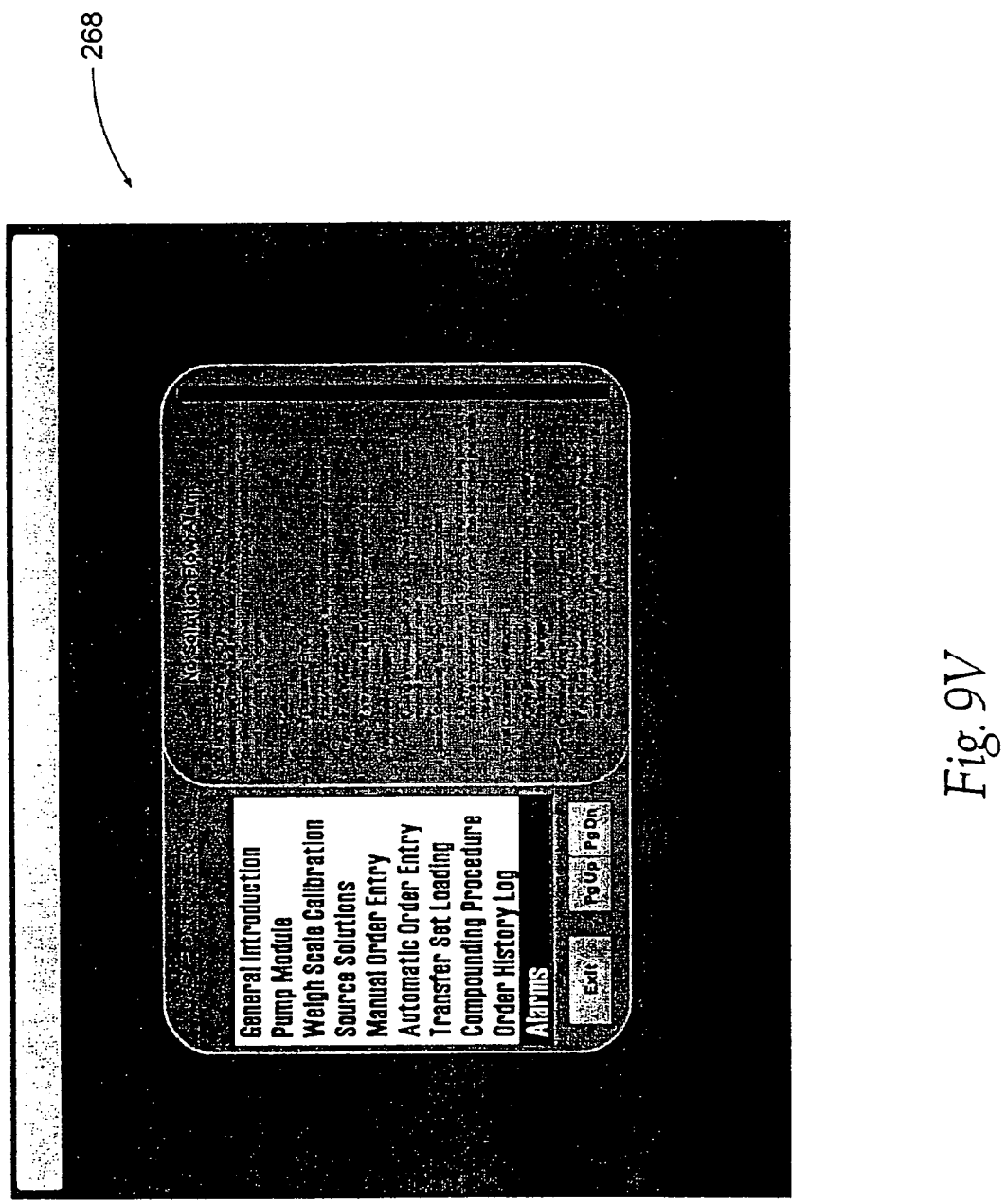
Figure 9W:
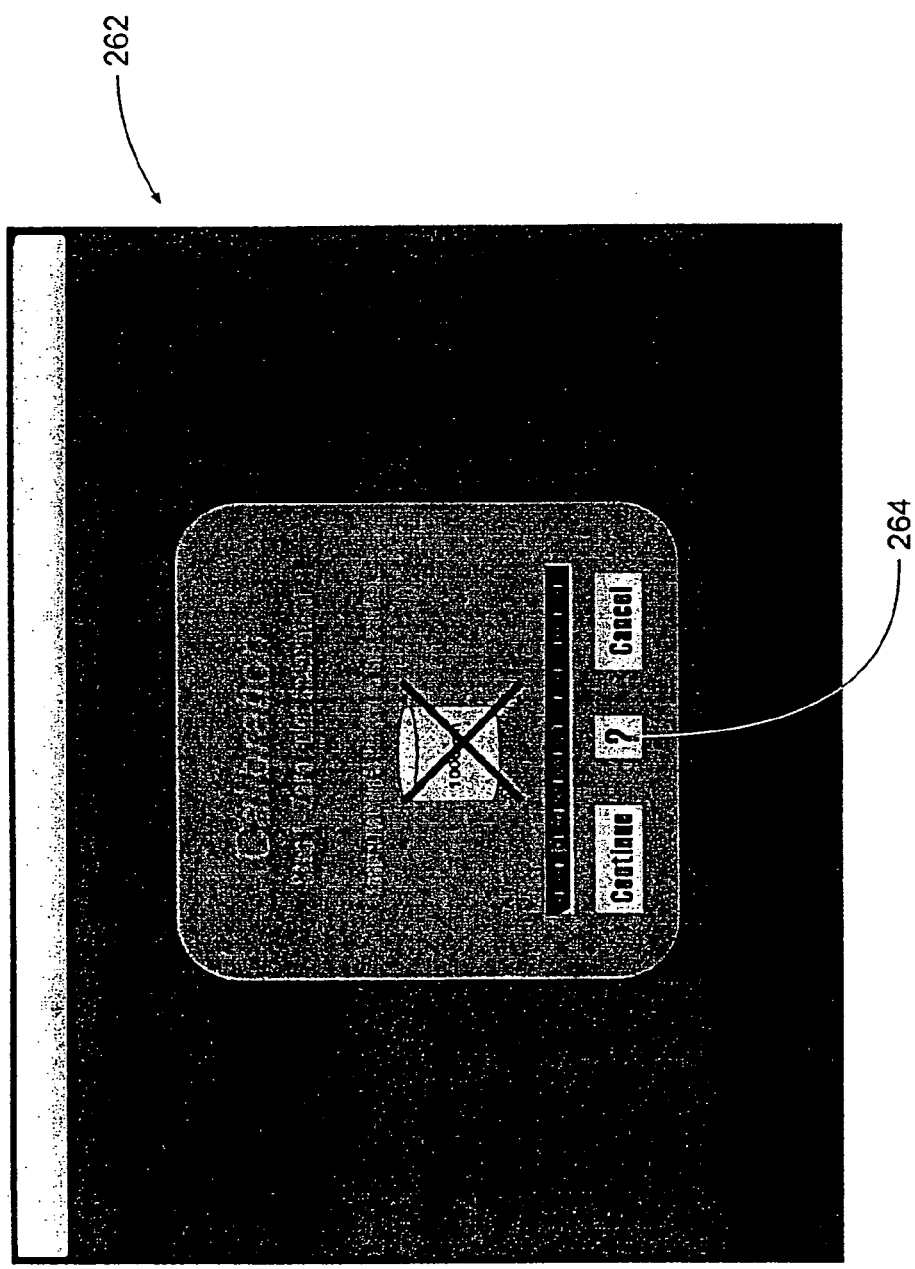

FIGS. 9A to 9W are a walk-through of display screens generated by a representative embodiment of the compounding control manager 72, which demonstrate various features of the compounding control manager 72.

After an initial start-up mode of software initialization, a main work area is created on the display device 76, which initially opens a log-in screen 200 (FIG. 9A). The log-in screen 200 prompts the operator to identify themself, either by using the bar code scanner to scan an operator badge number, or by entry of a badge number or other selected form of identification on the graphical touch screen entry pad. This identification procedure is required for logging-in and/or assessing the operator's level of security clearance. Desirably, a system administrator would have previously established a list of authorized users, against which the sign-in data is compared.

Once an authorized identification is entered, the log-in screen 200 is replaced by a main screen 202 (FIG. 9B). The main screen 202 displays sequentially numbered pump station data fields 204 204. The pump station data fields 204 are desirably numbered according to the left to right placement of the peristaltic pump rotor assemblies 54 in the compounding device. The numbers are also desirably color-coded according to the color code assigned to the peristaltic pump rotor assemblies 54 in the compounding device 18, as previously described.

Each pump station data field 204 includes a solution field 206 for the operator to identify what solution is to be delivered, as well as an amount field 208 to identify how much of that solution is to be delivered. The solution field 206 includes a touch button 210 that prompts TOUCH TO PROGRAM STATION. Touching the prompt button 210 allows to operator to enter data in the solution and amount fields 206 and 208 required by the compounding control manager 72.

Touching the prompt button 210 first opens a solution programming box 212 (FIG. 9C). The solution programming box 212 displays within the main screen 202 an array of touch buttons that either contain a specific identification of a solution type—e.g., DEX (dextrose); AMINO (amino acid); LIPID (fat emulsion); LYTES (electrolytes)—or allow the operator to specify another solution type (OTHER), or ask for a list of available solutions (LIST). Desirably, a system administrator would have previously established a list of solutions, using the OPTIONS MENU touch button 214 on the main screen 202, as will be described later. Other touch buttons in the solution programming box allow the operator to scroll through a list of solutions (PREVIOUS SOLUTION, NEXT SOLUTION). Another button (OK) allows for a verification of the identified solution and entry of that solution in the solution field 206, or an exit button (CANCEL) that closes the solution programming box 212 with no data entry in the solution field 206. Selection of a specific solution type button (e.g., DEX) (see FIG. 9D) either enters the only solution of its type on the list (i.e., Dextrose 70%), or, if there are various selections to be made (e.g., by selecting AMINO), displays a solution listing box 216 for that solution type (see FIG. 9E), from which the operator selects by touch.

Once the solution type has been selected, the operator selects the OK button on the solution programming box 212, and the solution type appears (see FIG. 9F) in the solution field 206 of the pump station data field 204. An amount programming box 218 is also opened (FIG. 9F), which replaces the solution programming box 212. The amount programming box 218 comprises a graphical numeric keypad, by which the operator can enter an amount expressed in a selected unit which is to be transferred by the selected pump station from the source solution container into the final container (e.g., volume, expressed in mL). The unit for the amount can also be specified by use of the DOSE CALCULATOR touch button 220. Once the numeric amount is entered, pressing the ENTER touch button in the amount programming box 218 enters the entered amount in the amount field 208 of the pump station data field 204 (see FIG. 9F), and the amount programming box 218 closes.

The station control box 222 (FIG. 9G) can also be optionally selected by pressing the station number identification icon 224. The station control box 222 requires that the transfer of the solution identified in the solution field 206 be confirmed by the operator pressing the CONFIRM SOLUTION touch button 226. Pressing the CONFIRM SOLUTION touch button 226 opens a solution confirmation box 228 (FIG. 9H). The operator is prompted to scan a bar code on the source solution container (using the bar scanner input device 82). This bar code identifies, e.g., the solution type, the lot number of the solution, and its expiration date. By scanning the bar code, the compounding control manager 72 links this information to a specific compounding order for verification and solution tracking purposes. Furthermore, the compounding control manager 72 can implement expiration date control, locking out the use of expired solutions. The integration of the bar code scanning function with the compounding control manager 72 integrates lot number and expiration date tracking and/or verification to the operation of the compounding device 18.

The operator is also prompted to visually assure that the transfer tubing 34 having the unique coding corresponding to the pump station number is coupled to the source container from which the bar code is scanned, as well as scan the bar code component of the unique code on the transfer tubing 24 for that pump station. As confirmation of the correct source solution container 15 and transfer tubing 24 is made by the operator by scanning bar codes, information in the solution confirmation box 228 is updated (see FIG. 9I). After full confirmation is accomplished, the operator can press an OK touch button in the solution confirmation box 228.

The solution flush box 230 (see FIG. 9J) can also be optionally selected by pressing the FLUSH station control button on the station control box 222 (see FIG. 9G). The solution flush box 230 includes touch buttons that prompt the operator to conduct a SHORT FLUSH (e.g., 2 seconds) or a LONG FLUSH (e.g., 5 seconds), during which time the compounding control manager 72 operates the corresponding peristaltic pump rotor assembly 54 for the selected pump station. The load cell 30 monitors for weight changes, indicating entry of solution into the final container 14, to verify (if desired) that flow communication exists between the source solution container 16 and the final container 14. The solution flush box 230 indicates completion of the flush (see FIG. 9K), and the operator is prompted to by an EXIT touch button to return to the main screen 202. Flush is not required prior to the start of compounding, but is available as an optional set up step.

The operator is prompted to follow the above prescribed sequence for each source solution and each pump station, until programming is complete. FIG. 9L shows the main screen 202 after (i) the operator has programmed the compounding control manager 72 to mix 137 mL of 70% dextrose (pump station 1), 54 mL of 15% novamine (pump station 2), 77 mL of 10% Travasol (pump station 3), and 216 mL of sterile water (pump station 9) from source solution containers into the final container, and (ii) the operator has also verified for each pump station that the proper source solution and transfer tubing set up are present. As FIG. 9L shows, the main screen 202 lists the solutions and amounts in the respective fields 206 and 208 of each pump station box 204 and, further, prompts the operator to press a highlighted START touch button 232. Upon selection of the START touch button, compounding immediately commences under the control of the compounding control manager 72. If one or more of the source solutions have not been confirmed at the time the operator presses the START button 232, the compounding control manager 72 will automatically prompt the operator to confirm each remaining source solution before compounding is allowed to begin. The START touch button 232 is not enabled by the compounding control manager 72 until all required preliminary steps have been satisfactorily completed.

Alternatively, the operator can select an AUTO PGM touch button 232 on the main screen 202 (see FIG. 9L). This opens a queue selection screen 236 (FIG. 9P), which displays a list of preprogrammed schedule queues established by the system administrator. The operator selects the desired queue and presses the ENTER touch button on the queue selection screen 336. The compounding control manager 72 holds the order queue list in memory, and the main screen 202 (see FIG. 9Q) allows the operator to view the current order queue list, one order at a time, in a queue box 238. In this arrangement, the operator selects the order from the programmed order queue list on the main screen 202, and then starts compounding. Alternatively, the operator can scan a bar code on a final solution container to be compounded. The compounding control manager 72 uploads and presents the compounding order for that final container.

As compounding proceeds, the compounding control manager 72 updates the number TOTAL DELIVERED field 240 (by incrementing up) and amount field 208 (by incrementing up) of the respective pump station field 204 of the main screen 202 (FIG. 9M), to indicate the series transfer of liquid from the several source containers 16 into the final container 14. In FIG. 9M, pump stations 1, 2, and 3 have been programmed. Station 1 has completed its pumping (having delivered the desired 138 mL. Station 3 has begun to pump (having pumped 38 mL). Station 9 is waiting to begin. The TOTAL DELIVERED field 240 shows 176 mL, which is the current sum of amounts pumped by pump stations 1, 2, and 3. The PUMPING icon 242 is illuminated to indicate that compounding is proceeding. The operator can, if desired, terminate compounding by pressing the illuminated STOP touch button 244.

If, during the course of compounding, the load cell 30 indicates that there is no liquid transfer into the final container 14, the compounding control manager 72 generates a pumping alarm. The compounding control manager 72 interrupts the compounding procedure when this alarm condition occurs. The compounding control manager 72 opens a pumping alarm screen 246 (FIG. 9N). The INTER- RUPTED icon 248 is also illuminated to indicate that compounding is not proceeding. An information field 250 displays information pertaining to the alarm condition. The information field 250 prompts the operator to take corrective action and, by pressing a RESUME touch button 252, to commence compounding once again.

Figure 90:
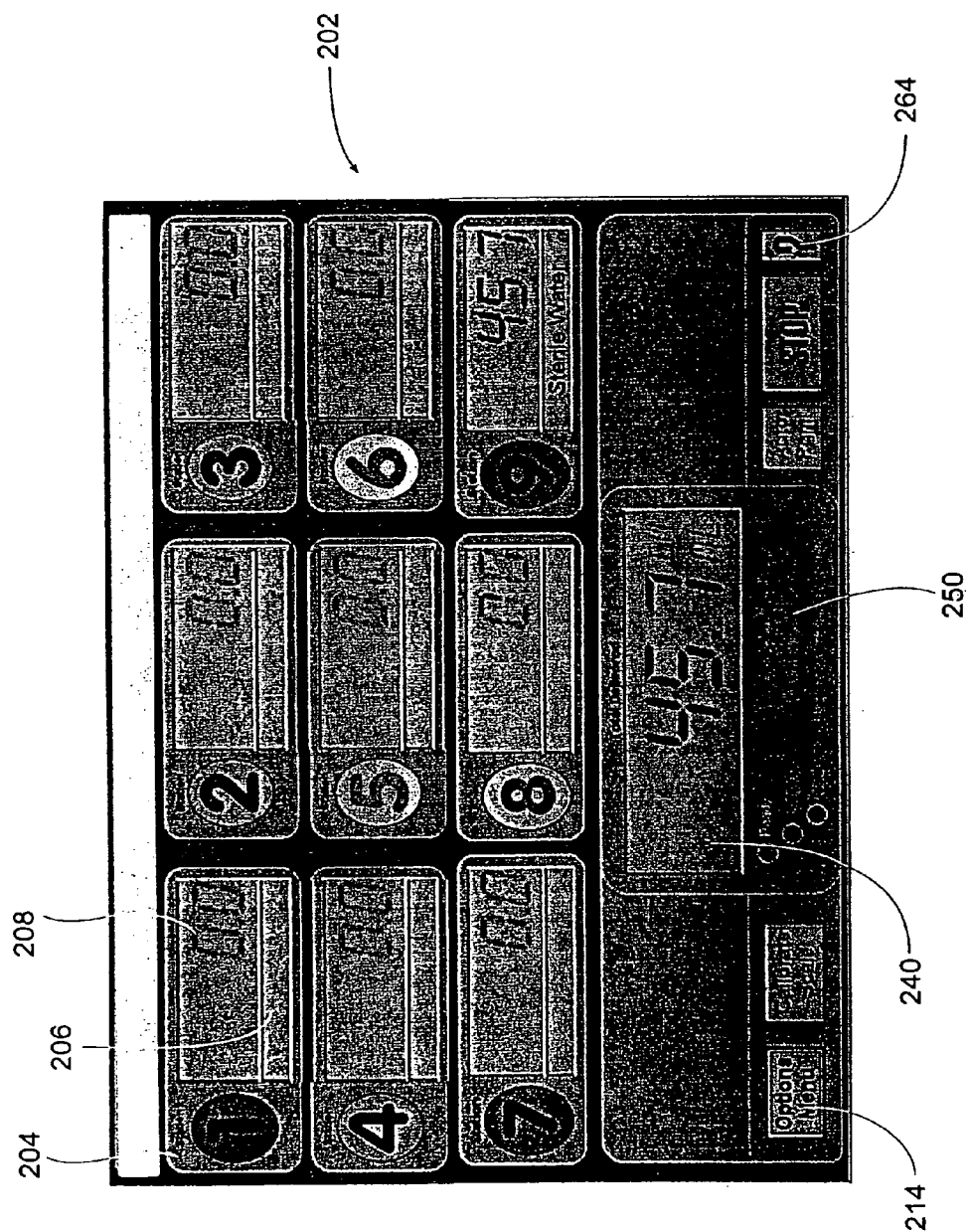

When compounding is complete, the compounding control manager 72 displays a COMPLETE message in the information field 250 (see FIG. 90) and prompts the operator to remove the final container 14.

The operator can then reprogram the compounding control manager 72 to carry out another compounding regime by following the above sequences of steps.

There are other graphical buttons on the main screen 202 (see FIG. 9A), which may be used to carry out various support functions. For example, by pressing the OPTIONS MENU touch button 214, the options menu screen (FIG. 9R) is displayed. The option menu screen prompts the operator to select among a list of administrative functions that, in the illustrated embodiment, include REPEAT LAST ORDER, ORDER HISTORY, SETTINGS AND DIAGNOSTICS, and SIGN OFF. Pressing the REPEAT LAST ORDER button automatically configures the compounding control manger to compound according to the most recent order. Pressing the ORDER HISTORY button displays an order history screen (FIG. 9S), that lists the compounding orders that have been executed by the compounding control manager 72. These compounding orders are maintained in memory by the compounding control manager 72. Pressing the SETTINGS AND DIAGNOSTICS button displays the settings and diagnostic screen 260 (FIG. 9T) that displays additional administrative functions that the system administrator can perform, such as establishing the list of available source solutions for the solution programming box 212 (FIGS. 9D and 9E), previously discussed. Other additional administrative functions can also be accessed through this screen. Pressing the SIGN OFF button displays a fresh log-in screen, and the compounding control manager 72 awaits a new order sequence from an operator.

In the illustrated embodiment, the main screen 202 also includes a CALIBRATE SCALE touch button 262 (see FIG. 9A). When pressed, the button 262 opens an instruction screen (FIG. 9W), that leads the operator through a sequence of steps that calibrate the load cell.

Also displayed on the main screen 202 is a HELP icon 264 (identified by a question mark—?). Pressing the HELP icon 264 on the main screen 202 opens a main screen help screen 266 (FIG. 9U), which displays a list of available help topics pertaining to the compounding control manager 72 and operation of the compounding device 18 in general. Desirably, a HELP icon 264 is also present on every other functional screen or box generated by the compounding control manager 72 (see, e.g., FIGS. 9A, 9E, 9H, 9P). Pressing the HELP icon 264 on any given screen opens a context sensitive help screen, which provides guidance pertaining to the particular function that the given screen performs. For example, FIG. 9V shows a context sensitive help screen 268 that opens when the HELP icon 264 on the pump alarm screen 246 (FIG. 9N) is pressed. As can be seen, the context specific help topic is NO SOLUTION FLOW ALARM, and the screen provides instructions for correcting the alarm condition.

In a desired implementation, the compounding control manager 72 incorporates within its preprogrammed structure an integrated selection of training and/or help video files, e.g., in MPEG format. The integrated training and/or help video files contain formatted pre-taped video footage and streaming audio. When presented by the compounding control manager 72 on the display screen 76, the files communicate information to the operator in a direct visual and audible way. This platform of communication, which forms an integrated part of the compounding control manager 72, provides the operator direct, real time access to context specific information in an effective, first person, visual and audible format, eliminating the need to resort to offline training manuals or separate CD's.

Figure 14A:
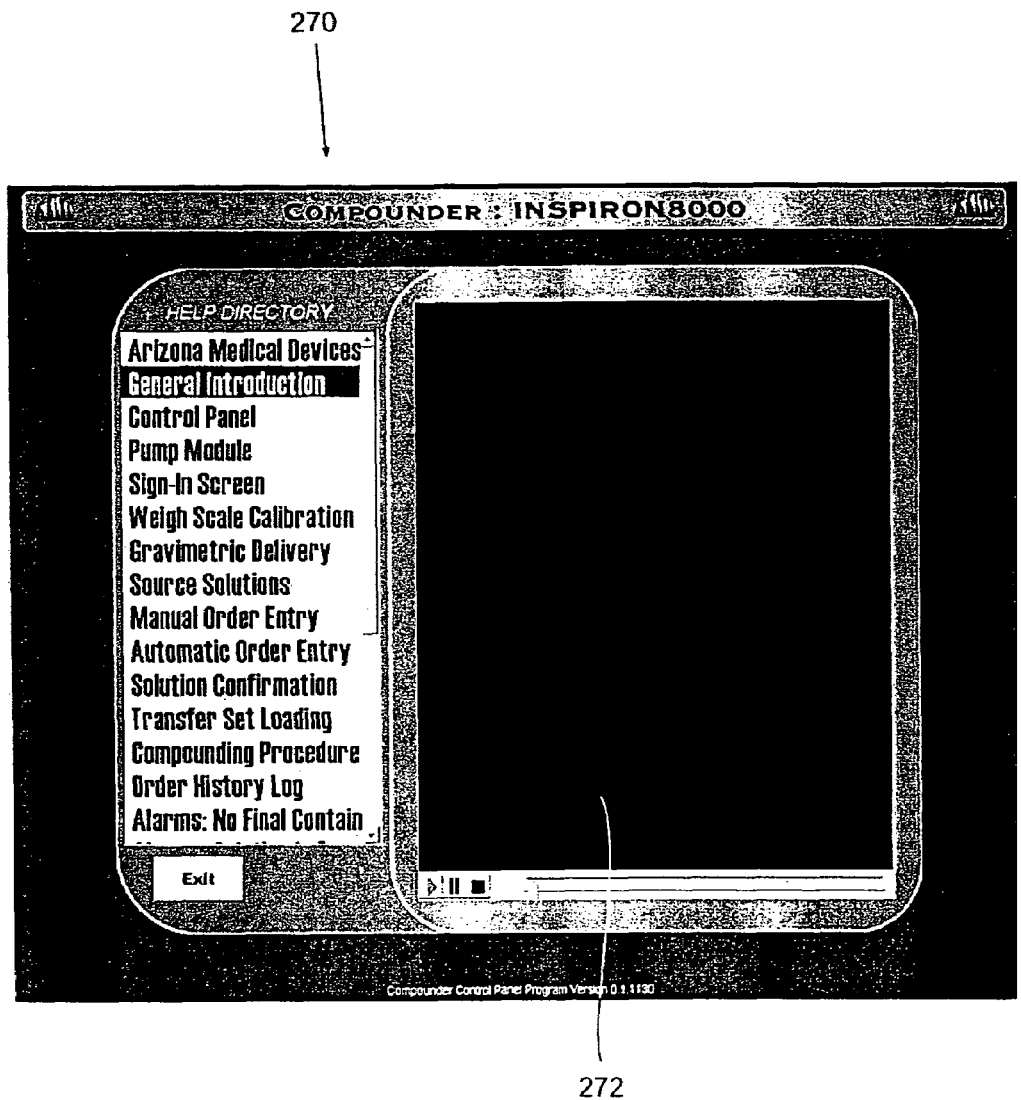
FIG. 14 are representative screens of a training/help video-audio function that can be integrated with the compounding control manager of the compounding device shown in FIG. 1.

In a representative implementation, pressing the HELP icon 264 on the main screen 202 opens a main screen video training/help screen 270 (FIG. 14A). The screen 270 displays a list of available training/help topics pertaining to the compounding control manager 72 and operation of the compounding device 18 in general. The screen incorporates 270 a MPEG viewing area 272, in which the training and/or help video files in the compounding control manager 72 are displayed. Selecting an instruction/help topic runs the associated MPEG file.

As an example, FIGS. 14B(1) to 14B(8) show representative screen captures from a training/help video for "Programming the Compounder." The training/help video, with associated streaming sound file, walk an operator through the steps of entering a compounding order using the graphical user interface of the compounding control manager 72. These steps have been previously described, with reference to FIGS. 9B to 9F. The training/help video explain that the first step is to identify the source solution (FIG. 14B(2), and then proceed (FIG. 14B(3), by visual and audible instructions, the procedure for using the Solution Programming Box 212 (previously described in the context of FIGS. 9C and 9D). The training/help video then explain that the next step is to determine the solution volume (FIG. 14B(4), and then proceed (FIGS. 14B(5)to 14B(7), by visual and audible instructions, the procedure for using the Amount Programming Box 218 (previously described in the context of FIG. 9F). The training/help video concludes (FIG. 14B(8)) by congratulating the operator for successfully accomplishing the programming procedure.

As can by now be appreciated, the compounding control manager 72 serves to generate an interactive user interface that presents as much information/control on one screen as possible without making the screen too busy. Among its features are (i) to minimize user entry errors by making their entry points very focused and utilizing large display and keypad areas; (ii) to minimize keystrokes for the experienced user; (iii) to provide as much help as possible for the inexperienced user; and (iv) to minimize calls to service by making "smart help" available.

The compounding control manager 72 makes possible the operation of a gravimetric compounding device 18 under direct software process control, while utilizing bar-codes as a process quality control mechanism.

B. The Order Entry Process Manager

The order entry process manager 84 can be installed on the MPU 58 of the controller 20 and/or on another workstation linked to the controller 20. The order entry process manager 84 provides an array of enhanced order entry functions for the compounding control manager 72. The order entry process manager 84 also provides an information management function and label printing function, that make possible simplified and consolidated order data record storage and control on a patient-by-patient basis. This function is integrated with the communication of the order data to the compounding control manager 72 of a compounding device 18, to thereby facilitate set-up, operation, and management of an overall compounding system in a reliable fashion that minimizes error. The order entry process manager 84 makes possible a centralized or distributed order data entry, order data storage, order data manipulation, and order data communication system.

Figure 8A:
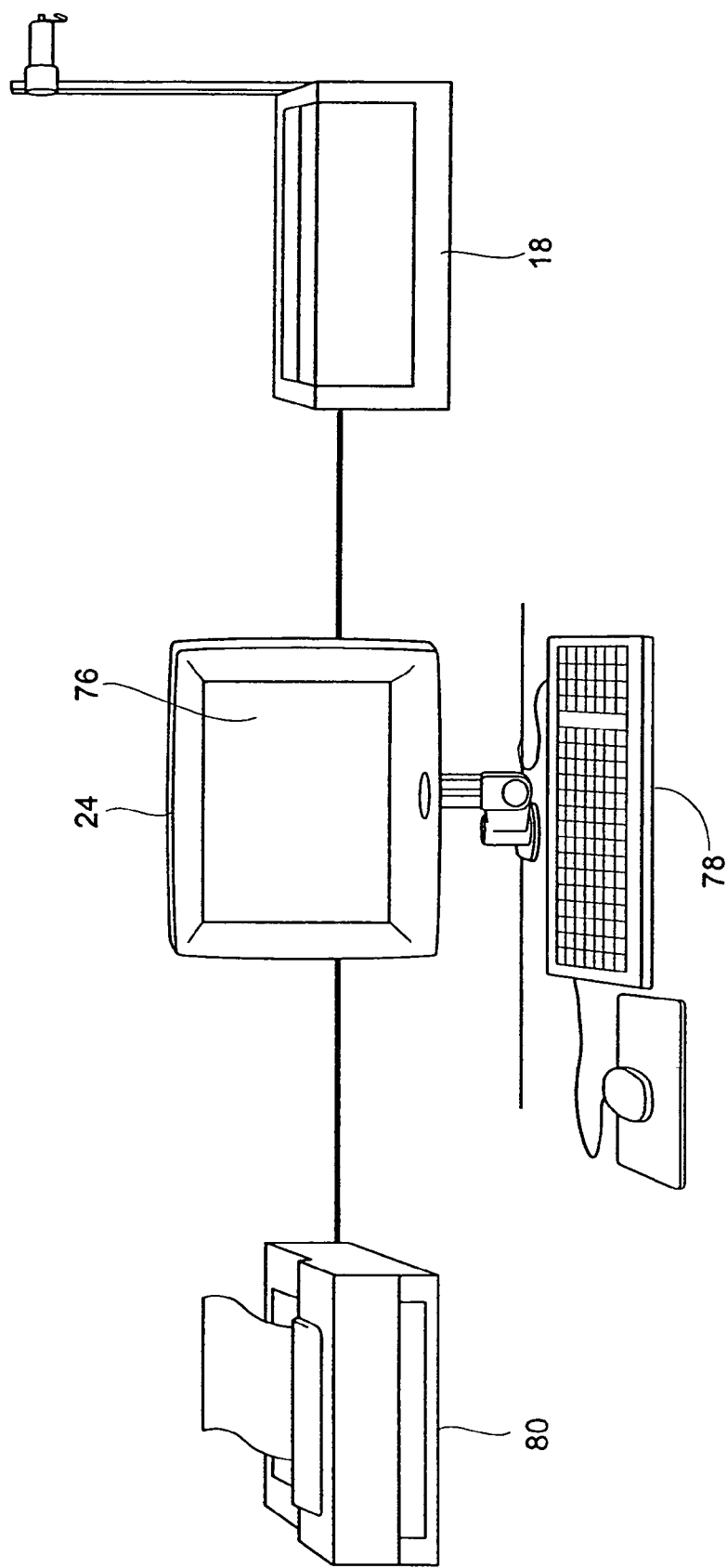
FIGS. 8A to 8F are schematic views of alternative configurations of linked and/or networked systems that incorporate the compounding device shown in FIG. 1.
Figure 8B:
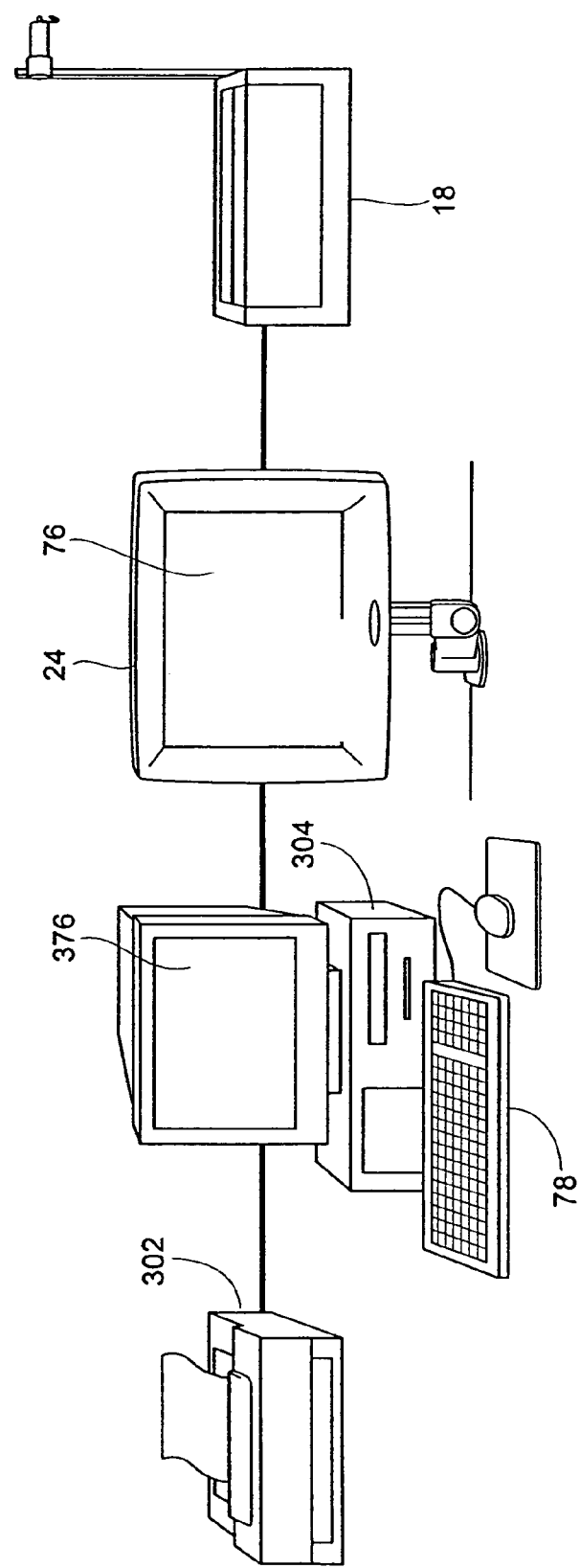
Figure 8C:
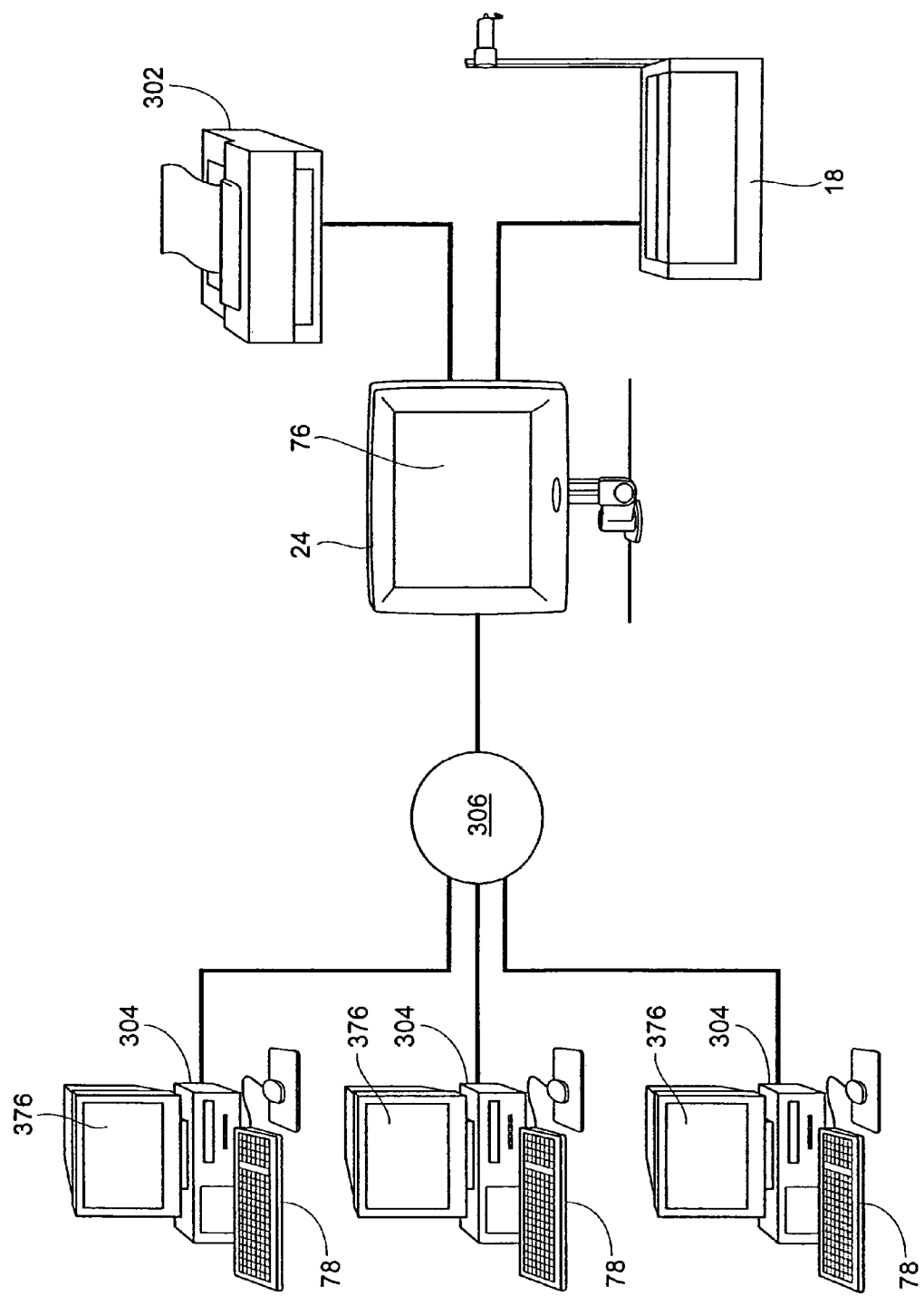

The order entry process manager 84 desirably receives data input through keyboard/mouse devices 78, and provides data output either through the display screen 76 of the control panel 24 (as shown in FIG. 8A), or a separate, dedicated display device 300 (as shown in FIGS. 8B to 8F). The order entry process manager 84 also is desirably linked to a printer 302, for providing reports and labeling in paper form.

The order entry process manager 84 can be developed to generate its own proprietary user interface (like the compounding control manager 72). Desirably, however, the order entry process manager 84 is developed in a graphics-based environment (e.g., Windows®, Linux®, etc.) using, e.g., an Apache® or Java® Operating Environment that can be used in association with conventional web-server or browser software 86, such as Microsoft® Internet Explorer, Netscape® Navigator, or an equivalent public accessible browser. In this arrangement, the order entry process manager 84 desirably comprises the program language that provides the operator with real time feedback and interaction with the controller 20 of the compounding device through browser-based graphic user interface (GUI) elements. The browser-based GUI elements allow an operator to input and adjust the information used by the compounding control manager 72 to operate the compounding device. This makes possible the linkage of the proprietary compounding control manager 72 of the compounding device to one, several, or an entire network of conventional browser data entry and output platforms, which can comprise a single local site or a network of remote sites. Implemented in this manner, the order entry process manager 84 and browser software 86 make fully networked compounding possible. Furthermore, the order entry process manager 84 makes possible a network appliance function, whereby all an authorized operator has to do is couple a browser to the MPU 58 of the compounding device 18 to be able to control the compounding device 18. The network appliance function significantly enhances the usability and flexibility of the compounding device 18.

To develop the browser-based GUI elements, the order entry process manager 84 utilizes certain third party, off-the-shelf components and tools, available in e.g., Apache® or Java® Operating Environments. Once developed, the order entry process manager 84 can reside as a software program on a memory device. The order entry process manager 84 can be accessed by a laptop or desktop workstation computer, PDA device, or any other device that can run a browser, to provide different order entry platforms.

C. Associations with the Compounding Control Manager

The order entry process manager 84 and browser software 86 accommodate diversely different associations with the compounding control manager 72 installed on the controller 20 of the compounding device 18.

In a basic form (see FIG. 8A), the order entry process manager 84 and browser software can be installed in the MPU 58 in the control panel 24 of the compounding device 18, to constitute a single control panel configuration. In this arrangement, the display device 76 on the control panel 24 supports the browser-based interface of the order entry process manager 84 for order entry to the compounding device and label printing, as well as supporting the proprietary touch screen interface of the compounding control manager 72 during operation of the compounding device.

In another arrangement (see FIG. 8B), the browser software 86 can be installed on a data entry workstation 304 positioned in the same facility as the compounding device 18. The data entry workstation 304 can be placed near the compounding device 18, or it can be physically separated from the compounding device within the facility. In this arrangement, the browser software 86 of the data entry workstation 304 is linked, e.g., via a hubless local area network connection to the order entry process manager 84 residing in the MPU 58 in the control panel 24 of the compounding device 18, to constitute a single data entry station configuration. In this arrangement, the display device 300 of the data entry workstation 304 supports the browser-based interface of the order entry process manager 84 for order entry to the compounding device and label printing. The display device 76 of the control panel 24 supports the proprietary touch screen interface of the compounding control manager 72 during operation of the compounding device 18.

In another arrangement (see FIG. 8C), the browser software 86 can be installed on several data entry workstations 304 positioned in the same facility as the compounding device 18. The browser software 86 of the data entry workstations 304 can be linked, e.g., via a hub 306 or switch as a local area network to the order entry process manager 84 residing in the MPU 58 in the control panel 24 of the compounding device 18, to constitute a multiple data entry station configuration. In this arrangement, the display device 300 of each data entry workstation 304 supports the browser-based interface of the order entry process manager 84 for order entry to the compounding device 18 and label printing by the printer 302. A single compounding device 18 can thereby be linked to several order entry workstations 304. The display device 76 on the control panel 24 of the compounding device 18 supports the proprietary touch screen interface of the compounding control manager 72 during operation of the compounding device.

Figure 8D:
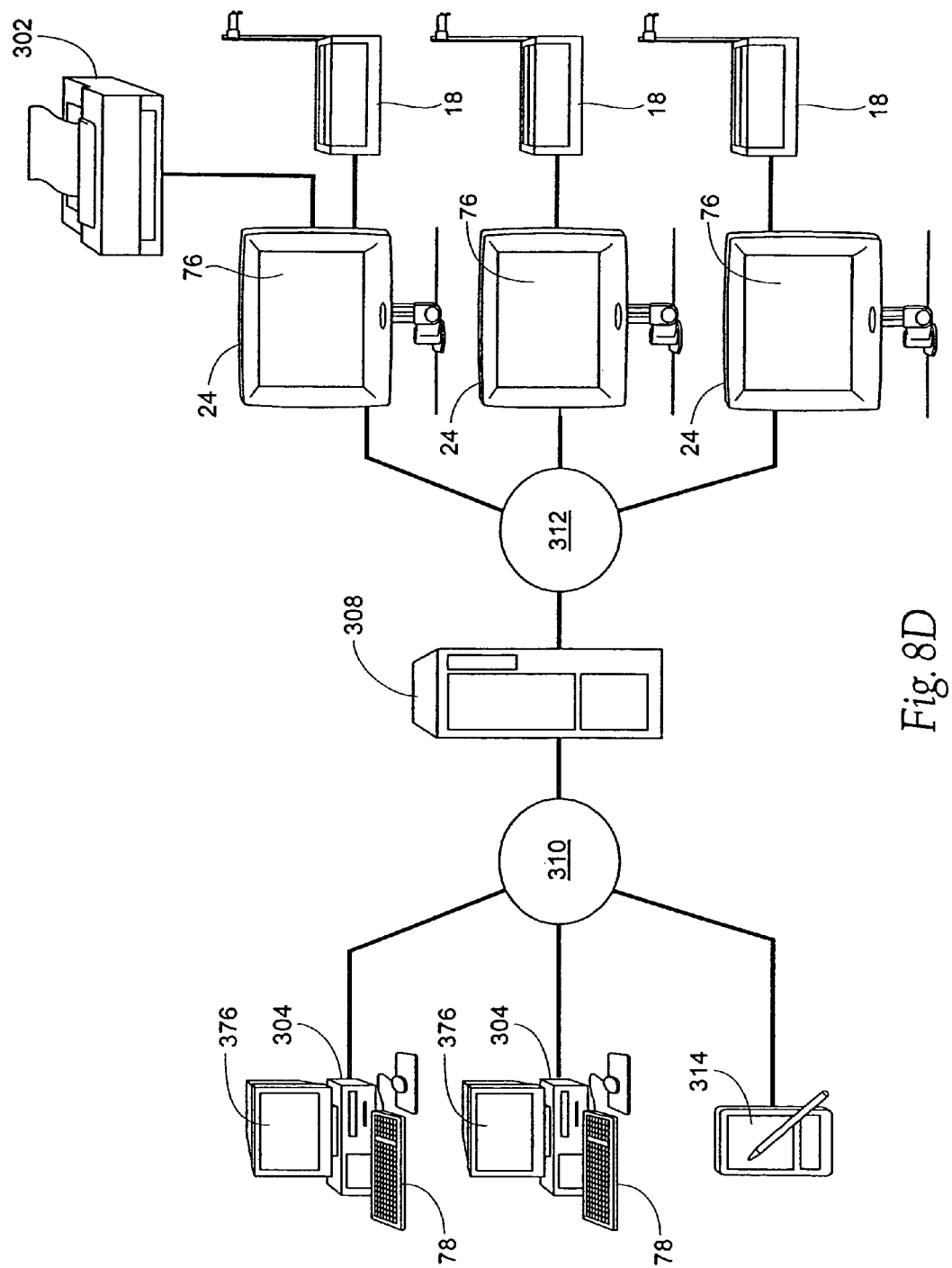

In another arrangement (see FIG. 8D), the browser software 86 can be installed on several data entry workstations 304 positioned in the same facility as several compounding devices 18. The browser software 86 of the data entry workstations 304 can be linked, e.g., via a server 308 to form an intranet facility network 310, and the order entry process manager 84 residing in the MPU's 58 in the control panels 24 of the several compounding devices 18 can be linked to the server 308 via a hub 312, to constitute a fully networked data entry, multiple compounding station configuration. In this arrangement, the display device 300 of each data entry workstation 304 supports the browser-based interface of the order entry process manager 84 for order entry to the compounding device 18 and label printing by the printer 302. Multiple compounding devices 18 can thereby be linked to multiple order entry workstations 304. The display device 76 in the control panel 24 of each compounding device 18 supports the proprietary touch screen interface of the compounding control manager 72 during operation of the respective compounding device. As shown in FIG. 8D, the browser software can be installed in a PDA device 314, or any other device that can run a browser, to provide different order entry platforms.

In another arrangement (see FIG. 8E), the browser software 86 can be installed on one or more data entry workstations 304 positioned in a data entry facility 316 that is remote to another facility 318 where one or more compounding devices 18 are located. The browser software 86 on one or more data entry workstations 304 at the remote data entry facility 316 can be linked to the order entry process manager 84 residing in the MPU(s) 58 in the control panel(s) 24 of the compounding device(s) 18 at the remote compounding facility 318 via the public internet 320. Of course, other forms of remote linkage can be used. The browser software 56 can be installed, alone or with the installation on the remote workstations 304, on one or more data entry workstations 304 at the local compounding facility 318, and also linked to the order entry process manager 84 in the MPU(s) 58 in the control panel(s) 24 of the compounding device(s) 18 via the public internet 320. If the facilities 316 and 318 are part of a common operating entity, the order entry process manager 84 and browser software 56 can be installed on a data collection/administration workstation 304 positioned in a data center facility 322 that is remote to both the data entry and compounding facilities 316 and 322. The data center 322 maintains an information data base 324 of patient information and compounding resources for the compounding facility 318, and also be linked to the data entry facility 316 and the compounding facility 318 via the public internet 320.

Figure 8E:
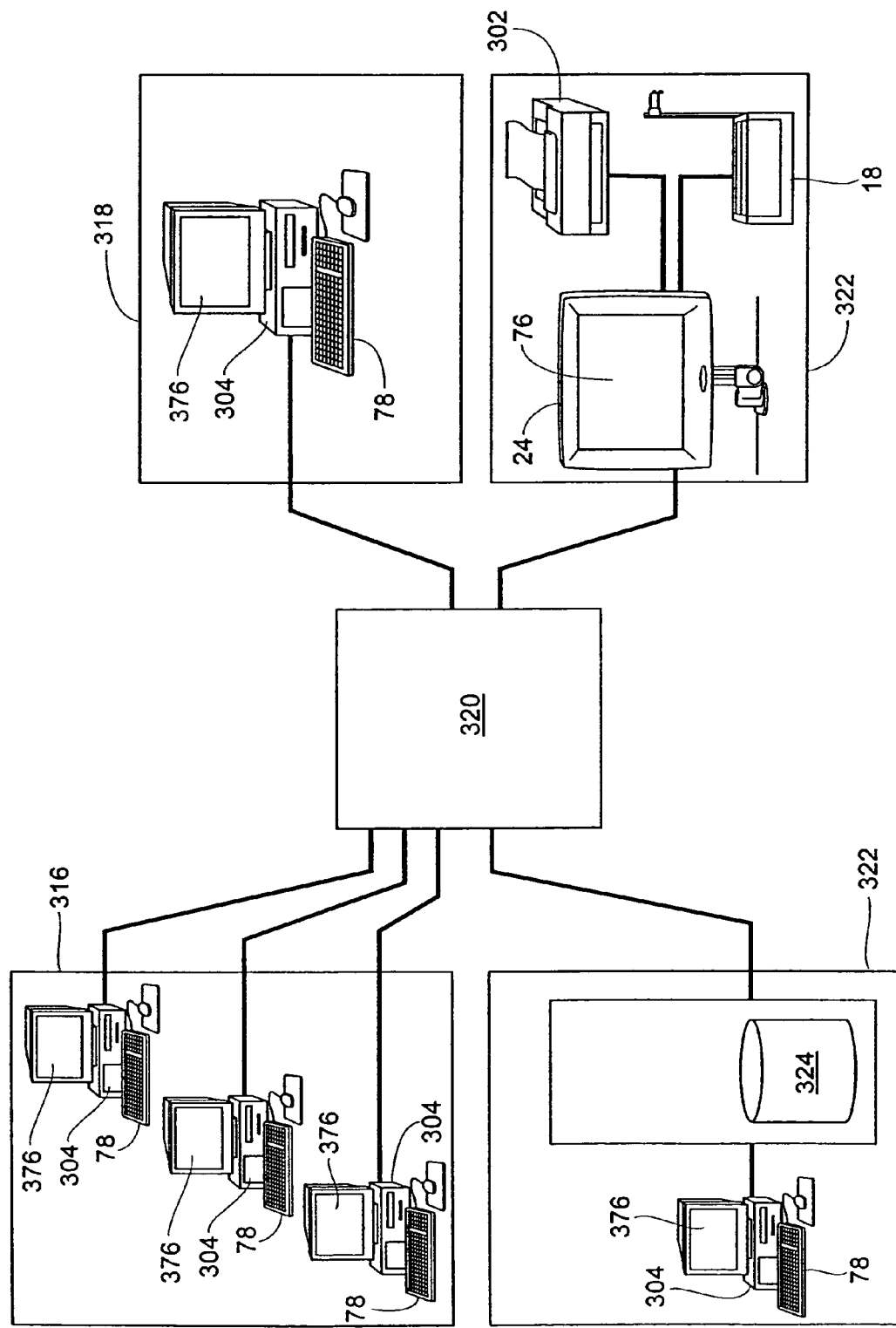
Figure 8F:
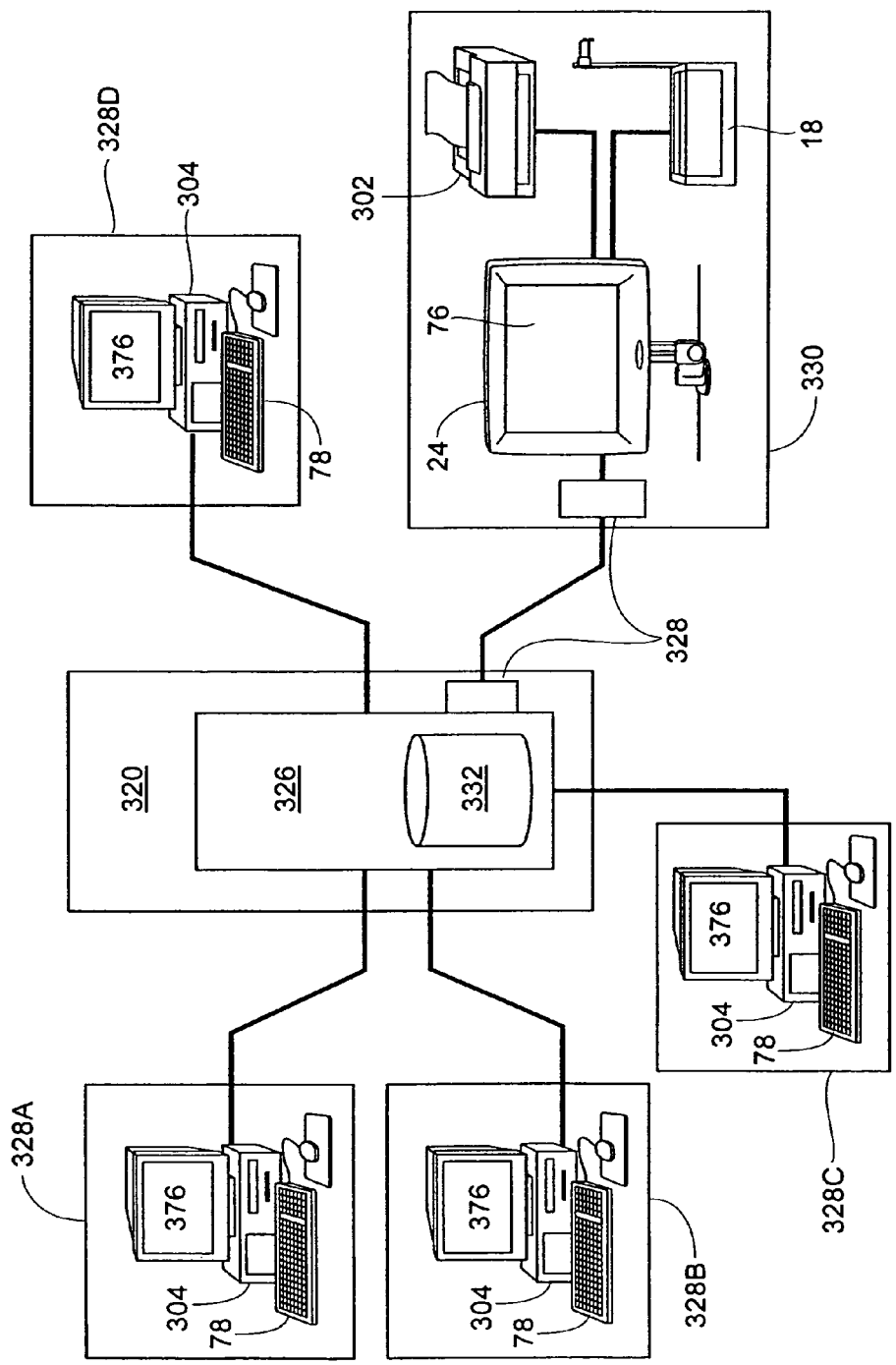

In a variation to the arrangement shown in FIG. 8E (see FIG. 8F), a host data entry service facility 326, where the order entry process manager 84 is installed, can be coupled via the public internet 320 to one or more remote data entry facilities 328A, 328B, 328C, 328D. The host data entry service facility 326 can also be linked via a virtual private network 328 through the public internet to a remote compounding facility 330, where the compounding control manager 72 is installed in the MPU 58 in the control panel 24 of the compounding device 18. The browser software 86 is installed on the data entry workstations 304 positioned in the remote data entry facilities 328A to 328D. The host data entry service facility 326 maintains the data collection and management data base 332 for the entire network. In this way, multiple order entry facilities 328A to 328D can be linked to a single compounding facility 330 via an intermediary service facility 326, which can also maintain a central collection and management data base 332.

B. Features of the Order Entry Process Manager

Figure 10A:
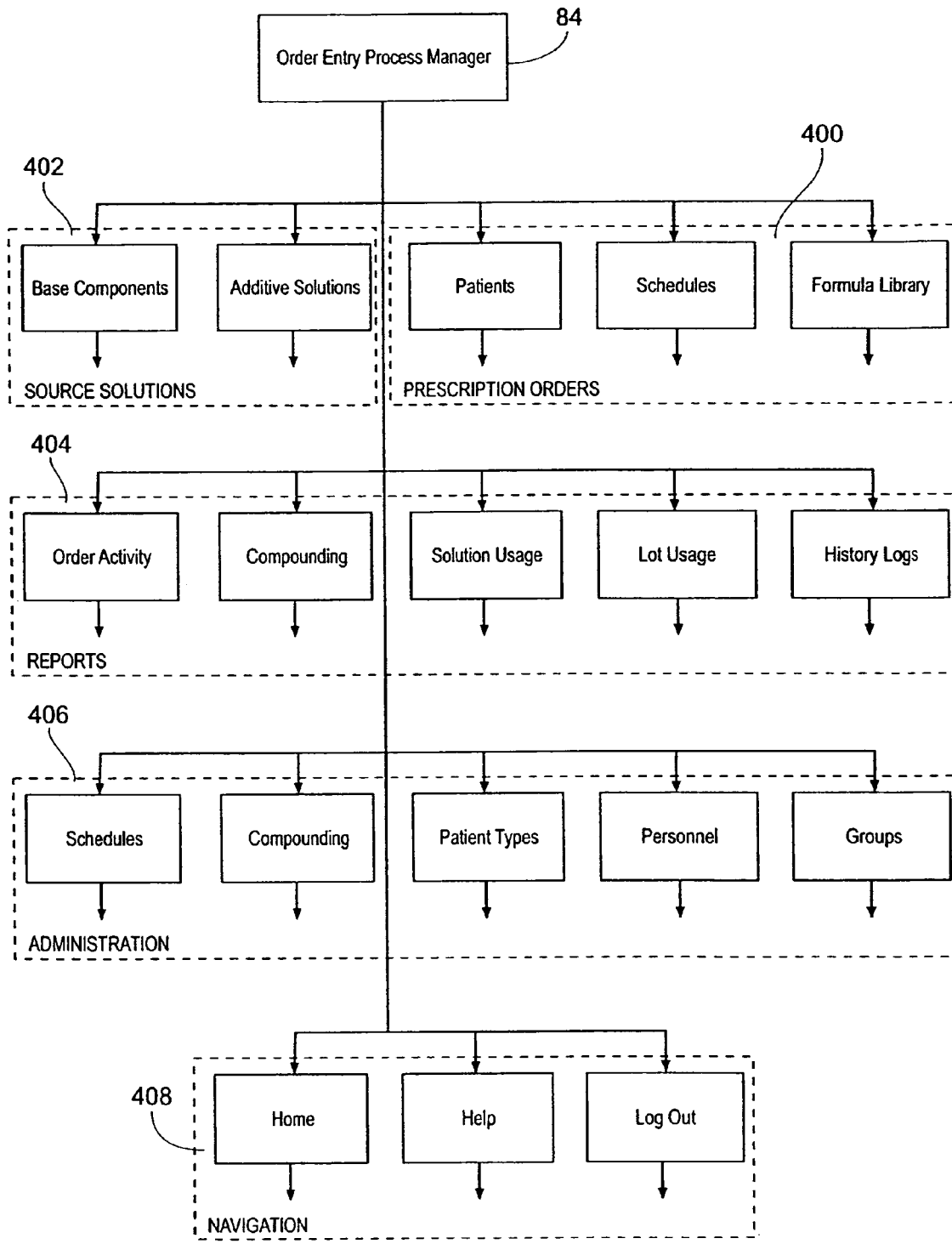
FIGS. 10A to 10E are system flow charts of representative functional modules of an order entry process manager function that, when used in association with the compounding control manager function of the compounding device shown in FIG. 1, provides enhanced compounding order entry and processing capabilities that can be accessed by browsers installed on remote workstations.

FIG. 10A shows a general schematic representation of the operator-selectable functional modules that a representative implementation of the order entry process manager 84 can possess. As illustrated, these functional modules include a prescription order module 400, a source solution module 402, a reports module 404, an administration module 406, and a navigation module 408. The prescription order module 400 allows an operator to enter a prescription order for a given patient, with reference to a preexisting compound formula or to a new compound formula, as well as schedule the order for compounding. The source solution module 402 maintains an inventory of available base source solutions and additive source solutions that are cross-referenced in the formula library of the prescription order module 400. The reports module 404 provides an operator the capability of tracking compounding activities and generating various administrative reports relating to these activities. The administration module 406 aids the operator in the performance of various administration tasks in support of the compounding activity. The navigation module 408 assists the operator in use of the order entry process manager 84. Each module contains one or more functional components that an operator can select in using the module, as will be described in greater detail later.

A given operator can gain access to one or more of these functional modules, depending upon the access options that the system administrator grants a given operator, which depends upon the functions that the operator is required to perform. For example, a hierarchy of access options can be specified for use by a physician or pharmacist, who specifies or enters compounding orders; a compounding activity administrator, whose function is to oversee the compounding function from an administrative standpoint; and a compounding technician, whose function is to operate one or more compounding devices 18. The available functional modules can be displayed as menu box selections on a main screen or home page, which opens once a given operator identifies itself by name and assigned password on an appropriate log-on screen.

Figure 11A:
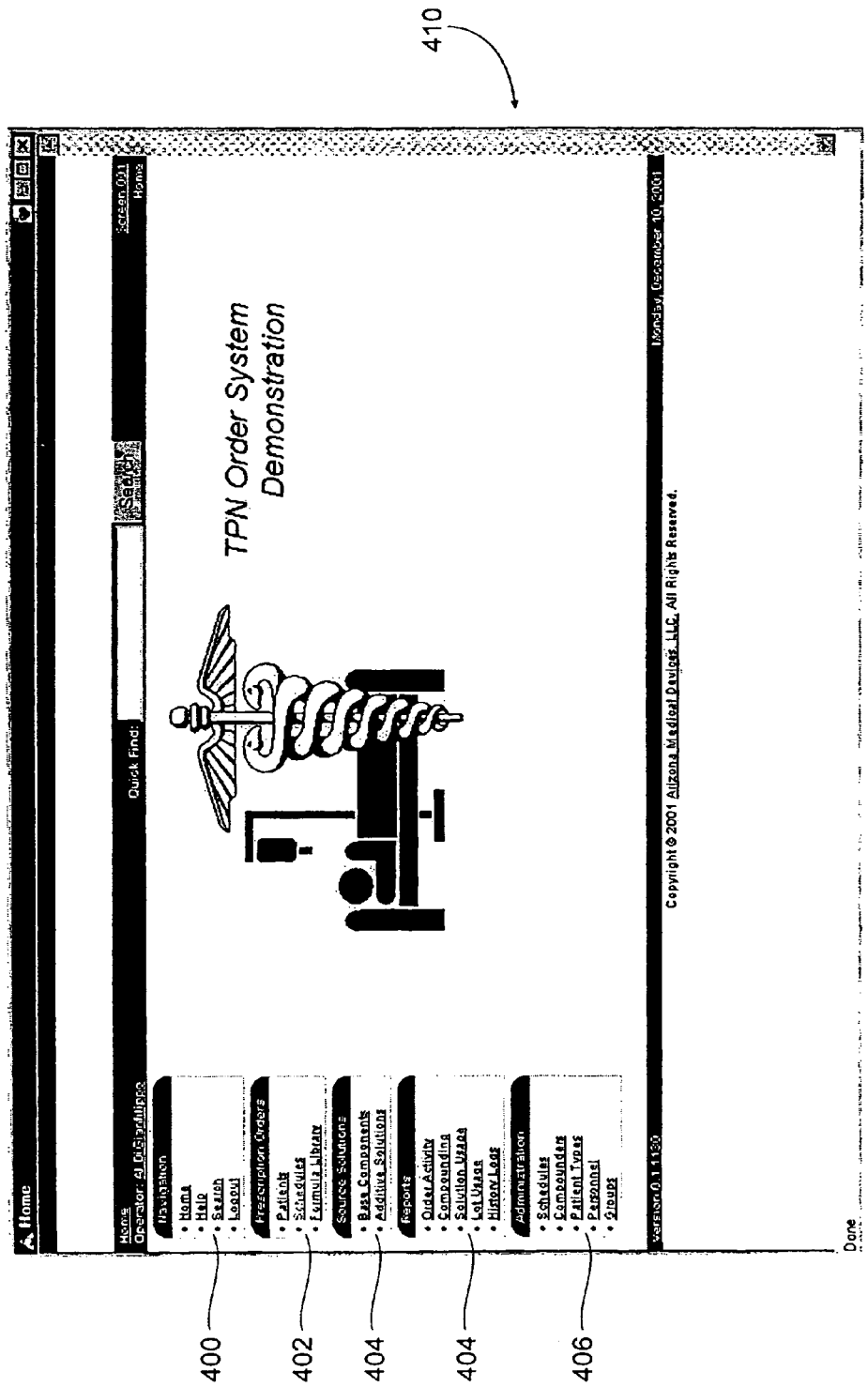
Figure 11B:
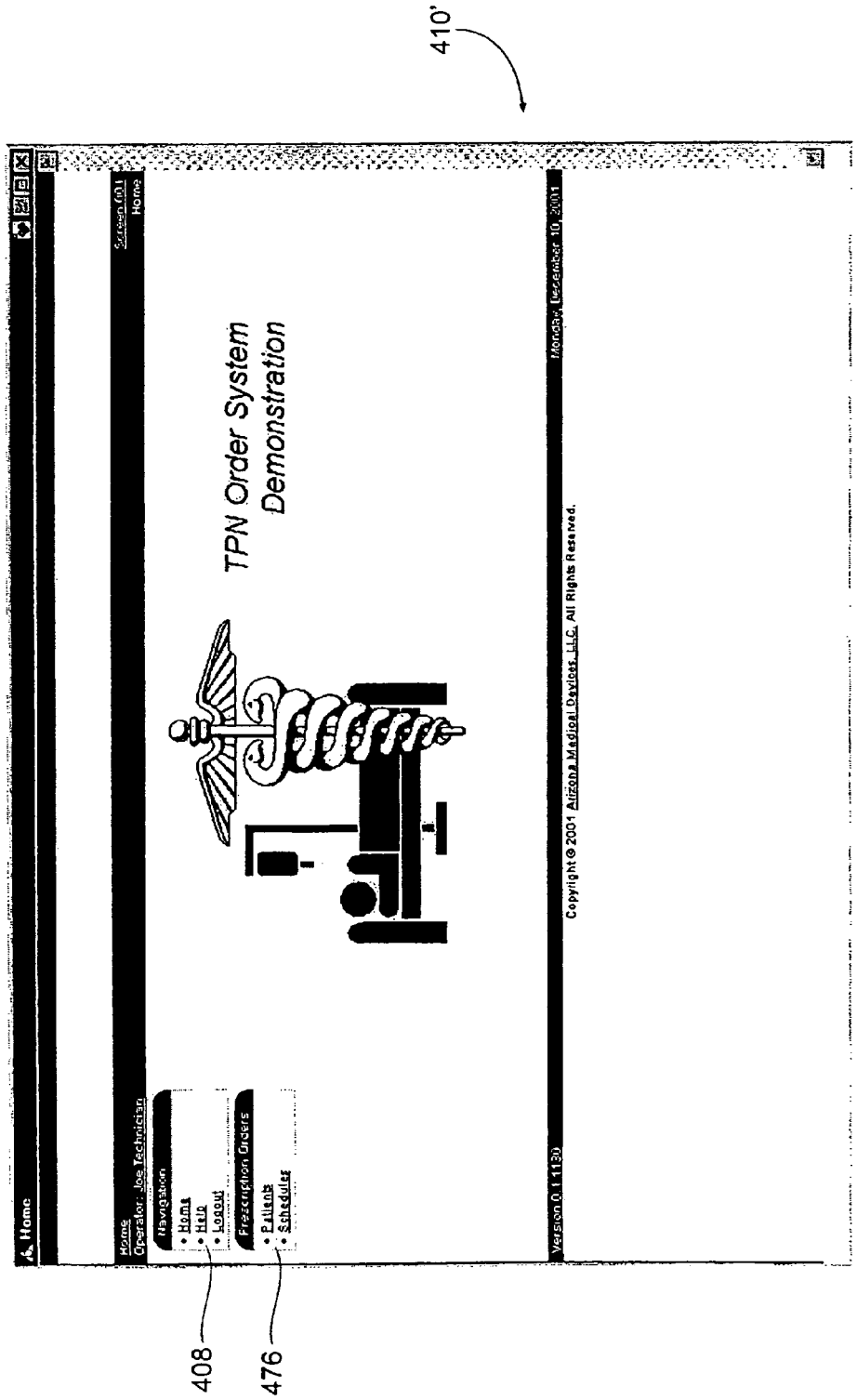

For example, FIG. 11A shows a representative main screen or home page 410 for an operator who has a physician or pharmacist access option. As FIG. 11A shows, all functional modules 400 to 408 are available for selection at this access level, because performance of that person's function may require access to all features of the order entry process manager 84. As a comparative example, FIG. 11B shows a representative main screen or home page 410' for a compounding technician, which offers access to a lesser selection of functional modules, because the technician's function does not require access to all the functional features of the order entry process manager 84. The functional module menu boxes which a given individual may access may appear in a column along the left side of other screens generated by the order entry process manager 84.

Figure 10B:
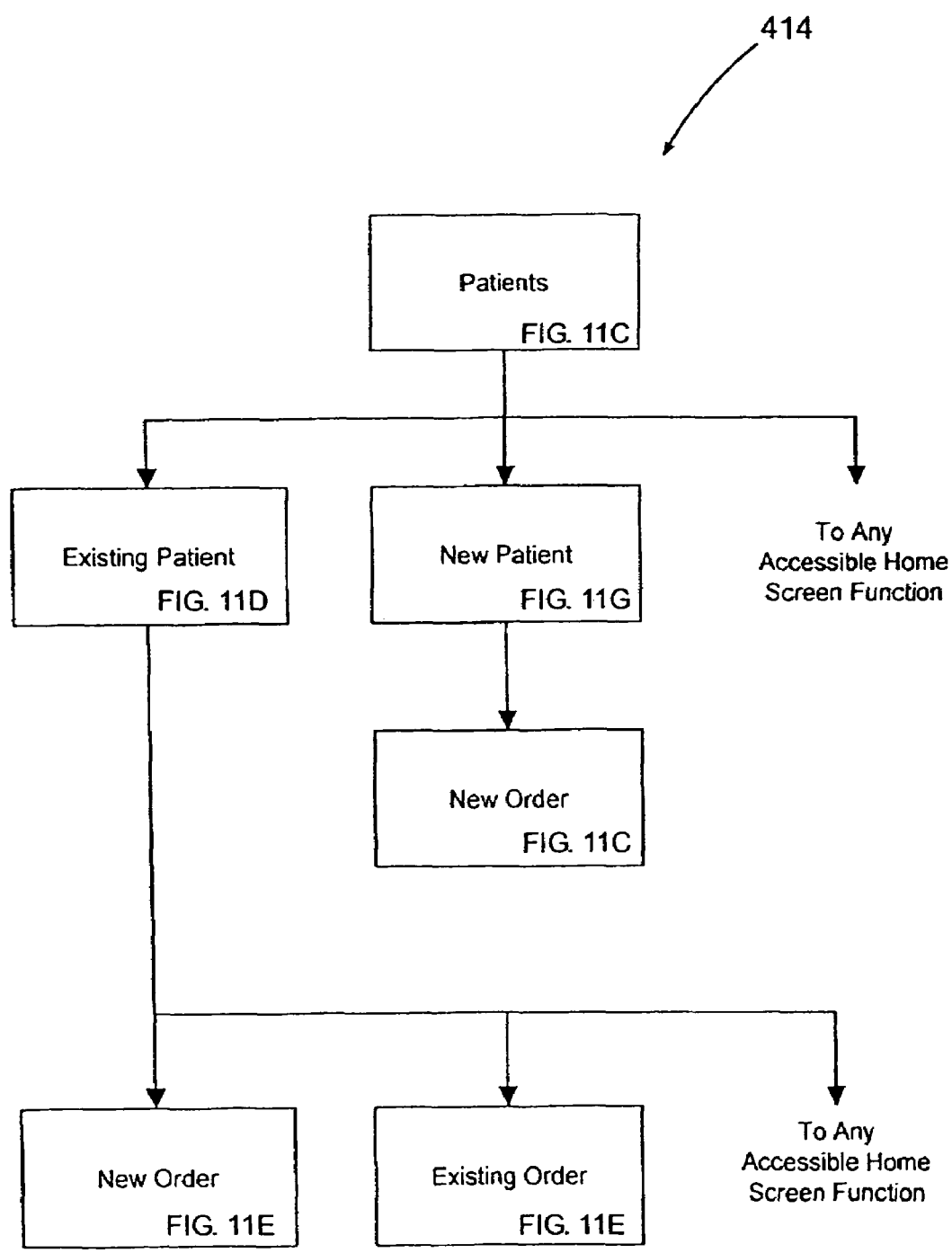

Assuming that the operator is at a physician or pharmacist access level, and is thereby viewing the home page shown in FIG. 11A, the operator can, with a mouse click, select a desired functional module. Assuming the operator seeks to enter a prescription order for a given patient, the operator mouse-clicks on the Patients component of the PRESCRIPTION ORDER menu box 400, which opens the PATIENT MAIN PAGE 412 shown on FIG. 11C. This window 412 provides access to the features of the Patient Data Base Component 414 of the order entry process manager 84, the functional units of which are shown schematically in FIG. 10B.

The Patient Data Base Component 414 allows a user to either select an existing patient by a last name search of a list of patient information files created in a patient information data base maintained by the order entry process manager 84 (FIND A PATIENT box field 416), or by entering the name of a new patient (ENTER NEW PATIENT box field 418).

Figure 11C:
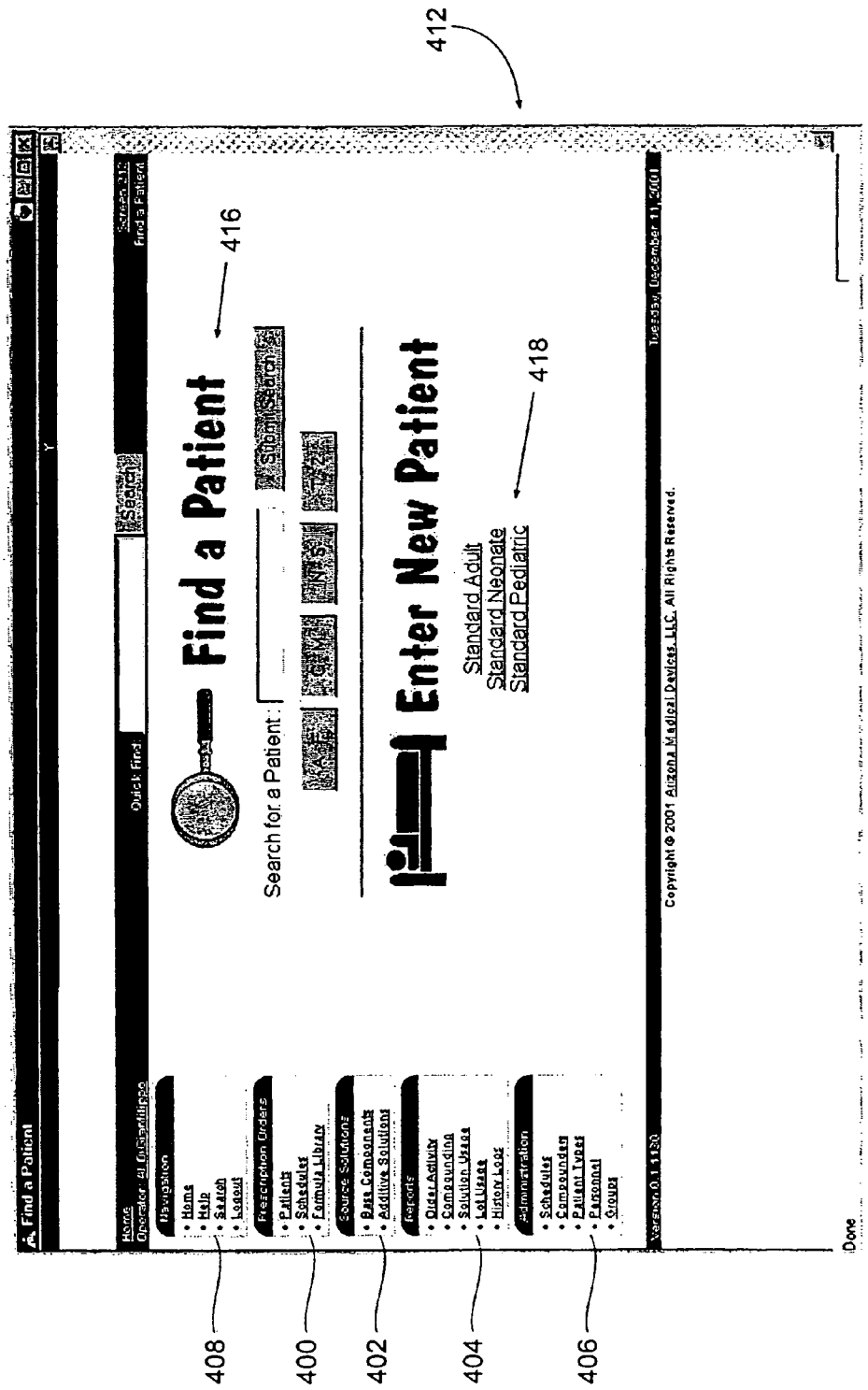
Figure 11D:
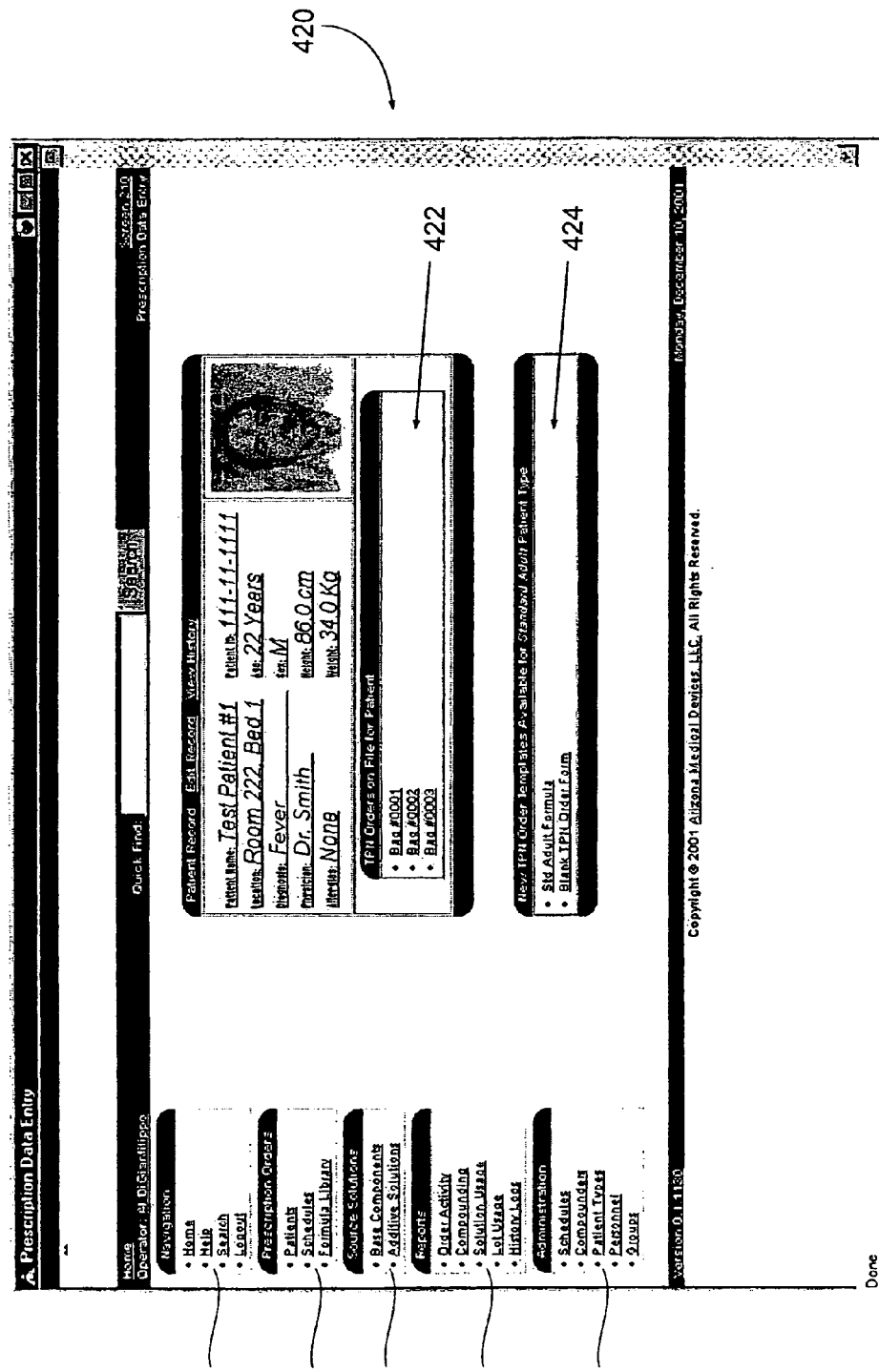

Upon finding an existing patient's name, the order entry process manager 84 provides a window displaying the contents of the corresponding Patient Information Record 420 (FIG. 11D). The Patient Information Record 420 allows the operator to enter a new compounding order, based upon previous compounding orders retained in the patient data base for that patient (TPN ORDERS ON FILE FOR PATIENT box field 422), or allows the operator to enter a new compounding order for that patient based upon a standard default templates for a patient type that the patient matches (NEW TPN ORDER TEMPLATES AVAILABLE FOR STANDARD ADULT PATIENT TYPE box field 424).

Figure 10C:
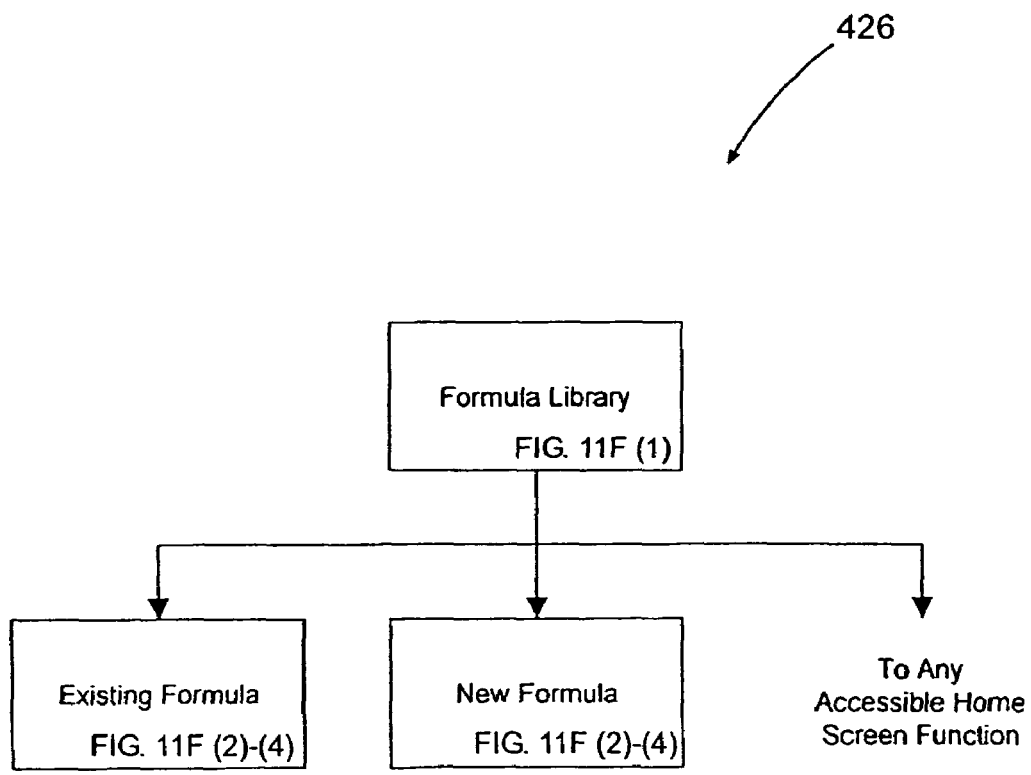

The PRESCRIPTION ORDER MENU box 400 includes a Formula Library component. When selected, the Formula Library component provides access to the features of the Formula Library Data Base Component 426 of the order entry process manager 84, the functional units of which are shown schematically in FIG. 10C. Selection of the Formula Library component opens a Formula Library web page 432 shown in FIG. 11F(1). The Formula Library web page 432 permits the operator to select an existing default formula template for display and selection in the Patient Information Record page 420, or to add a new formula template for display in the Patient Information Record. Selection of template opens a scrollable Order Template web page 434 shown in FIGS. 11F(2), 11(3), and 11F(4), that allows the operator to specify base components (types and amounts) and additive solutions (types and amounts) for a template formula. Default data in an existing template formula can also be changed and submitted. The Order entry process manager 84 computes the nutritional requirements of the template formula based upon the selected types and amounts of base components and additives, drawing upon data contained in the source solutions module 402, as will be described in greater detail later.

Figure 11E:
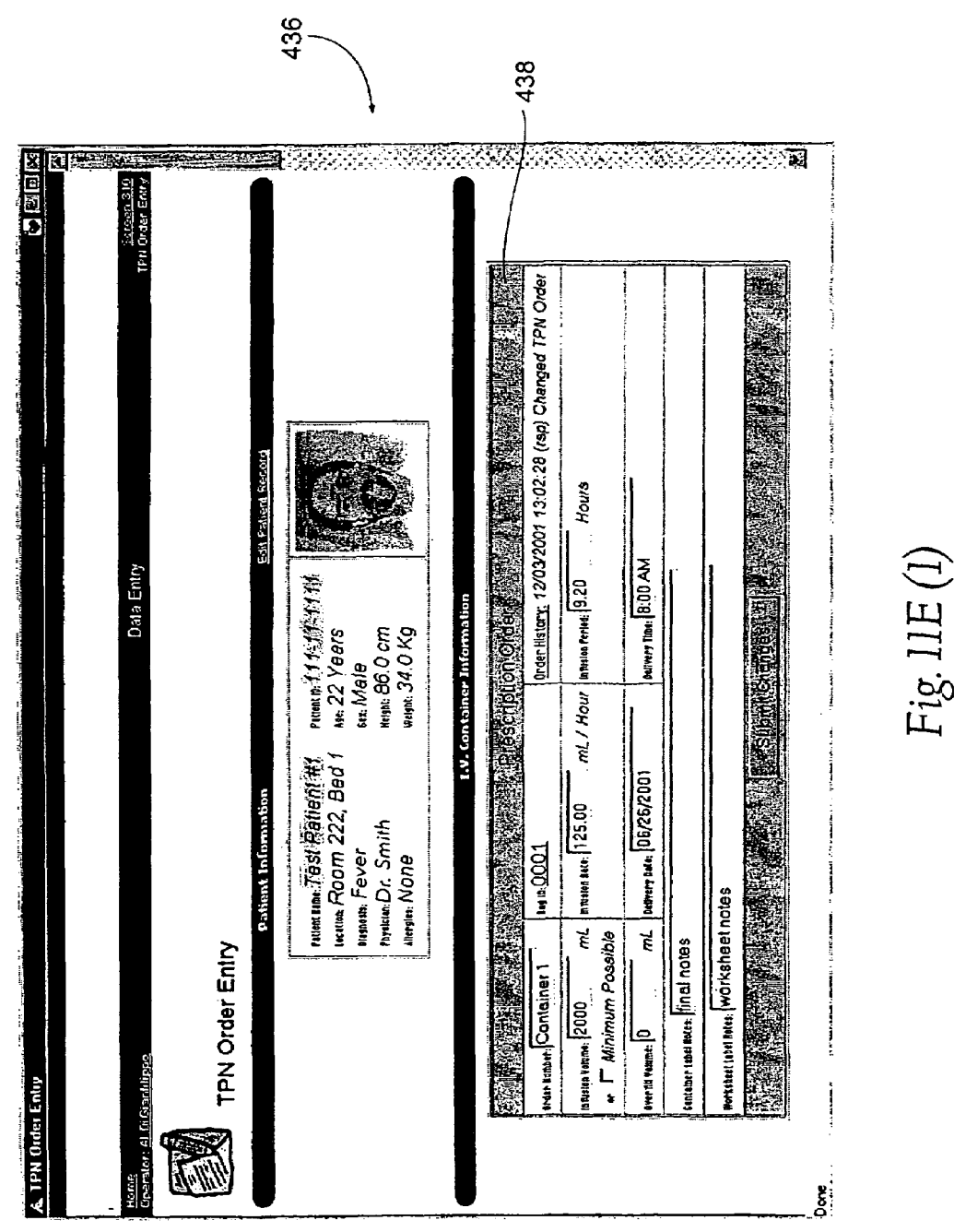
Figure 11E:
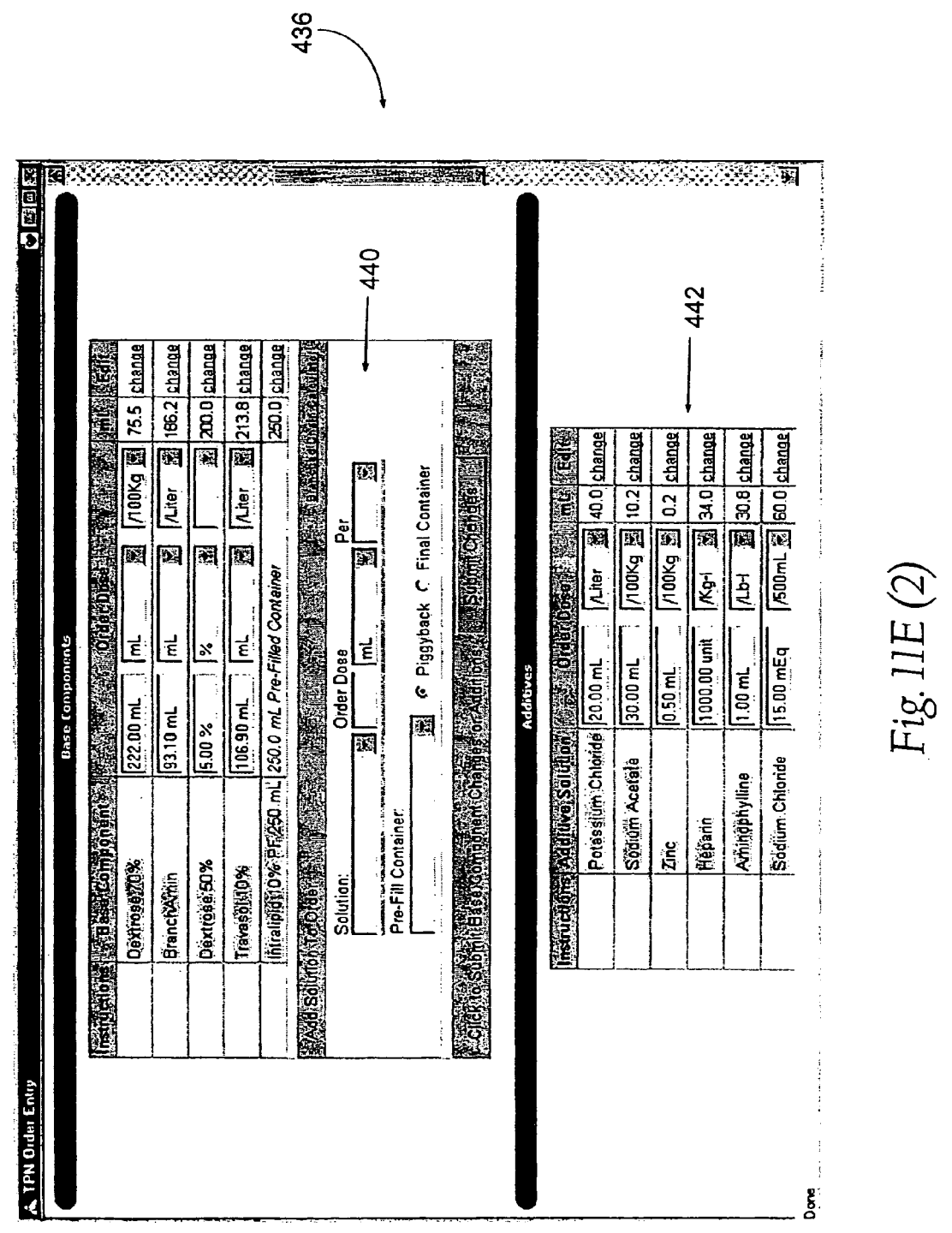
Figure 11F:
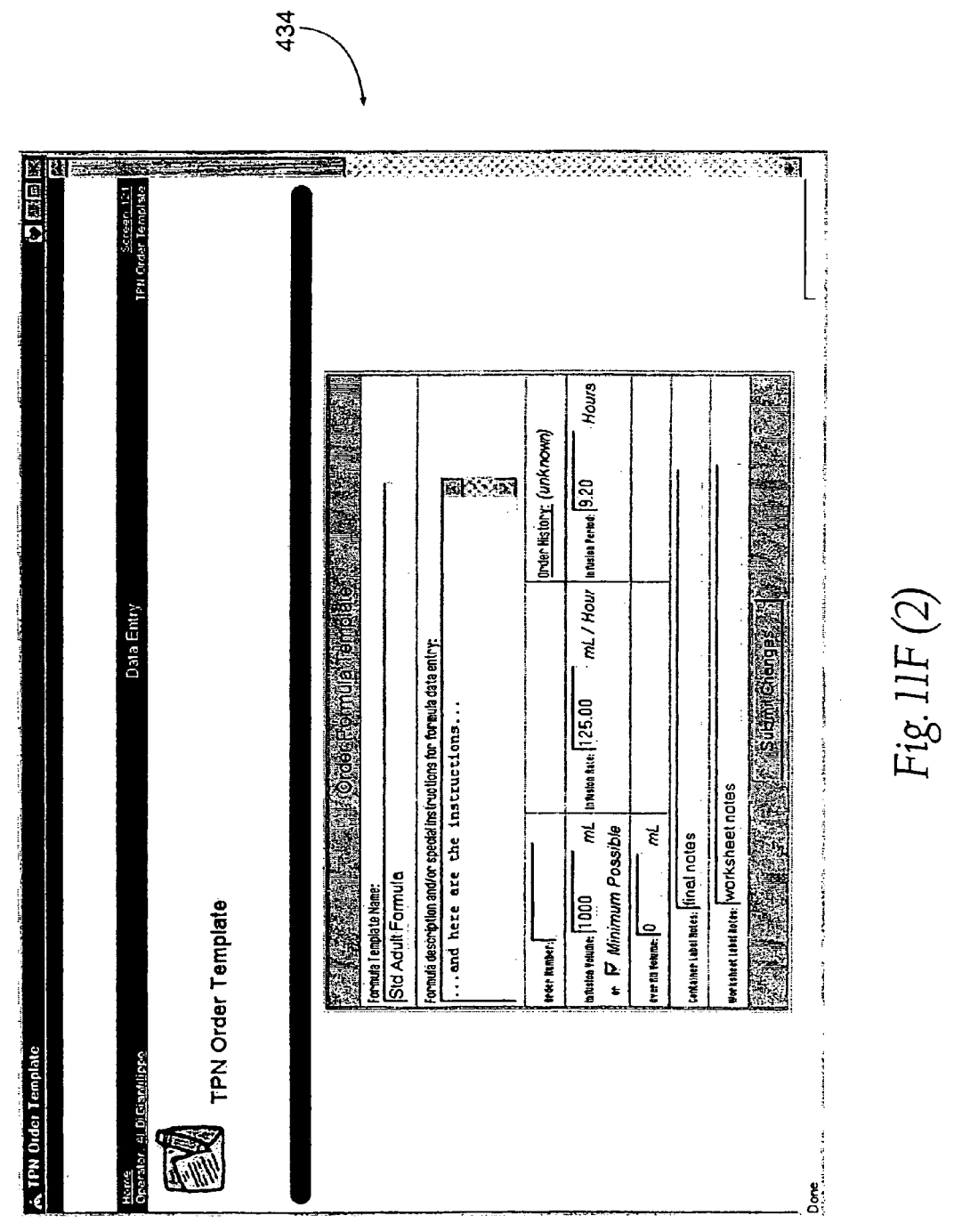
Figure 11F:
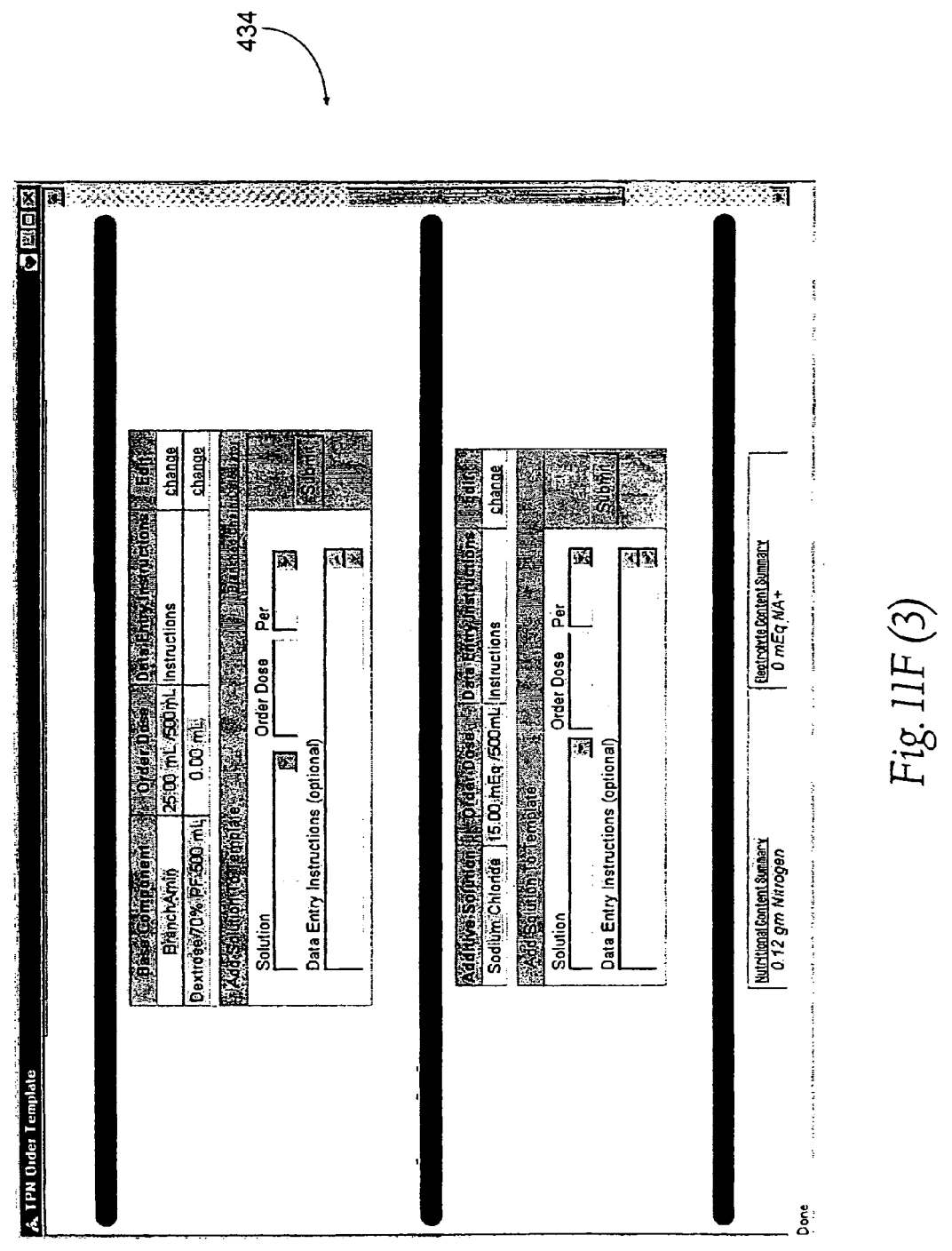
Figure 11F:
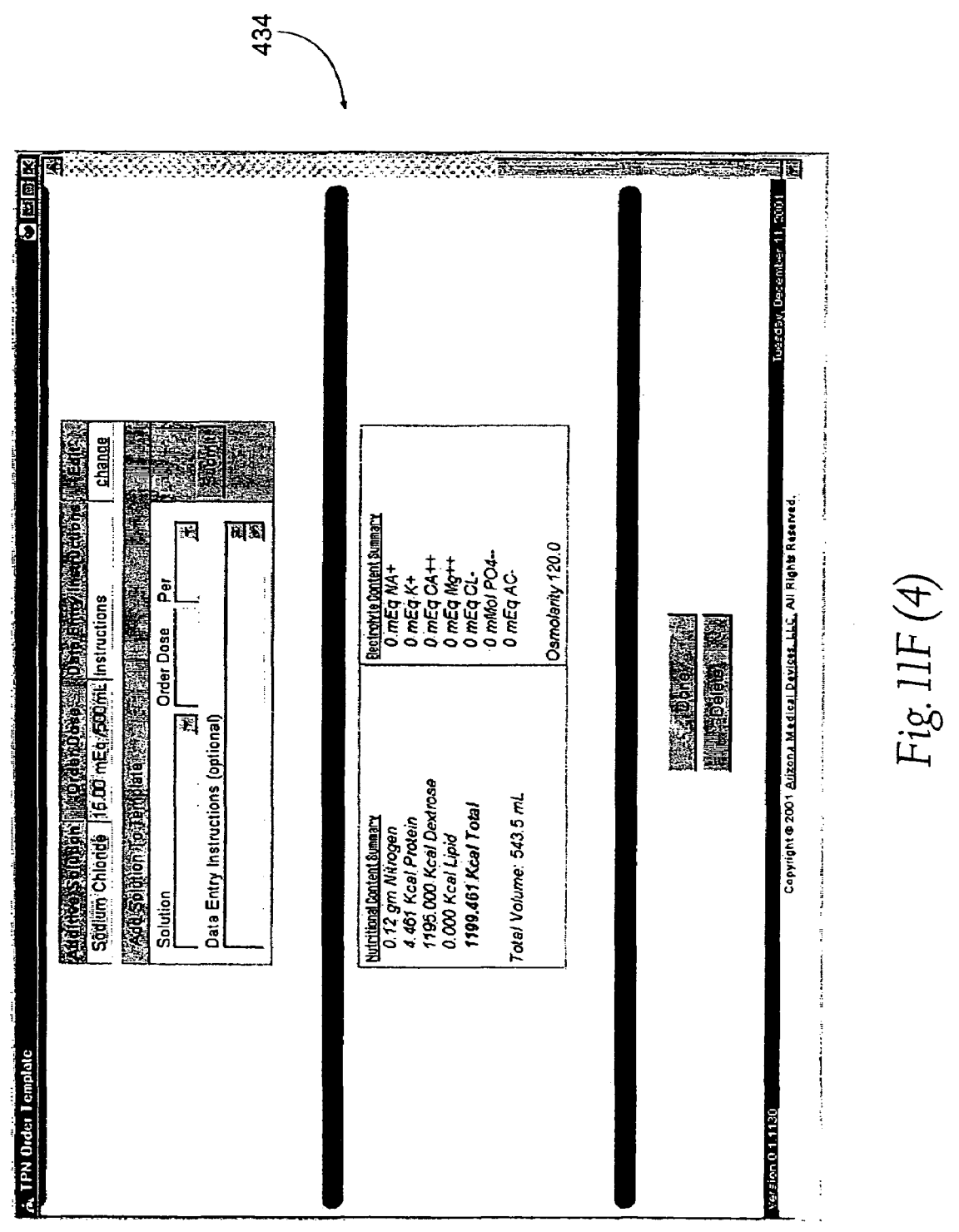

A mouse click selecting one of the order options 422 or 424 on the Patient Information Record opens a scrollable Order Entry window 436 (FIGS. 11E(1) to 11E(4). The Order Entry window 436 includes field boxes that contain details of the PRESCRIPTION ORDER (box 438), the BASE COMPONENTS included in the order (type and amount) (box 440), the ADDITIVES included in the order (type and amount) (box 442), the NUTRITIONAL SUMMARY (based upon the types and amounts of the base components and additives included in the order) (box 444), and the ORDER STATUS (which will be described later) (box 446). The default listing of solutions and solution amounts in the BASE COMPONENTS and ADDITIVE field boxes 440 and 442 are provided based upon the selection on the Patient Information Record 420 to base the order upon a previous order or a standard template. The default BASE COMPONENTS and ADDITIVES can be edited to change the previous order or template type and/or amount, or they can be submitted without change. The Order entry process manager 84 computes the NUTRITIONAL REQUIREMENTS (box 444) based upon the selected types and amounts of base components and additives, drawing upon data contained in the source solutions module 402.

Figure 11G:
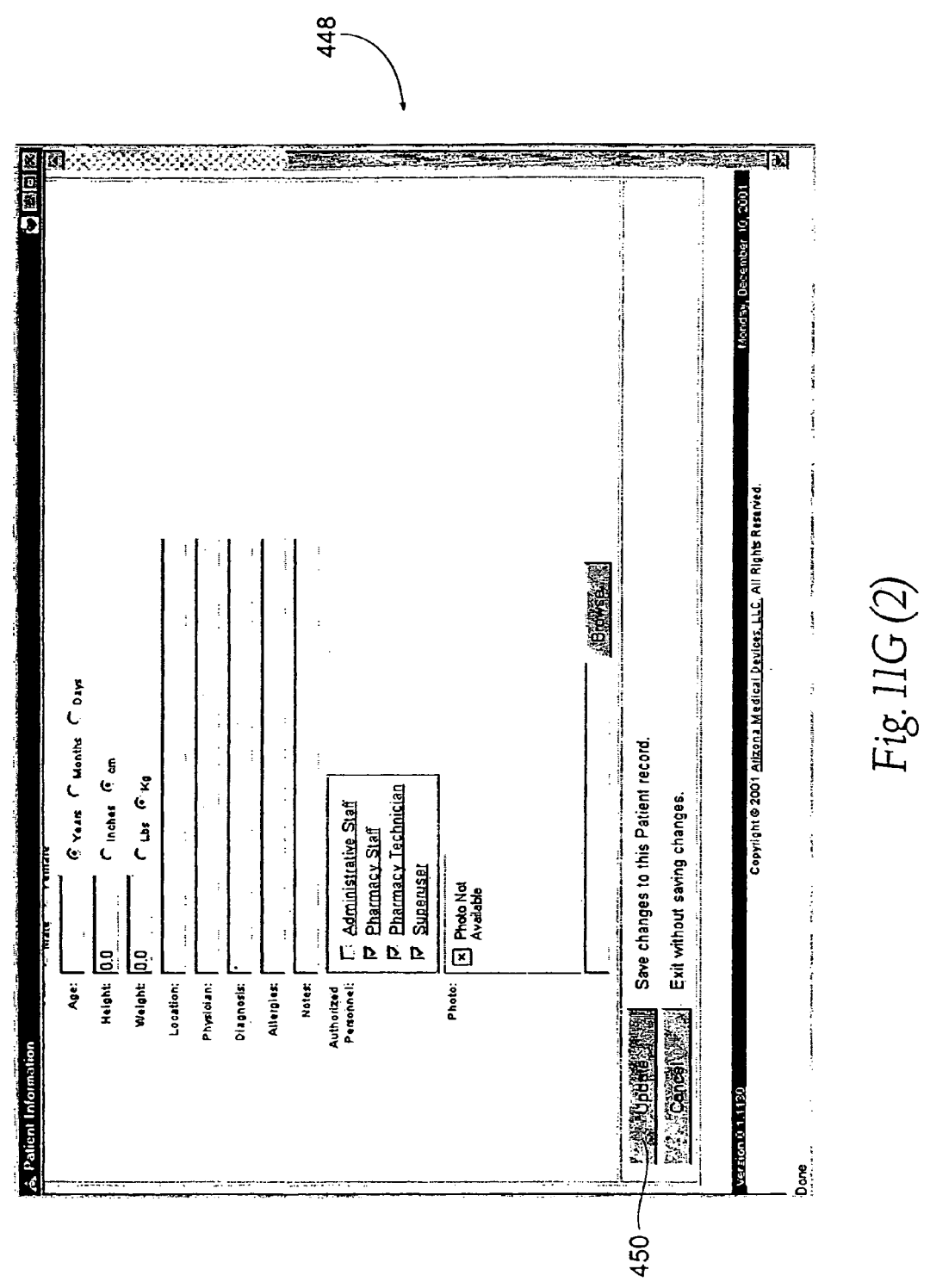

The operator can open the Order Entry window (FIGS. 11E(1) to 11E(4)) to enter a compounding order for a new patient (i.e., a patient not previously entered into the patient data base) by selecting ENTER A NEW PATIENT field box 418 on the Patient Main Web Page 412 (FIG. 11C). With this selection, the order entry process manager 84 opens a window displaying a New Patient web form 448 (FIGS. 11G(1) and 11G(2), prompting the operator to enter data pertaining to the new patient. Upon entry of the new patient information, the operator saves the information to the patient data base (selecting the UPDATE field box 450—shown in FIG. 11G(2)), at which time the scrollable Order Entry window 436 opens for entry of the compounding order (FIGS. 11E(1) to 11E(4).

The last screen of the Order Entry window 436 (FIG. 11E(4) includes an ORDER STATUS box 446. The ORDER STATUS box 446 comprises a listing of the functional steps in a compounding operation that must be executed between order entry and delivery of the compounded order to a patient. The ORDER STATUS box 446 also colors or highlights the steps to indicate which steps have been performed and which remain to be performed. The ORDER STATUS box 446 provides a check list of functions that must be performed to carryout the compounding process and, at a glance, informs an operator what function has been performed and what function still needs to be performed. In the illustrated embodiment (FIG. 11E(4)) the function steps listed include OPEN, SUBMITTED, AUTHORIZED, PRINTED, and COMPOUNDED.

The OPEN step entails the opening of the Order Entry window 436, the entry of information making up the compounding order, and the mouse-clicking the OPEN icon 452. In FIG. 11E(4), the OPEN icon 452 is colored or highlighted, to indicate that this step has been accomplished.

The SUBMITTED step entails mouse-clicking the SUBMITTED icon 454, which places the information in the database and thereby makes the Order Entry window containing the pending compounding order available for viewing on any workstation with a proper operator access level, which, in this case, would be a designated authorizing pharmacist. The SUBMITTED icon 454 is colored or highlighted on the Order Entry window 436 when the step has been completed. The order entry process manager 84 desirably keeps track in the database of the compounding orders submitted by the various order entry workstations that are awaiting authorization, so that they can be accessed in an organized fashion by the browser software at the workstation of the authorizing pharmacist. The authorizing pharmacist knows to periodically run the browser software to access this queue of pending orders, to review each pending order, and indicate authorization of each order in the AUTHORIZE THIS ORDER FOR COMPOUNDING field box 456 on the Order Entry window 436.

In another arrangement, the order entry process manager 84 can include a notification function, which provides a pop-up message at the workstation of the authorizing pharmacist to alert the individual that there are entered compounding orders awaiting authorization. Clicking on the pop-up message opens a list of the orders awaiting authorization that the authorizing pharmacist can access.

In the illustrated embodiment, authorization entails clicking the authorization statement (box 458), selecting the shift in which the compounding is to be performed (box 460), and selecting the AUTHORIZE FOR COMPOUNDING icon 462. A STAT ORDER icon 464 is provided if the compounding order is to be performed as soon as possible. The AUTHORIZED icon 466 is colored or highlighted on the Order Entry window 436 when the authorization step has been completed.

The order entry process manager 84 desirably keeps track of the compounding orders that are in the database that have been authorized and are awaiting the printing of labeling, so that this subset of orders can be accessed in an organized fashion at a workstation where printing occurs. These compounding orders are accessed at the workstation where labeling for the final solution container 14 is to be printed.

In another arrangement, the order entry process manager 84 can include a notification function, which provides a pop-up message at the workstation where printing occurs to alert the operator that there are authorized compounding orders awaiting printing Clicking on the pop-up message opens a list of the orders awaiting label printing that the operator can access to perform the printing function.

Figure 12:
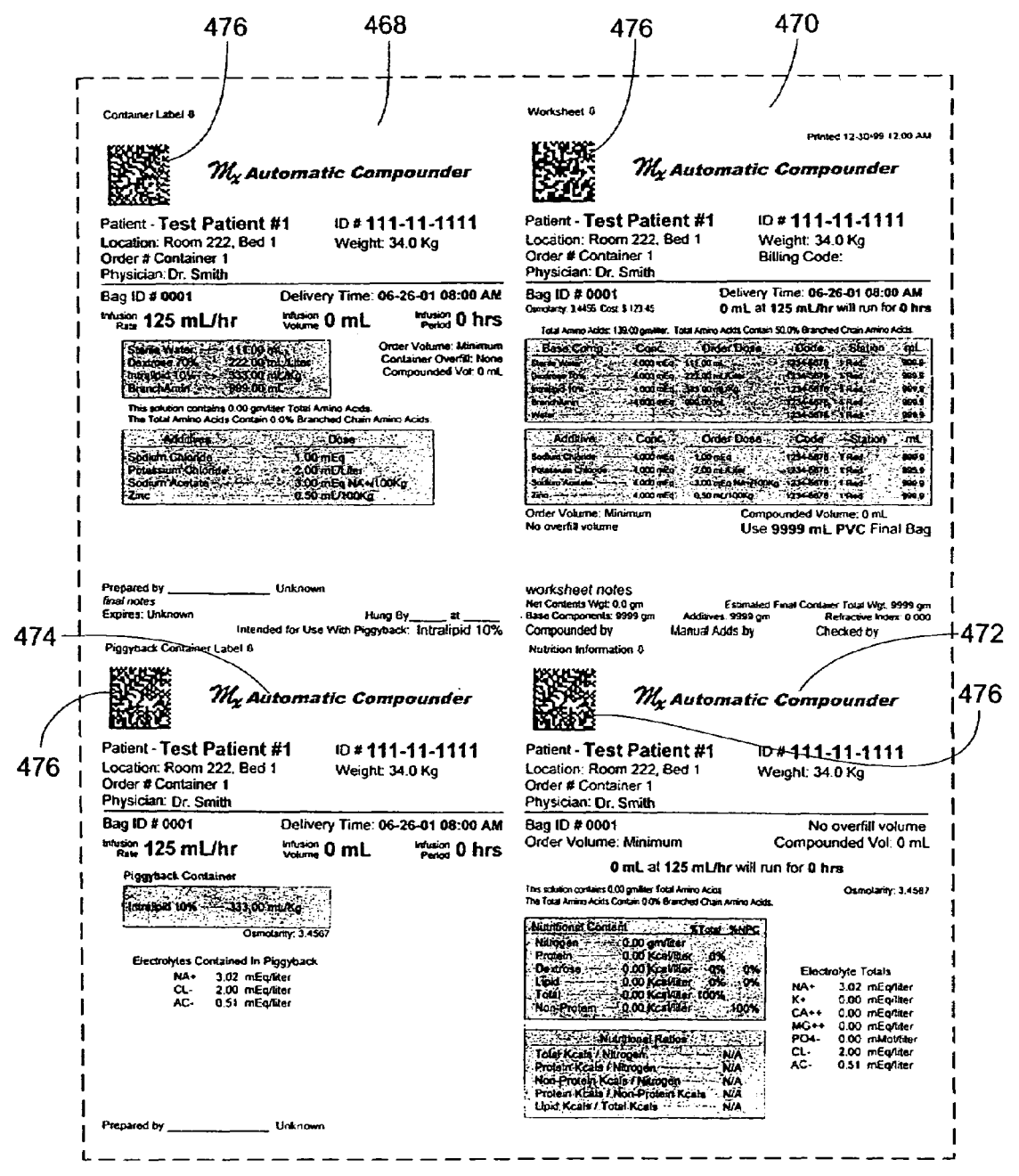

The order entry process manager 84 formats the labeling (see FIG. 12) based upon the information entered in the Order Entry window 436. The labeling includes a label 468 for the final solution container 14, a worksheet 470 identifying the source solutions and targeted compounding volumes, a worksheet 472 providing nutritional information for the contents of the final solution container 14, and a label 474 for a piggyback container, if ordered. The labeling also includes the bar codes 476 that the compounding control manager 72 requires to verify the compounding order and perform the actual compounding process. The final container bar code 476 (on the final solution container label 468) can also be used to electronically transfer formula information after compounding to a capable medication dispensing device (e.g., such as an infusion pump).

Upon completion of the printing step, the compounding order is made available for electronic transfer to a compounding control manager 72 of a compounding device 18. The PRINTED icon 478 is colored or highlighted on the Order Entry window 436 when the labeling printing step has been completed and the order has been made available for transfer to the compounding control manager 72 for completion.

In the networked compounding environment that the order entry process manager 84 makes possible, when it is time to compound, the compounding clinician at the compounding station logs into the compounding control manager 72 and selects the AUTO PGM touch button 234 on the main screen 202 generated by the compounding control manager 72 (see FIG. 9B). This opens a queue selection screen 236 (FIG. 9P), which displays a list of preprogrammed schedule queues that have been established by the previously described order entry and processing steps, as controlled by the order entry process manager 84. The operator selects the desired queue (based upon the present compounding shift—e.g., morning or afternoon) and presses the ENTER touch button on the queue selection screen 236. The compounding control manager 72 holds the order queue list it receives from the order entry process manager 84 in memory, and the main screen 202 (see FIG. 9Q) thereafter allows the operator to view the current order queue list in the window 238. In this arrangement, the operator selects the order from the programmed order queue list 238 on the main screen 202, and then, as prompted by the compounding control manager 72, proceeds to connect the final solution container 14 to the manifold 36, perform the source solution and final solution verifications, perform the flushing sequences (if necessary), and starts compounding in the manner previously described.

As previously described, the use of bar code data in the verification function of the compounding control manager 72 necessitates that the labeling (FIG. 12) that is generated by the order entry process manager 84 must be available to and used by the compounding clinician in order to operate the compounding device and complete the compounding order. This integrates the submission, authorization, and printing functions of the order entry process manager 84 with the control functions of the compounding control manager 72.

The compounding control manager 72 communicates with the order entry process manager 84 when the compounding process has been completed, the COMPOUNDED icon 480 on the Order Entry window is colored or highlighted accordingly.

The order entry process manager 84 can provide other functions that can be accessed through the PRESCRIPTION ORDERS menu box. For example, as shown in FIG. 11A, a Schedules component can be included that allows the operator to view and alter the scheduling of compounding orders by shifts.

Figure 10D:
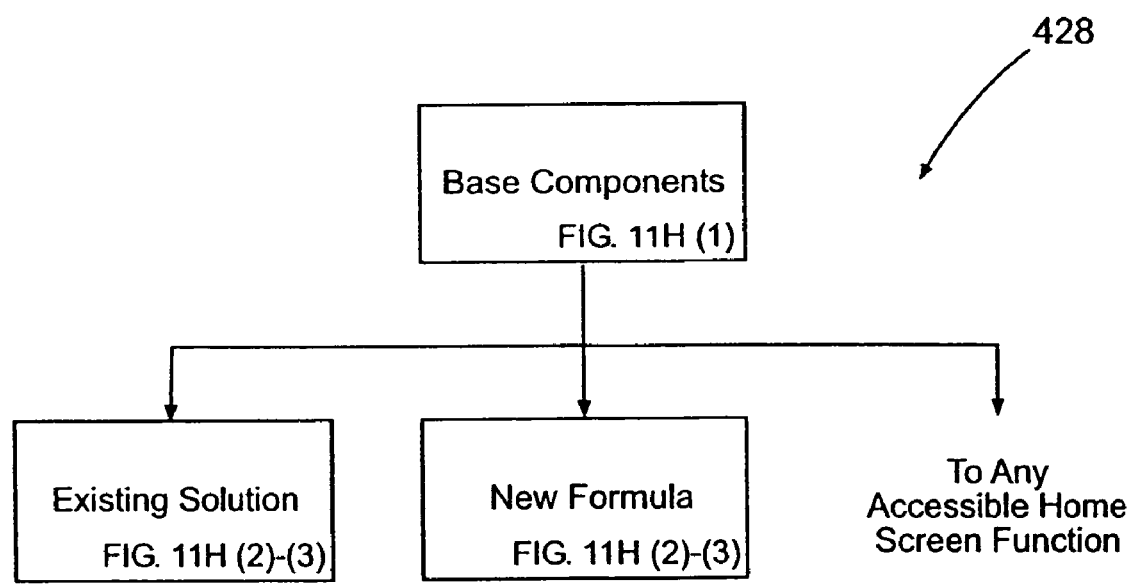

On the home screen shown in FIG. 11A, the operator can, with a mouse click, select other functional modules of the order entry process manager 84. If, for example, the operator seeks to view the inventory of base components maintained by the compounding facility, the operator mouse-clicks on the Base Components function of the SOURCE SOLUTIONS menu box 402, which opens the BASE COMPONENTS MAIN PAGE 482 shown on FIG. 11H(1). This window provides access to the features of the Base Solutions Data Base Component 428 of the order entry process manager 84, the functional units of which are shown schematically in FIG. 10D.

Figure 11H:
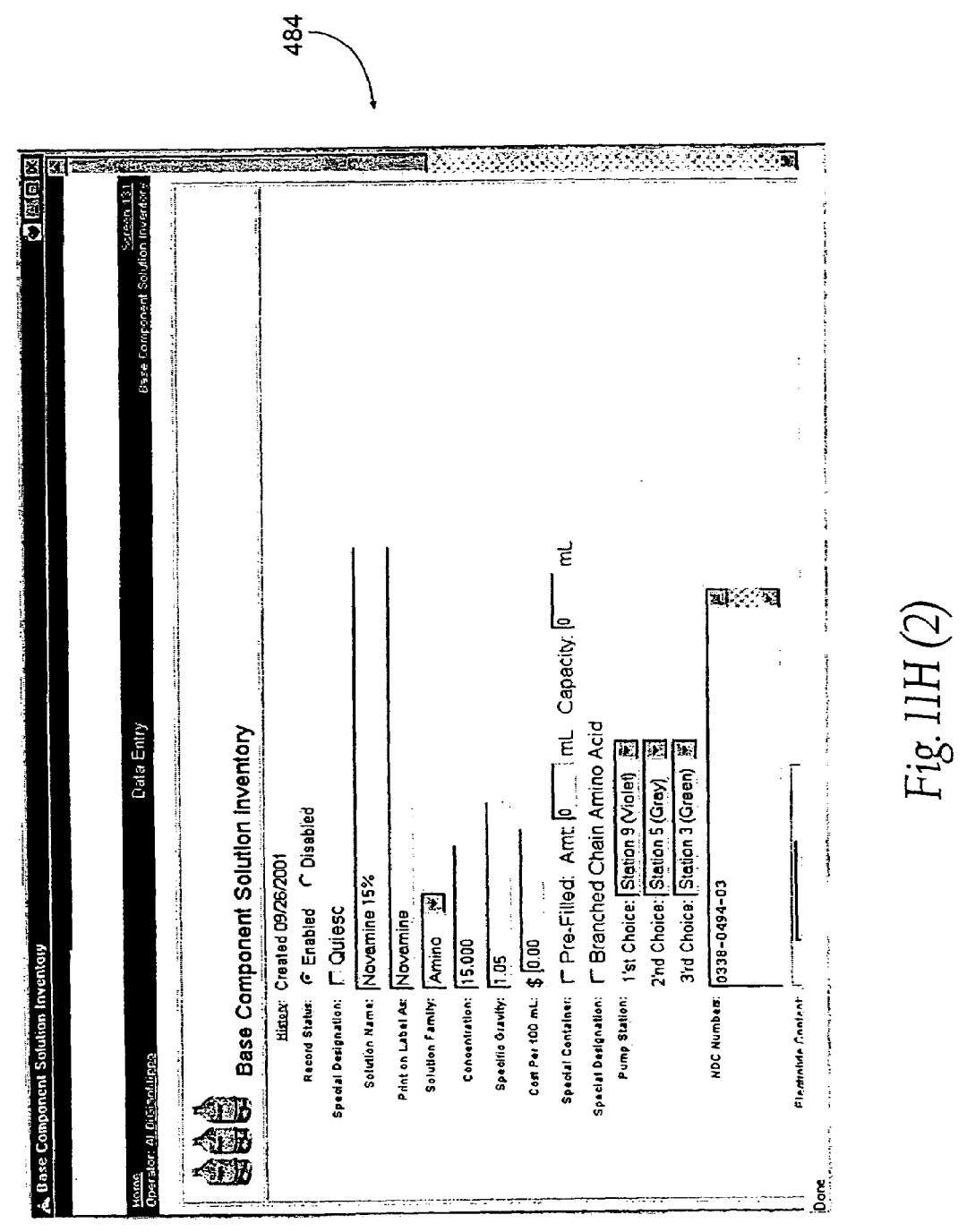
Figure 11H:
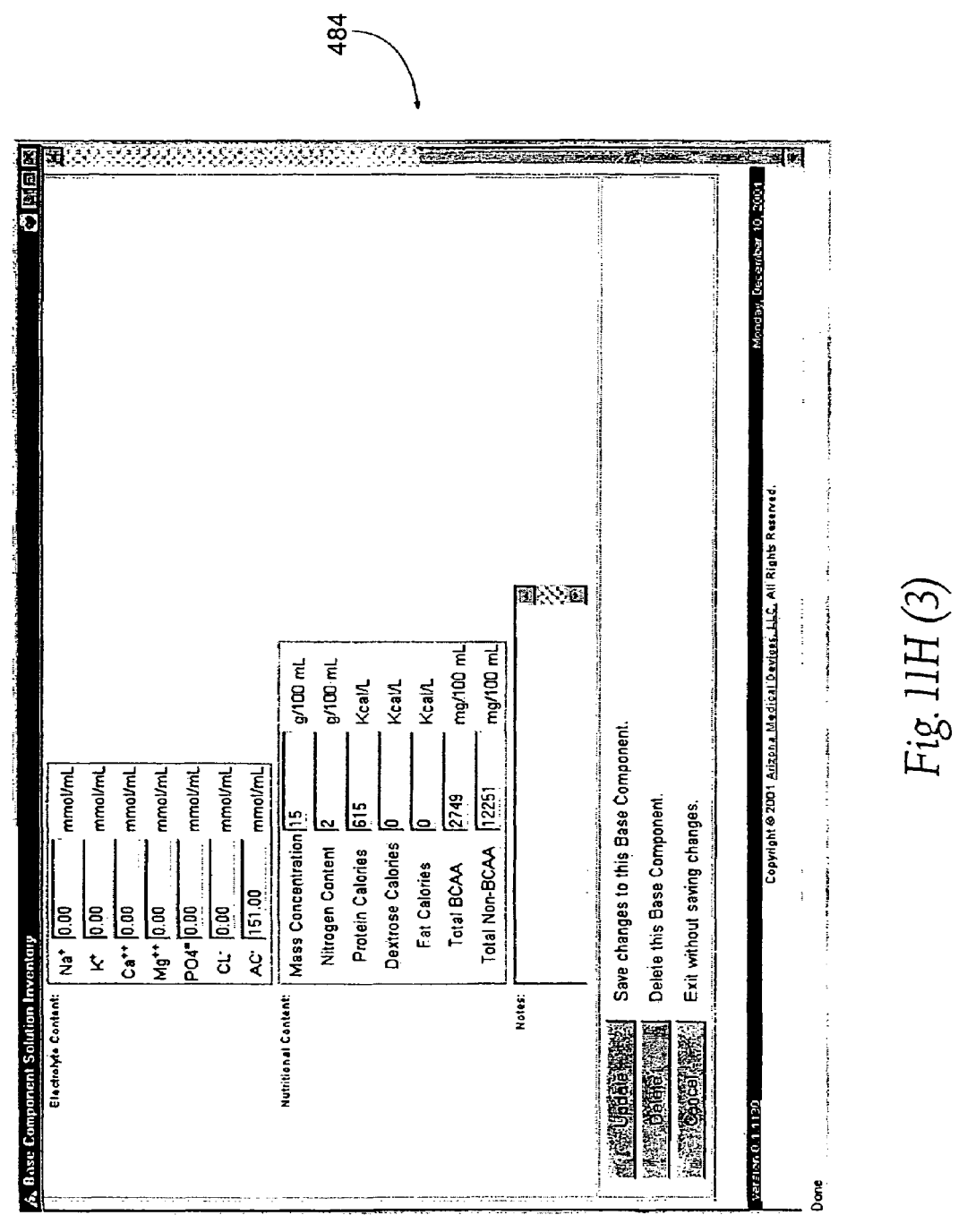
Figure 11:
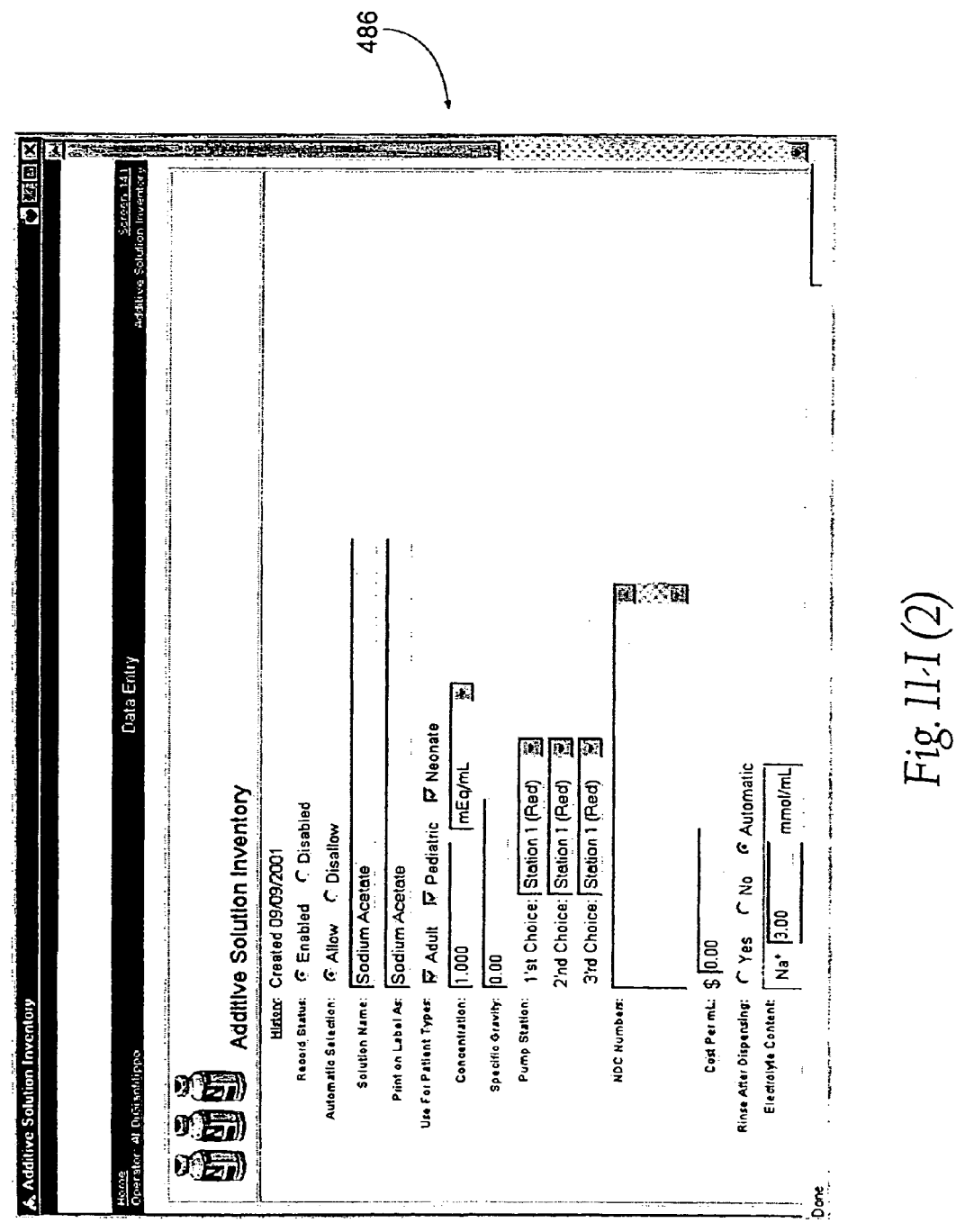

When selected, the BASE COMPONENTS MAIN PAGE 482 (FIG. 11H(1)) permits the operator to select a base component maintained in the existing facility inventory, or to add a base component to the inventory. Selection of a base component opens a scrollable Base Component Inventory Page 484 pertaining to the selected component, as shown in FIGS. 11H(2) and 11H(3). The Base Component Inventory Page 484 allows entry and retention by the order entry process manager 84 of pertinent information pertaining to the selected base component—e.g., its name; family type (Amino Acid, Dextrose, Fat Emulsion, etc.); concentration; specific gravity; cost per 100 mL; the choice of the pump rotor assembly of the compounding device to convey the component; NDC lot number; expiration date; electrolyte content, nutritional content, and other information.

Figure 10E:
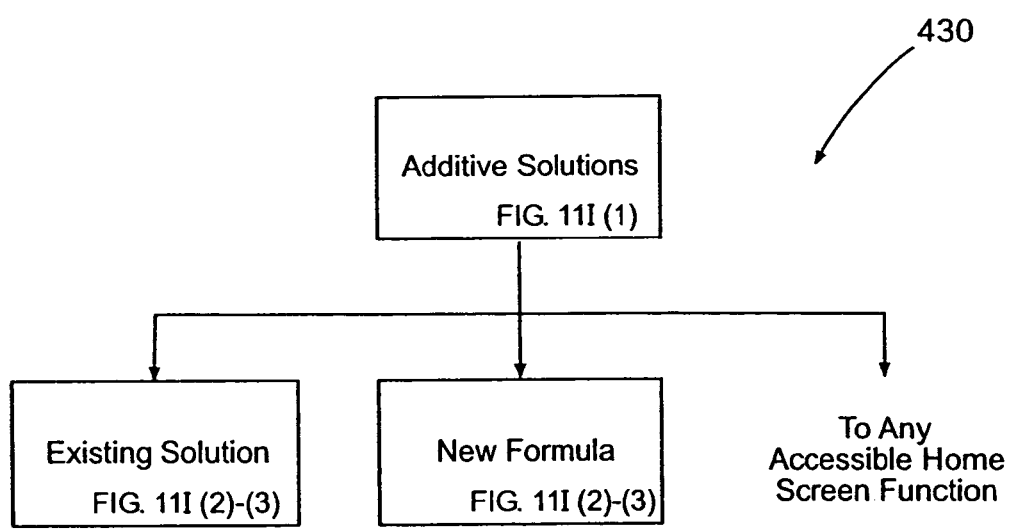
Figure 11I:
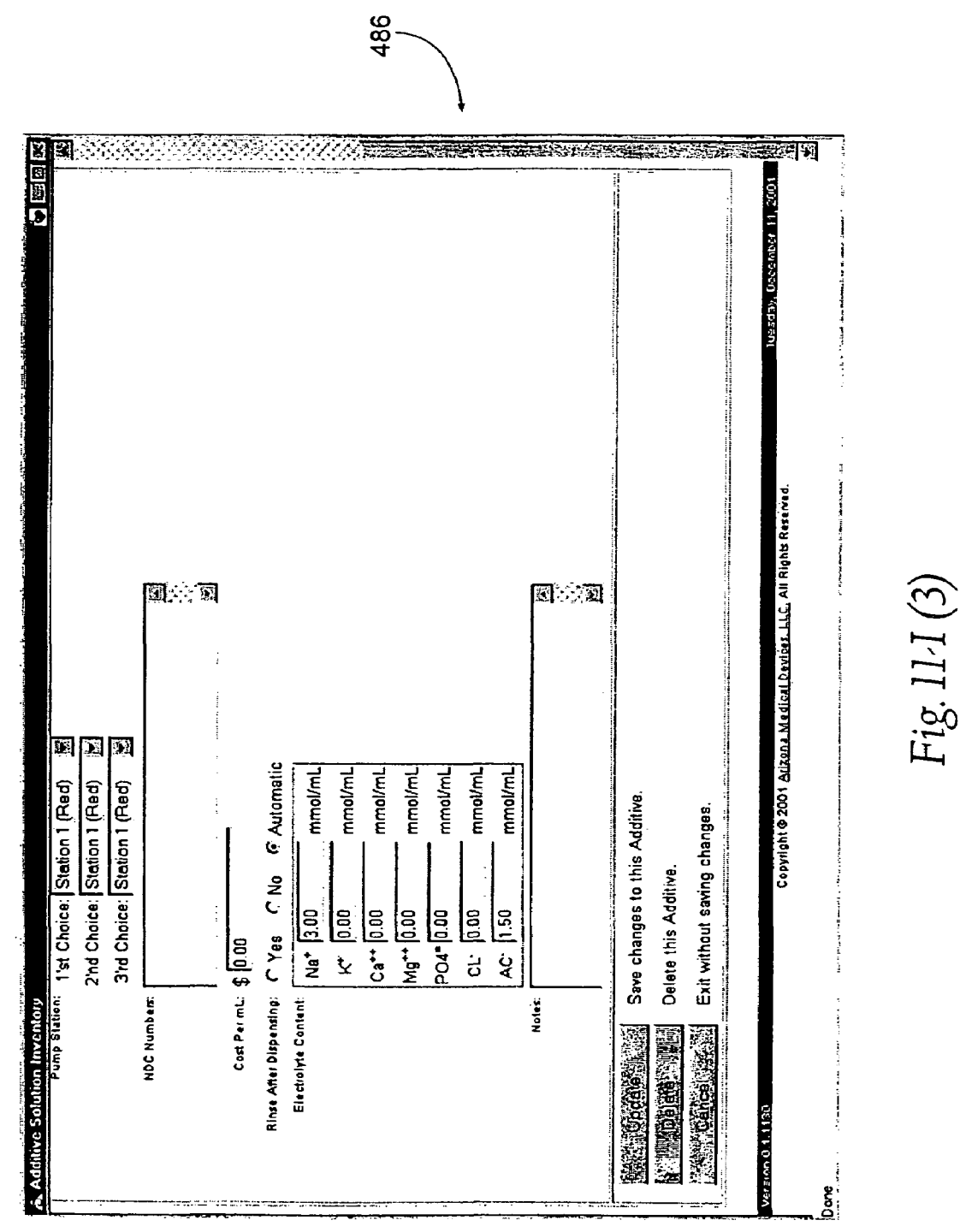

Similarly, if the operator seeks to access the inventory of additive solutions maintained by the compounding facility, the operator mouse-clicks on the Additive Solutions function of the SOURCE SOLUTIONS menu box 402, which opens the ADDITIVE SOLUTIONS MAIN PAGE 486 shown on FIG. 11I(1). This window provides access to the features of the Additive Solutions Data Base Component 430 of the order entry process manager 84, the functional units of which are shown schematically in FIG. 10E.

When selected, the ADDITIVE SOLUTIONS MAIN PAGE 486 (FIG. 11I(1)) permits the operator to select an additive solution maintained in the existing facility inventory, or to add an additive solution to the inventory. Selection of an additive solution opens a scrollable Additive Solution Inventory Page 488 pertaining to the selected additive solution, as shown in FIGS. 11I(2) and 11I(3). The Additive Solution Inventory Page 488 allows entry and retention by the order entry process manager 84 of pertinent information pertaining to the selected additive solution—e.g., its solution type; its patient type; concentration; specific gravity; cost per mL; the choice of the pump rotor assembly of the compounding device to convey the component; NDC lot number; expiration date; electrolyte content; and other information.

The Base Solutions Data Base Component 428 and the Additive Solutions Data Base Component 430 of the order entry process manager 84 store pertinent information, for cross-reference by the other functional modules of the order entry process manager 84. For example, the Formula Library 426 draws upon information stored in the Base Solutions Data Base 428 and the Additive Solutions Data Base 430 to fill out the default information in the formula templates. Thus, library solutions can be restricted by patient type. As another example, the nutritional information derived by the order entry process manager 84 contained in the printed labeling (label 472 in FIG. 12) is drawn from information stored in the Base Solutions Data Base 428. Administration reports (to be described later) derive inventory, use, and cost management information based upon information stored in the Base Solutions Data Base 428 and the Additive Solutions Data Base 430.

From the home page shown in FIG. 11A, the operator can, with a mouse click, select to access the report module 404. The operator can select among a list of report selections contained in the REPORTS menu box 404. The reports module 404 provides an operator the capability of tracking compounding activities and generating various administrative reports relating to these activities. The nature and format of the reports can, of course, vary according to the particular requirements of the compounding facility. The reports module 404 can generate reports that, for example, (i) list the compounding orders entered during a prescribed reporting period (arranged, e.g., by patient, date, time, entry operator, and the like); or (ii) list the compounding orders that were compounded during a prescribed reporting period (arranged, e.g., by compounding device number, date, time, compounding clinician, patient, final container number, time elapsed, and the like); or (iii) list source solution usage in liters during a prescribed reporting period arranged, e.g., by solution type, day, month, cost, and/or lot numbers, and the like; or (iv) list customer billing records for completed compounded containers, including, e.g., costs per mL of compounded fluid by solution type, flat rates costs by container or solution type, labor costs by machine compounding hours, flat labor costs, or a combination of any of these; or (v) list a log of operators accessing the order entry processing manager, arranged, e.g., by date, time, operator name, and event. Any or all of these reports can be generated by the reports module 404 of the order entry process manager 84 according to preformatted templates, or by customized or relational field searches of data bases maintained by the order entry process manager 84. The reports module 404 desirably includes the capability of formatting the reports for printing in hard copy format, or offloading the reports in electronic file format, e.g., in PDF file format.

From the home page shown in FIG. 11A, the operator can, with a mouse click, select to access the administration module 406. The operator can select among a list of administration options contained in the ADMINISTRATION menu box 406. The administration module aids the operator, who is in this instance typically the compounding activity administrator or supervisor, in the performance of various administration tasks in support of the compounding activity.

The nature of the administrative functions supported by the administration module 406 can, of course, vary according to the particular requirements of the compounding facility. The administration module 406, for example, can allow the administrator to add, delete or modify the schedule of shifts during which compounding takes place—which, in turn, becomes viewable (box. 460) in the Order Entry web page (FIG. 11E(4)), for selection by the authorizing pharmacist during the order authorization process. The administration module 406, as another example, can allow the administrator to add, delete or modify the inventory list of compounding devices maintained by the compounding facility—which information, in turn, becomes available for use in the compounding reports generated by the reports module 404. The administration module 406, as another example, can allow the administrator to add, delete or modify the categories of patient types (e.g., standard adult; standard neonate; standard pediatric) accounted for by the compounding facility—which, in turn, can be linked to the patient information data base and can also be linked to the formula template data base 426 maintained by the order entry process manager 84 (i.e., a standard adult formula template can be linked to a standard adult patient type, to facilitate the compound order entry process). The administration module 406, as another example, can allow the administrator to add, delete or modify the list of operators by name or by operator groups (e.g., administrative staff, pharmacy staff, pharmacy technician, supervisor) that are permitted access to the order entry process manager 84, as well as assign passwords and access rights particular to each operator and each operator group. In this respect, operator's rights and restrictions can be tailored for that operator individually, and not as part of an overall group (e.g., as a technician or a pharmacist). Groups can also be prohibited or allowed access to certain patient types (e.g., Dr. Brown cannot see information pertaining to Dr. Smith's patients).

On the home page shown in FIG. 11A, selection among the options provided by the navigation module 408 of the order entry process manager 84 can provide a short cut to the operator's home page, a help function, a general data base search function outside of the order entry, report, or administration functions, and/or a user log-out function. Selective use of operator access rights allows for patient record privacy in compliance with governmental HIPAA regulations.

As can be by now be appreciated, the order entry process manager 84 and browser software provide a physician or compounding order facility the capability to electronically transfer compounding requirements to a compounding facility via direct wire, network, or internet based systems. The order entry process manager 84 and browser software provides a compounding facility the capability to electronically enter compounding requirements on site or to receive electronically generated customer compounding requirements from remote sites. The order entry process manager 84 and browser software provide a compounding facility the capability to queue multiple customer compounding requirements into an efficient compounding and delivery schedule. The order entry process manager 84 and browser software provide a compounding facility the capability to generate container labels, including bar codes, as well as control the actual compounding process. The order entry process manager 84 and browser software provides a compounding facility the capability to automatically generate customer billing and inventory control for completed compounded containers. Billing options can include costs per mL of compounded fluid by solution type, flat rates costs by bag or solution type, labor costs by machine compounding hours, flat labor costs, or a combination of any of these.

Features of the invention are set forth in the following claims.

We claim:

1. A pharmaceutical compounding device comprising
a driver,
a drive shaft coupled to the driver for rotation, the drive shaft extending along a first axis,
an idler shaft extending along a second axis offset from the first axis,
a peristaltic pump rotor carried on the idler shaft,
a drive gear carried on the drive shaft and coupled to the peristaltic pump rotor, and
a clutch assembly on the drive shaft coupled to the drive gear, the clutch assembly being operable in a first mode to disengage the drive gear from the drive shaft and a second mode to engage the drive gear with the drive shaft, to thereby selectively impart rotation of the drive shaft to the peristaltic pump rotor.

2. A device according to claim 1, further including a controller coupled to the driver to control rate of rotation of the drive shaft.

3. A device according to claim 2, wherein the controller employs PID control of the driver.

4. A device according to claim 3, wherein the PID control includes fuzzy logic.

* * * * *